(12) United States Patent
Mehra et al.

(10) Patent No.: US 11,977,072 B2
(45) Date of Patent: May 7, 2024

(54) SOLUTION-BASED PLASMONIC SPECIFIC-BINDING PARTNER ASSAYS USING METALLIC NANOSTRUCTURES

(71) Applicant: ZOETIS SERVICES LLC, Parsippany, NJ (US)

(72) Inventors: Rajesh K. Mehra, Union City, CA (US); Kenneth P. Aron, Union City, CA (US); Vincent Chiang, Union City, CA (US); Sarah Ann Unser, Union City, CA (US)

(73) Assignee: Zoetis Services LLC, Parsippany, NJ (US)

( * ) Notice: Subject to any disclaimer, the term of this patent is extended or adjusted under 35 U.S.C. 154(b) by 717 days.

(21) Appl. No.: 16/479,663

(22) PCT Filed: Jan. 30, 2018

(86) PCT No.: PCT/US2018/015981
§ 371 (c)(1),
(2) Date: Jul. 22, 2019

(87) PCT Pub. No.: WO2018/140953
PCT Pub. Date: Aug. 2, 2018

(65) Prior Publication Data
US 2022/0091113 A1  Mar. 24, 2022

Related U.S. Application Data

(60) Provisional application No. 62/451,932, filed on Jan. 30, 2017.

(51) Int. Cl.
| G01N 33/543 | (2006.01) |
| G01N 21/53 | (2006.01) |
| G01N 21/552 | (2014.01) |
| G01N 33/553 | (2006.01) |

(52) U.S. Cl.
CPC ..... *G01N 33/54346* (2013.01); *G01N 21/554* (2013.01); *G01N 33/553* (2013.01); *G01N 2469/10* (2013.01); *G01N 2469/20* (2013.01)

(58) Field of Classification Search
None
See application file for complete search history.

(56) References Cited

U.S. PATENT DOCUMENTS

| 4,704,366 | A | 11/1987 | Juarez-Salinas et al. |
| 5,061,381 | A | 10/1991 | Burd |
| 5,122,284 | A | 6/1992 | Braynin et al. |
| 5,186,844 | A | 2/1993 | Burd et al. |
| 5,304,348 | A | 4/1994 | Burd et al. |
| 5,457,053 | A | 10/1995 | Burd et al. |
| 5,624,597 | A | 4/1997 | Buhl et al. |
| 5,693,233 | A | 12/1997 | Schembri |
| 5,939,021 | A | 8/1999 | Hansen et al. |
| 6,579,726 | B1 | 6/2003 | Natan et al. |
| 6,660,381 | B2 | 12/2003 | Halas et al. |
| 6,685,986 | B2 | 2/2004 | Oldenburg et al. |
| 6,699,724 | B1 | 3/2004 | West et al. |
| 6,861,263 | B2 | 3/2005 | Natan |
| 6,970,239 | B2 | 11/2005 | Chan et al. |
| 7,135,054 | B2 | 11/2006 | Jin et al. |
| 7,144,627 | B2 | 12/2006 | Halas et al. |
| 7,212,692 | B2 | 5/2007 | Yan |
| 7,307,731 | B2 | 12/2007 | Naya |
| 7,405,054 | B1 | 7/2008 | Hasenbank et al. |
| 7,648,595 | B2 | 1/2010 | Jin et al. |
| 7,732,145 | B2 | 6/2010 | Kang et al. |
| 7,790,066 | B2 | 9/2010 | Wang et al. |
| 7,807,633 | B2 | 10/2010 | Haynie et al. |
| 8,101,424 | B2 | 1/2012 | Geddes |
| 8,110,250 | B2 | 2/2012 | Ojima et al. |
| 8,263,418 | B2 | 9/2012 | Brennan et al. |
| 8,426,152 | B2 | 4/2013 | Gerion et al. |
| 8,597,897 | B2 | 12/2013 | Kim et al. |
| 8,628,727 | B2 | 1/2014 | Van Duyne et al. |
| 8,697,129 | B2 | 4/2014 | Qian et al. |
| 8,753,559 | B2 | 6/2014 | Yang et al. |
| 8,784,895 | B2 | 7/2014 | Messersmith et al. |
| 8,808,420 | B2 | 8/2014 | Adherne et al. |
| 9,034,656 | B2 | 5/2015 | Mehra et al. |
| 9,040,310 | B2 | 5/2015 | Ashworth-sharpe et al. |
| 9,217,746 | B2 | 12/2015 | Geddes |
| 9,308,582 | B2 | 4/2016 | Sun et al. |
| 9,835,622 | B2 | 12/2017 | Mehra et al. |
| 9,921,218 | B2 | 3/2018 | Mehra et al. |
| 10,281,465 | B2 | 5/2019 | Mehra et al. |
| 10,429,383 | B2 | 10/2019 | Mehra et al. |
| 10,488,409 | B2 | 11/2019 | Mehra et al. |
| 11,209,430 | B2 | 12/2021 | Mehra et al. |
| 11,215,614 | B2 | 1/2022 | Mehra et al. |
| 11,255,854 | B2 | 2/2022 | Mehra et al. |
| 11,614,447 | B2 | 3/2023 | Mehra et al. |

(Continued)

FOREIGN PATENT DOCUMENTS

| CN | 1417586 A | 5/2003 |
| CN | 1798976 A | 7/2006 |

(Continued)

OTHER PUBLICATIONS

Jana et al., Anal. Chem, 2015, 87:3964-3972. (Year: 2015).*

(Continued)

*Primary Examiner* — Nicole Kinsey White
(74) *Attorney, Agent, or Firm* — COOLEY LLP

(57) ABSTRACT

The present invention relates to nanostructure-binding partner conjugates, as well as reaction mixtures, analyte detection devices, and methods of making and using the conjugates. In particular, the invention provides a method of detecting a target analyte in a sample comprising mixing the sample with a first detection conjugate and a second detection conjugate in solution, wherein the first and second detection conjugates comprise metallic nanostructures coupled to binding partners that are capable of specifically binding to the target analyte if present in the sample to form a complex between the first detection conjugate, the analyte, and the second detection conjugate, wherein a change in an optical signal upon complex formation indicates the presence of the target analyte in the sample.

14 Claims, 32 Drawing Sheets

(56) References Cited

U.S. PATENT DOCUMENTS

| | | |
|---|---|---|
| 2001/0002315 A1 | 5/2001 | Schultz et al. |
| 2003/0170618 A1 | 9/2003 | Chien et al. |
| 2005/0037437 A1 | 2/2005 | Zeidler |
| 2006/0240573 A1 | 10/2006 | Kao et al. |
| 2006/0246513 A1 | 11/2006 | Bohannon |
| 2007/0054337 A1 | 3/2007 | Ferning et al. |
| 2007/0092978 A1 | 4/2007 | Mink et al. |
| 2008/0213814 A1 | 9/2008 | Gerion et al. |
| 2008/0227219 A1 | 9/2008 | Gamez |
| 2009/0018025 A1 | 1/2009 | Shao et al. |
| 2010/0028410 A1 | 2/2010 | Haynie |
| 2010/0062545 A1 | 3/2010 | Geddes |
| 2010/0120057 A1 | 5/2010 | Mehra et al. |
| 2010/0136566 A1 | 6/2010 | Mehra et al. |
| 2010/0159441 A1 | 6/2010 | Chiang et al. |
| 2010/0184086 A1 | 7/2010 | Callister |
| 2011/0065088 A1 | 3/2011 | Kang et al. |
| 2011/0124125 A1 | 5/2011 | Mehra et al. |
| 2011/0136143 A1 | 6/2011 | Castro et al. |
| 2011/0136155 A1 | 6/2011 | Mehra et al. |
| 2011/0275061 A1 | 11/2011 | Weidemaier et al. |
| 2012/0101007 A1 | 4/2012 | Ahern et al. |
| 2012/0162640 A1 | 6/2012 | Sakagami |
| 2012/0208174 A1 | 8/2012 | Galush et al. |
| 2012/0219966 A1 | 8/2012 | Kawamura |
| 2012/0252005 A1 | 10/2012 | Chiang et al. |
| 2013/0034854 A1 | 2/2013 | Ashworth-sharpe et al. |
| 2013/0115634 A1 | 5/2013 | Mehra et al. |
| 2013/0130404 A1 | 5/2013 | Mehra et al. |
| 2013/0172207 A1 | 7/2013 | Dai et al. |
| 2013/0189793 A1 | 7/2013 | Qian et al. |
| 2013/0203075 A1 | 8/2013 | Svenson et al. |
| 2013/0230717 A1 | 9/2013 | Xia et al. |
| 2013/0252275 A1 | 9/2013 | Tokonami et al. |
| 2014/0105982 A1 | 4/2014 | Oldenburg et al. |
| 2014/0121125 A1 | 5/2014 | Mehra et al. |
| 2014/0162067 A1 | 6/2014 | Shahjamali et al. |
| 2014/0170070 A1 | 6/2014 | Qian et al. |
| 2014/0272932 A1 | 9/2014 | Muerhoff et al. |
| 2014/0272933 A1 | 9/2014 | Dawson et al. |
| 2014/0308756 A1 | 10/2014 | Gautier et al. |
| 2014/0349317 A1 | 11/2014 | Kobayashi |
| 2015/0004102 A1 | 1/2015 | Hesham et al. |
| 2015/0017258 A1 | 1/2015 | Azzazy et al. |
| 2015/0038355 A1 | 2/2015 | Tan et al. |
| 2015/0212005 A1 | 7/2015 | Akhavan-Tafti et al. |
| 2015/0247846 A1 | 9/2015 | Gerion et al. |
| 2015/0293088 A1 | 10/2015 | Mehra et al. |
| 2016/0047804 A1 | 2/2016 | Mehra et al. |
| 2016/0120978 A1 | 5/2016 | Guler et al. |
| 2016/0153972 A1 | 6/2016 | Daynes et al. |
| 2016/0202251 A1 | 7/2016 | Goh et al. |
| 2017/0038366 A1 | 2/2017 | Mehra et al. |
| 2018/0059104 A1 | 3/2018 | Mehra et al. |
| 2018/0156790 A1 | 6/2018 | Mehra et al. |
| 2019/0219572 A1 | 7/2019 | Mehra et al. |
| 2020/0110086 A1 | 4/2020 | Mehra et al. |
| 2022/0074934 A1 | 3/2022 | Mehra et al. |
| 2022/0082562 A1 | 3/2022 | Mehra et al. |

FOREIGN PATENT DOCUMENTS

| | | |
|---|---|---|
| CN | 1902496 A | 1/2007 |
| CN | 101490554 A | 7/2009 |
| CN | 102023151 A | 4/2011 |
| CN | 102103145 A | 6/2011 |
| CN | 102323422 A | 1/2012 |
| CN | 103335984 A | 10/2013 |
| CN | 104105965 B | 7/2016 |
| CN | 106290893 A | 1/2017 |
| JP | H07-501880 A | 2/1995 |
| JP | H10-132818 A | 5/1998 |
| JP | 2000-028612 A | 1/2000 |
| JP | 2000-028614 A | 1/2000 |
| JP | 2000-146959 A | 5/2000 |
| JP | 2001-513198 A | 8/2001 |
| JP | 2003-514224 A | 4/2003 |
| JP | 2003149244 A | 5/2003 |
| JP | 2005520125 A | 7/2005 |
| JP | 2007-114129 A | 5/2007 |
| JP | 2008527332 A | 7/2008 |
| JP | 2009-516199 A | 4/2009 |
| JP | 2005-195440 A | 7/2009 |
| JP | 2009-150708 A | 7/2009 |
| JP | 2010-286331 A | 12/2010 |
| JP | 2010-537155 A | 12/2010 |
| JP | 2011-525966 A | 9/2011 |
| JP | 2012132875 A | 7/2012 |
| JP | 2012-215472 A | 11/2012 |
| JP | 2013-525800 A | 6/2013 |
| JP | 2014228385 A | 12/2014 |
| JP | 20157652 A | 1/2015 |
| JP | 2015507078 A | 3/2015 |
| JP | 2015-509936 A | 4/2015 |
| JP | 2016510126 A | 4/2016 |
| TW | 201408690 A | 3/2014 |
| WO | WO 2001/009388 A1 | 2/2001 |
| WO | WO-03008539 A2 | 1/2003 |
| WO | WO-2006074076 A1 | 7/2006 |
| WO | WO 2007/047924 A2 | 4/2007 |
| WO | WO 2007/061793 A2 | 5/2007 |
| WO | WO-2007053201 A2 | 5/2007 |
| WO | WO 2008/086054 A2 | 7/2008 |
| WO | WO 2008/116093 A2 | 9/2008 |
| WO | WO-2009117510 A2 | 12/2009 |
| WO | WO 2010/006201 A2 | 1/2010 |
| WO | WO 2011/063003 A2 | 5/2011 |
| WO | WO 2011/063235 A2 | 5/2011 |
| WO | WO 2011/095636 A1 | 8/2011 |
| WO | WO 2011/139792 A2 | 11/2011 |
| WO | WO 2011/148870 A2 | 11/2011 |
| WO | WO 2012/077756 A1 | 6/2012 |
| WO | WO 2013/067524 A1 | 5/2013 |
| WO | WO 2013/078227 A1 | 5/2013 |
| WO | WO 2013/169640 A1 | 11/2013 |
| WO | WO-2014020293 A1 * | 2/2014 ....... G01N 33/57434 |
| WO | WO 2014/059274 A1 | 4/2014 |
| WO | WO-2014132833 A1 | 9/2014 |
| WO | WO 2015/160923 A1 | 10/2015 |
| WO | WO 2016/007942 A1 | 1/2016 |
| WO | WO 2016/025703 A2 | 2/2016 |
| WO | WO 2016/134214 A1 | 8/2016 |
| WO | WO 2016/170183 A1 | 10/2016 |
| WO | WO 2017/024163 A1 | 2/2017 |
| WO | WO 2018/140953 A1 | 8/2018 |

OTHER PUBLICATIONS

Jana et al., Anal. Chem, 2015, 87(7):3964-3972. (Year: 2015).*

Pei et al., Journal of Materials Chemistry B, 2013, 1:3992-3998. (Year: 2013).*

[Author Unknown], "Sorvall Legend XT Sorvall Legend XTR Instruction Manual," Thermo Fisher Scientific, No. 50119927-4, Feb. 14, 2011 (Feb. 14, 2011), pp. 1-59. Retrieved from the Internet: <http://core.phmtox.msu.edu/Scheduling/ItemDocs/40/XTR_Manual.pdf> on Mar. 7, 2018 (Mar. 7, 2018).

BANGS Laboratories, Inc., "Lateral Flow Tests," TechNote 303, available at http://www.bangslabs.com/sites/default/files/bangs/docs/pdf/303.pdf, 1999. 6 pages.

Atanasov, P.A. et al., "Noble metallic nanostructures: preparation, properties, applications", Journal of Physics: Conference Series 514 (2014), pp. 1-8.

Bolduc and Masson, "Advances in surface plasmon resonance sensing with nanoparticles and thin films: nanomaterials, surface chemistry, and hybrid plasmonic techniques." Anal Chem. (2011); 83 (21): 8057-8062. Epub Aug. 29, 2011.

Bui, Minh-Phuong N. et al., "Gold nanoparticle aggregation-based highly sensitive DNA detection using atomic force microscopy", Anal Bioanal Chem (2007), 388: 1185-1190.

Dong, P., et al., "Ultrathin Gold-Shell Coated Silver Nanoparticles onto a Glass Platform for Improvement of Plasmonic Sensors." ACS Appl. Mater. Interfaces (2013); 5 (7): 2392-2399.

(56) References Cited

OTHER PUBLICATIONS

European Patent Application No. 12852350.3, Extended European Search Report dated May 13, 2015, 10 pages.
European Patent Application No. 15831667.9, Supplementary European Search Report dated Nov. 30, 2017, 9 pages.
European Patent Application No. 16833889.5, Extended European Search Report dated Dec. 21, 2018, 7 pages.
European Patent Application No. 18196372.9, Extended European Search Report dated Feb. 21, 2019, 13 pages.
Fan, Chao-Ming et al. "A study of double antigen sandwich colloidal gold immunochromatography rapid detection for *Mycobacterium tuberculosis* antibody", US National Library of Medicine Database accession No. NLM21729624 (May 2011), 2 pages.
Gupta, S. et al., "Characterization and optimization of gold nanoparticle-based silver-enhanced immunoassays", Anal. Chem. (2007), 79: 3810-3820.
Gupta, R. et al., "Preparation and characterization of surface plasmon resonance tunable gold and silver films", Journal of Applied Physics (2002), 92(9): 5264-5271.
Helmerhorst, E. et al., "Real-time and label-free bio-sensing of molecular interactions by surface plasmon resonance: A Laboratory Medicine Perspective", Clin Biochem Rev (2012), 33: 161-173.
Hong, W. et al. "Development of an up-converting phosphor technology-based 10-channel lateral flow assay for profiling antibodies against Yersinia pestis", J Microbiol Methods (2010), 83(2): 133-140.
Jana, et al., "Capping Agent-Free Gold Nanostars Show Greatly Increased Versatility and Sensitivity for Biosensing." Anal. Chem. (2015); 87 (7): 3964-3972.
Jia, K., et al., "Strong Improvements of Localized Surface Plasmon Resonance Sensitivity by Using Au/Ag Bimetallic Nanostructures Modified with Polydopamine Films." ACS Appl. Mater. Interfaces (2014); 6 (1): 219-227.
Kvítek, O., et al., "Noble metal nanostructures influence of structure and environment on their optical properties." Journal of Nanomaterials (2013); vol. 2013, Article ID 743684, pp. 1-15, 16 pages.
LamdaGen. Plasmonic ELSA. [online] Apr. 21, 2014 [retrieved Nov. 27, 2015]. Available on the internet at <URL:http://web.archive.org/web/20140421112507/http://lamdagen.com/lspr-verview/plasmonic-elisa/>, 1 page.
Li, M. et al., "Three-dimensional hierarchical plasmonic nano-architecture enhanced surface-enhanced raman scattering immunosensor for cancer biomarker detection in blood plasma", ACS Nano. (2013), 7(6): 4967-4976.
Mohammed and Desmulliez, "Lab-on-a-chip based immunosensor principles and technologies for the detection of cardiac biomarkers: A Review", Lab Chip (2011), 11(4): 569-595.
Mott, et al., "Synthesis of Size and Shape Controlled Silver Nanoparticles Coated by a Thin Layer of Gold and Their Use as Ultrasensitive Biomolecular Probes." Mater. Res. Soc. Symp. Proc. (2010); Materials Research Society 1253-K09-04, vol. 1253, 6 pages.
Nitin, N. et al., "Oligonucleotide-coated metallic nanoparticles as a flexible platform for molecular imaging agents", Bioconjug Chem. (2007), 18(6): 2090-2096.
Oh, Bo-Ram et al., "Integrated nanoplasmonic sensing for cellular functional immunoanalysis using human blood", ACS Nano. (2014), 8(3): 2667-2676.
Park, et al., "Nanostar Clustering Improves the Sensitivity of Plasmonic Assays". Bioconjug Chem. (Aug. 19, 2015); 26(8): 1470-1474. Epub Jul. 2, 2015.
Paul, S. et al., "Surface plasmon resonance imaging detection of silver nanoparticle-tagged immunoglobulin", J. R. Soc. Interface (2011), 8: 1204-1211.
PCT/US2012/066108, Invitation to Pay Additional Fees, dated Jan. 8, 2013, 2 pages.
PCT/US2012/066108, International Search Report and Written Opinion, dated Mar. 25, 2013, 10 pages.
PCT/US2012/066108, International Preliminary Report on Patentability, dated May 27, 2014, 7 pages.
PCT/US2015/045041, Invitation to Pay Additional Fees, dated Oct. 20, 2015, 3 pages.
PCT/US2015/045041, International Search Report and Written Opinion, dated Jul. 26, 2016, 13 pages.
PCT/US2015/045041, International Preliminary Report on Patentability, dated Feb. 14, 2017, 8 pages.
PCT/US2016/045606, International Preliminary Report on Patentability, dated Feb. 6, 2018, 9 pages.
PCT/US2016/045606, International Search Report, dated Oct. 24, 2016, 2 pages.
PCT/US2016/045606, Written Opinion, dated Oct. 24, 2016, 8 pages.
PCT/US2018/015981, International Preliminary Report on Patentability, dated Jul. 30, 2019, 15 pages.
PCT/US2018/015981, International Search Report and Written Opinion, dated Apr. 13, 2018, 22 pages.
Raphael, M.P. et al., "Quantitative LSPR imaging for biosensing with single nanostructure resolution", Biophysical Journal (2013), 104(1): 30-36.
Ruemmele, J.A. et al., "A localized surface plasmon resonance imaging instrument for multiplexed biosensing", Anal Chem. (2013), 85(9): 4560-4566.
Seekell, K. et al., "Optimization of immunolabeled plasmonic nanoparticles for cell surface receptor analysis", Methods. (2012), 56(2): 310-316.
Shao, Y. et al., "Optical fiber LSPR biosensor prepared by gold nanoparticle assembly on polyelectrolyte multilayer", Sensors (2010), 10: 3585-3596.
Stringer et al., "Development of an optical biosensor using gold nanoparticles and quantum dots for the detection of Porcine Reproductive and Respiratory Syndrome Virus", Sensors and Actuators B: Chemical (2008), 134(2): 427-431.
Tauran, Y. et al., "Molecular recognition by gold, silver and copper nanoparticles", World J Biol Chem. (2013), 4(3): 35-63.
Tokel, O. et al., "Advances in plasmonic technologies for point of care applications", Chem Rev. (2014), 114(11): 5728-5752.
Truong, P.L., et al., "A new method for non-labeling attomolar detection of diseases based on an individual gold nanorod immunosensor." Lab Chip (2011); 11: 2591-2597.
Walters and Parkin, "The incorporation of noble metal nanoparticles into host matrix thin films: synthesis, characterisation and applications", J. Mater. Chem. (2009), 19: 574-590.
Wu et al., "Gold Nanoparticle-Based Enzyme-Linked Antibody-Aptamer Sandwich Assay for Detection of *Salmonella typhimurium*." ACS Applied Materials and Interfaces (2014); 6: 16974-16981.
Wu, et al., "Bioassay of prostate-specific antigen (PSA) using microcantilevers." Nature Biotechnology (2001); 19: 856-860.
Zhang and Cremer, "Interactions between macromolecules and ions: the Hofmeister series." Blood (2006); 10 (6): 658-663.
Cui, et al., "Synthesis of AgcoreAushell Bimetallic Nanoparticles for Immunoassay Based on Surface-Enhanced Raman Spectroscopy". J Phys Chem B. (Mar. 9, 2006); 110(9): 4002-4006.
Mott, et al., "A Study on the Plasmonic Properties of Silver Core Gold Shell Nanoparticles: Optical Assessment of the Particle Structure". Japanese Journal of Applied Physics (Jun. 20, 2011); vol. 50, No. 6R, 8 pages.
Murshid, et al., "Gold plating of silver nanoparticles for superior stability and preserved plasmonic and sensing properties". Chem Commun. (Dec. 18, 2013); 49(97): 11355-11357.
Singh, et al., "Intensification of surface enhanced Raman scattering of thiol-containing molecules using Ag@Au core@shell nanoparticles". Journal of Applied Physics (2011); 109 (9): 1-38, 094301. Epub May 2, 2011.
European Patent Application No. 21177342.9, Extended European Search Report dated Dec. 23, 2021, 15 pages.
European Patent Application No. 18745189.3, Partial Supplementary European Search Report dated Aug. 27, 2020, 20 pages.
Jana, et al., *Supporting Information for* "Capping Agent-Free Gold Nanostars Show Greatly Increased Versatility and Sensitivity for Biosensing". Anal. Chem. (2015); 87 (7): 3964-3972, 11 pages.
Lyon, et al., "Colloidal Au-Enhanced Surface Plasmon Resonance Immunosensing". Anal. Chem. (1998); 70: 5177-5183.

(56) References Cited

OTHER PUBLICATIONS

Moreton, et al., "Functionalization of Hollow Gold Nanospheres for use as Stable, Red-shifted SERS Nanotags". The Royal Society of Chemistry (2013); 7(14): 6075-6082, 8 pages, published on Mar. 6, 2015.

Riskin, et al., "Ultrasensitive Surface Plasmon Resonance Detection of Trinitrotoluene by a Bis-aniline-Cross-Linked Au Nanoparticles Composite". JACS (2009); 131: 7368-7378.

Zheng, et al., "[Gold Nanoparticles-Based Localized Surface Plasmon Resonance Scattering Analysis Method for the Determination of Trace Amounts of Hg(II)]". Spectroscopy and Spectral Analysis (Jun. 2014); 34(6): 1477-1481, and English Abstract.

European Patent Application No. 18745189.3, Extended Supplementary European Search Report dated Dec. 2, 2020, 16 pages.

Haes, A., et al., "Nanoscale plasmonics begins to unravel Alzheimer's disease", LaserFocusWorld, Jun. 1, 2005, www.laserfocusworld.com/test-measurement/research/article/16555980/nanoscale-plasmonics-begins-to-unravel-alzheimers-disease#:~:text=Nanoscale%20plasmonics%20begins%20to%20unravel%20Alzheimer%E2%80%99s%20disease%20An,an%20Alzheimer%E2%80%99s%20clinical%20diagnostic%20test.%20Jun%201st%2C%202005, 10 pages.

Song, et al., "Gold-modified silver nanorod arrays for SERS-based immunoassays with improved sensitivity", Journals of Materials Chemistry B (Nov. 1, 2014); 2(43): 7488-7494.

Sotiriou, et al., "Plasmonic biocompatible silver-gold alloyed nanoparticles", Chem Commun (Camb). (Nov. 14, 2014); 50(88): 13559-13562.

[Author Unknown], Alpha Assays Protein: Protein Interaction User Guide, PerkinElmer, Waltham, MA, USA, May 2011, 40 pages, https://www.blossombio.com/pdf/products/UG_Alphatech.pdf.

Shkilnyy, A. et al., "Poly(ethylene glycol)-stabilized silver nanoparticles for bioanalytical applications of SERS spectroscopy", Analyst (Jan. 1, 2009); vol. 134, No. 9, p. 1868-1872. Epub Jul. 6, 2009.

[Author Unknown], Alpha Protein-Protein Interaction User Guide, PerkinElmer Japan, Nov. 2017, 40 pages, https://www.perkinelmer.co.jp/Portals/0/resource/tech/tech_ls/protocol_collection/Alpha_Protein-Protein_Interaction_userguide.pdf.

Howes, et al., "Colloidal nanoparticles as advanced biological sensors". Science (Oct. 3, 2014); 346(6205): 1247390. Epub Oct. 2, 2014.

Kengo Yamaguchi, "Construction of high-density aggregates composed of various metal nanoparticles and their surface-enhanced Raman scattering properties", Proceedings of the Spring Annual Meeting of the Chemical Society of Japan, Mar. 10, 2016. vol. 96th, p. RMBUNNO.3PC-239. 1 page.

Kooij E.S., "From nanorods to nanostars: Turning the optical properties of gold nanoparticles", Colloids and Surfaces A: Physicochem. Eng. Aspects, 2012, vol. 413, pp. 231-238.

\* cited by examiner

1. C1 conjugate
2. BSA-blocked C1 conjugate
3. C6 conjugate
4. BSA-blocked C6 conjugate

FIGURE 25

HOFMEISTER SERIES

Cations

NH$_4^+$   K$^+$   Na$^+$   Li$^+$   Mg$^{2+}$   Ca$^{2+}$   guanidinium$^+$

Anions

SO$_4^{2-}$   HPO$_4^{2-}$   acetate-   citrate-   Cl-   NO$_3^-$   ClO$_3^-$   I-   ClO$_4^-$   SCN- ↑ surface tension          ↓ surface tension
harder to make cavity       easier to make cavity
↓ solubility hydrocarbons   ↑ solubility hydrocarbons
Salt out (aggregate)        Salt in (solubilize)
↓ protein denaturation      ↑ protein denaturation
↑ protein stability         ↓ protein stability

SOLUTION-BASED PLASMONIC SPECIFIC-BINDING PARTNER ASSAYS USING METALLIC NANOSTRUCTURES

CROSS-REFERENCE TO RELATED APPLICATIONS

This application is the U.S. National stage application of International Patent Application No. PCT/US2018/015981, filed Jan. 30, 2018, which claims the benefit of priority of U.S. Provisional Application No. 62/451,932, filed Jan. 30, 2017, which are hereby incorporated by reference in their entireties.

FIELD OF THE INVENTION

The present invention relates to systems and methods for detecting target analytes in a sample. In particular, the present invention provides a localized surface plasmon resonance-based analyte detection system capable of detecting a minute quantity of a target analyte in a sample.

BACKGROUND OF THE INVENTION

Current immunoassays and biomolecule binding assays typically require multiple steps and sophisticated equipment to perform the assays. The lack of sensitivity and the complexity involved in performing such heterogeneous assays arises from the specific need to separate labeled from unlabeled specific binding partners.

Attempts to develop assays based on the local surface plasmon resonance (LSPR) properties of noble metal nanoparticles have been made (Tokel et al., Chem Rev., Vol. 114: 5728-5752, 2014). LSPR is the collective oscillation of electrons in nanometer-sized structures induced by incident light. Metallic nanoparticles have a strong electromagnetic response to refractive index changes in their immediate vicinity and thus shifts in the resonance frequency of the nanoparticles can be measured as an indicator of molecules binding to the nanoparticle surface. Although metallic nanoparticles, particularly gold nanoparticles, have been employed in diagnostic assays to detect binding events, such assays generally suffer from low sensitivity and cannot be used to quantitatively monitor the kinetics of sequential binding events.

Thus, improved assay methods employing a homogenous format while providing increased sensitivity are needed. Assays utilizing standard laboratory techniques, such as spectroscopy, would also be desirable.

SUMMARY OF THE INVENTION

The present application describes the use of localized surface plasmon resonance (LSPR) techniques for performing assays involving specific binding partners including, but not limited to, ligands, receptors, transcription factors, binding DNA elements, antigens, and antibodies. More specifically, the present application relates to processes and materials for achieving significant amplification in such assays using nanostructure-binding partner conjugates. In some aspects, the present disclosure provides compositions and methods for achieving sensitive detection of molecules using LSPR techniques, and minimizing non-specific binding (NSB) levels in the assays provided.

In various embodiments described herein, the present application relates to nanostructure-binding partner conjugates, wherein the nanostructures are metallic nanostructures comprising a plurality of spikes. In some embodiments, the nanostructures are metallic nanostructures having an average diameter of at least 50 nm. In further embodiments, the nanostructures are metallic nanostructures having an average diameter of about 50 nm to about 120 nm. In some embodiments, the present disclosure provides the use of such metallic nanostructure-binding partner conjugates in solution to determine the binding of specific binding partners in a qualitative or quantitative manner. In some embodiments, the present disclosure provides methods for generating the conjugates described herein.

In one aspect, the present disclosure provides methods and compositions for detecting a target analyte in a sample, the method comprising mixing the sample with a first detection conjugate and a second detection conjugate in a solution, wherein the first and second detection conjugates comprise nanostructures coupled to binding partners that are capable of specifically binding to the target analyte if present in the sample to form a complex between the first detection conjugate, the analyte, and the second detection conjugate. In some embodiments, the nanostructures are anisotropic nanostructures that comprise a plurality of protrusions on spherical cores and wherein the average tip to tip diameter of the nanostructures is at least about 50 nm. In further embodiments, the average diameter of the nanostructures is about 70 nm or about 90 nm. In some embodiments, the nanostructures are spherical nanostructures. In further embodiments, the methods further comprise exposing the complex to a light source at a wavelength range within the ultraviolet-visible-infrared spectrum. In yet further embodiments, the methods comprise measuring an optical signal from the complex, wherein a change in the optical signal indicates the presence of the target analyte in the sample.

In some embodiments, more than two detection conjugates are used. For example, a third, a fourth, a fifth, or more detection conjugates are added. In some embodiments, each of the detection conjugates is capable of binding to the same target analyte to form a complex. In some embodiments, each of the detection conjugates binds to non-overlapping epitope(s) on the target analyte. In some embodiments, some or all of the conjugates are anisotropic.

In some embodiments, the mixing step occurs in the presence of 3-((3-Cholamidopropyl) dimethylammino)-1-propanesulfonate (CHAPS). In some embodiments, the CHAPS is present at a concentration of about 0.1% w/v to about 0.5% w/v. In further embodiments, the CHAPS is present at a concentration of about 0.2% w/v. Thus, in some embodiments, the solutions provided herein comprise CHAPS.

In some embodiments, the mixing step occurs in the presence of a polymeric material selected from polyethylene glycol (PEG), polyvinylpyrrolidone, methylcellulose, dextrans, polyallylamine, polyethyleneimine, polylysine, polyacrylic acid, polyglutamic acid, polyvinylalcohol, and polyaspartic acid. Thus, in some embodiments, the solutions provided herein comprise one or more of PEG, polyvinylpyrrolidone, methylcellulose, dextrans, polyallylamine, polyethyleneimine, polylysine, polyacrylic acid, polyglutamic acid, polyvinylalcohol, and/or polyaspartic acid. In some embodiments, the polymeric material is PEG. In some embodiments, PEG is present at a concentration from about 0.05% to about 5% w/v, or from about 0.1% to about 3%. In some embodiments, the PEG has a molecular weight of 1,000 to 300,000, or 2,000 to 250,000, or 3,000 to 200,000.

In some embodiments, the mixing step occurs in the presence of a viscosity enhancer. Thus, in some embodiments, the solutions provided herein comprise a viscosity enhancer. In further embodiments, the viscosity enhancer selected from trehalose, maltodextrin, sucrose, sorbitol, mannitol, polyvinylpyrrolidone (PVP), polyvinyl alcohol (PVA), cyclodextrins, randomly alkylated cyclodextrins, methylcellulose, trehalose, sucrose, sorbitol, mannitol and ficoll, dextran, or any combination thereof. In particular embodiments, the mixing step occurs in the presence of dextran at a concentration from about 0.05% to about 5%, depending on the molecular weight. For example, in some embodiments dextran is present at a concentration of about 0.05%, about 0.1%, about 0.5%, about 1%, about 1.5%, about 2%, about 2.5%, about 3%, about 3.5%, about 4%, about 4.5%, or about 5%.

In some embodiments, the mixing step occurs in the presence of gelatin. Thus, in some embodiments, the solutions provided herein comprise gelatin. In some embodiments, the gelatin is present at a concentration of between about 0.1% to about 3%, In some embodiments, solutions and reaction mixtures provided herein comprise at least one binding partner-nanostructure conjugate, CHAPS buffer, PEG, one or more Hofmeister series salts, EDTA, a polymer-based blocking reagent such as a Biolipidure®, BSA, gelatin, or any combination thereof. In some embodiments, the Hofmeister series salt is magnesium chloride. In other embodiments, the Hofmeister series salt is calcium chloride. In some embodiments the reaction mixture comprises multiple salts such as Hofmeister series salts. In some embodiments, the solutions and reaction mixtures provided herein comprise MgCL2 or NaSCN at a concentration of about 10 mM to about 250 mM, or at a concentration of about 100 mM. In some embodiments, the solutions and reaction mixtures provided herein comprise a citrate of the bivalent cation, for example, a citrate of Mg2+ or a citrate of Ca2+. In some embodiments, the solutions and reaction mixture comprises thiocyanate, manganese, cobalt, nickel, ethylenediaminetetraacetic acid (EDTA) and/or ethylene glycol-bis($\beta$-aminoethyl ether)-N,N,N',N'-tetraacetic acid (EGTA)). In some embodiments, the EDTA and/or EGTA is present in the solution at a concentration of about 5 mM to about 100 mM.

In some embodiments, the nanostructures employed in the methods and compositions provided herein comprise a plurality of protrusions, wherein the average tip-to-tip diameter of the nanostructures is about 50 nm, about 60 nm, about 70 nm, about 80 nm, about 90 nm, about 100 nm, about 110 nm, or about 120 nm. In some embodiments, the nanostructures are metallic nanostructures. In some embodiments, the nanostructures are gold metallic nanostructures. In some embodiments, the nanostructures provided herein are spherical nanostructures. In some embodiments, the average diameter of the spherical nanometers is about 50 nm, about 60 nm, about 70 nm, about 80 nm, about 90 nm, about 100 nm, about 110 nm, or about 120 nm.

In some embodiments, the present disclosure provides methods of detecting a target analyte in a sample comprising: (a) mixing the sample with a first detection conjugate, a second detection conjugate, CHAPS, bovine serum albumin (BSA), one or more polymeric material, one or more viscosity enhancer, a salt, and optionally a chelator, in a solution, wherein the first and second detection conjugates comprise nanostructures coupled to binding partners that are capable of specifically binding to the target analyte if present in the sample to form a complex between the first detection conjugate, the analyte, and the second detection conjugate; (b) exposing the complex to a light source at a wavelength range within the ultraviolet-visible-infrared spectrum; and (c) measuring an optical signal from the complex, wherein a change in the optical signal indicates the presence of the target analyte in the sample.

In some embodiments, the polymeric material is selected from the group consisting of PEG, polyvinyl pyrrolidone, gelatin, methylcellulose, dextran, poly allylamine, polyethyleneimine, polylysine, polyacrylic acid, polyvinylalcohol, and polyaspartic acid. In some embodiments, the viscosity enhancer is selected from the group consisting of trehalose, maltodextrin, sucrose, sorbitol, mannitol, polyvinylpyrrolidone (PVP) polyvinyl alcohol (PVA), cyclodextrin, methylcellulose, dextran, and ficoll. In some embodiments, the salt is selected from the group consisting of NaCl, MgCl2, CaCl$_2$, and NaSCN. In some embodiments, the chelator is selected from the group consisting of Ethylenediaminetetraacetic acid (EDTA) and ethylene glycol-bis($\beta$-aminoethyl ether)-N,N,N',N'-tetraacetic acid (EGTA).

In some embodiments, the solutions and reaction mixtures provided herein comprise a Biolipidure® reagent. In some embodiments, the Biolipidure® reagent is Biolipidure® 205, 206, 1002, 1201, 1202, or a combination thereof. In some embodiments, the nanostructures are selected from the group consisting of spherical nanoparticles and nanoparticles comprising a plurality of protrusions. Thus, in some embodiments, the present disclosure provides methods, solutions, and reaction mixtures comprising a first detection conjugate, a second detection conjugate, CHAPS, BSA, gelatin, PEG, EDTA, MgCl2, a Biolipidure® reagent, or any combination thereof.

In some embodiments, the optical signal is reflectance, an absorbance spectrum, scattering spectrum, or an emission spectrum. In some embodiments, the change in the optical signal comprises a spectral peak wavelength shift and/or a total spectral profile shift. In some embodiments, the total spectral profile shift is a difference spectrum. In some embodiments, the methods provided herein provide detection of nanogram, picogram, or femtogram quantities of the target analyte.

In some embodiments, the methods provided herein are performed in a spectrophotometric cuvette, an analytical rotor, a microwell plate, a clinical analyzer, a flow chamber, on the tip of an optical fiber, or in a transparent gel.

In one aspect, the present disclosure provides a reaction mixture comprising at least one binding partner-nanostructure conjugate, wherein the nanostructures comprise a plurality of protrusions and wherein the average diameter of the nanostructures is at least about 50 nm, or at least about 70 nm, or at least about 90 nm, or at least about 120 nm. In another aspect, present disclosure provides a reaction mixture comprising at least one binding partner-nanostructure conjugate, wherein the nanostructures are spherical nanostructures. In embodiments, the reaction mixture further comprises a zwitterionic detergent. In some embodiments, the zwitterionic detergent is selected from the group consisting of 3-((3-Cholamidopropyl) dimethylammino)-1-propanesulfonate (CHAPS), and a sulfobetaine detergent. In some embodiments, the CHAPS is present at a concentration of about 0.1% to about 1%. In further embodiments, the CHAPS is present at a concentration of about 0.5%.

In some embodiments, the binding partner is a biological macromolecule. In further embodiments, the biological macromolecule is selected from an antibody or a fragment thereof, an antigen, a receptor, a ligand, a polynucleotide, an aptamer, a polypeptide, a polysaccharide, a lipopolysaccharide, a glycopeptide, a lipoprotein, or a nucleoprotein. In some embodiments, the methods and compositions provided herein comprise a first detection conjugate and a second detection conjugate, wherein one of the binding partners of the detection conjugate is an antibody. In further embodiments, the first and second detection conjugates both comprise binding partners that are antibodies. In some embodiments, the antibodies conjugated to the first and second conjugates bind to different epitopes on the same target analyte. In some embodiments, the first and second antibodies or first and second conjugates bind to two different non-overlapping epitopes on the target analyte. In other embodiments, the first and second antibodies or first and second conjugates bind to two different antigens. In some embodiments, the two different antigens are two interacting molecules. In some embodiments, the interacting molecules are two macro-molecules, including but not limited to, a receptor and its ligand (e.g., a protein hormone and its binding receptor), a DNA binding transcription factor and another transcription factor and/or DNA, etc.

In some embodiments, the target analyte is selected from a protein, enzyme, antigen, antibody, peptide, nucleic acid, hormone, glycoprotein, polysaccharide, toxin, virus, virus particle, drug molecule, hapten, and a chemical. In further embodiments, the target analyte is a pathogenic antigen or antibody to a pathogenic antigen. In further embodiments, the pathogenic antigen is a viral antigen. In further embodiments, the viral antigen is from a virus selected from feline leukemia virus, canine parvovirus, foot and mouth virus, influenza virus, hepatitis a virus, hepatitis b, hepatitis c virus, HIV virus, human papilloma virus, Epstein Barr virus, and rabies virus. In other embodiments, the pathogenic antigen is a bacterial antigen. In further embodiments, the bacterial antigen is selected from *Ehrlichia, Borrelia, Anaplasma, Salmonella, Bacillus*, and *Rickettsia*. In yet further embodiments, the bacterial antigen is selected from *Ehrlichia canis, Ehrlichia chaffeensis, Ehrlichia ewingii, Borrelia burgdorferi, Anaplasma platys, Anaplasma phagocytophilum, Salmonella enterica, Bacillus anthracis*, and *Rickettsia rickettsii*.

In other embodiments, the pathogenic antigen is a fungal antigen or a parasitic antigen. In further embodiments, the fungal antigen or parasitic antigen is selected from canine heartworm, *Giardia lamblia, Plasmodium falciparum, African trypanosomiasis*, and *Trypanosoma brucei*.

In some embodiments, the mixture of the sample with the first and second detection conjugates provided herein is conducted in the presence of a blocking agent. In further embodiments, the blocking agent is selected from bovine serum albumin (BSA), casein, gelatin, ovalbumin, and gamma-globulins. In some embodiments, the blocking agent is BSA present at a concentration of about 1% to about 5% w/v.

In one aspect, the present disclosure provides methods for preparing a conjugate comprising a binding partner and anisotropic metallic nanostructure suitable for detecting changes in optical signal based on the presence of a target analyte, wherein the anisotropic metallic nanostructure comprises a plurality of protrusions (spikes) and wherein the diameter of the metallic nanostructure is at least about 50 nm. In other embodiments, the present disclosure provides methods for preparing a conjugate comprising a binding partner and metallic nanostructures suitable for detecting changes in optical signal based on the presence of a target analyte, wherein the metallic nanostructure is a spherical nanostructure. In embodiments, the method comprises mixing a solution comprising the metallic nanostructures with a solution comprising the binding partner to form a binding partner-nanostructure conjugate; blocking the conjugate with a blocking reagent provided herein (e.g., BSA and/or gelatin and/or PEG and/or a Biolipidure® reagent), with or without the presence of a viscosity enhancer and/or one or more Hofmeister series salt and/or EDTA and/or EGTA; (c) centrifuging the conjugate; and (d) resuspending the conjugates in a diluent comprising buffer such as phosphate buffered saline (PBS) or Tris buffered saline (TBS) or borate buffer, a blocking agent provided herein (e.g., BSA and/or gelatin and/or PEG), and CHAPS. In some embodiments, the binding partner is an antibody. In further embodiments, the antibody is an antibody containing hydrophobic regions.

In some embodiments, the metallic nanostructures and/or solution comprising the binding partner further comprises a viscosity enhancer. In some embodiments, the viscosity enhancer is selected from trehalose, maltodextrin, dextran, sucrose, sorbitol, mannitol, polyvinylpyrrolidone (PVP), and polyvinyl alcohol (PVA). In some embodiments, the viscosity enhancer is dextran. In some embodiments, the viscosity enhancer is methylcellulose.

In some embodiments, the centrifugation step of the method for preparing a conjugate provided herein comprises centrifugation at about 2000 g or more. In further embodiments, the method comprises centrifugation at about 5000 g or more. In further embodiments, the method comprises centrifugation at about 10,000 g or more. In further embodiments, the method comprises centrifugation at about 50,000 g or more. In further embodiments, the method comprises centrifugation at about 75,000 g or more. In further embodiments, the method comprises centrifugation at about 100,000 g or more.

In some embodiments, the present disclosure provides a lyophilization step following resuspension of the conjugates. In further embodiments, the lyophilization step comprises dispensing the conjugates in liquid nitrogen, freeze-drying using vacuum and temperature cycles.

BRIEF DESCRIPTION OF THE DRAWINGS

FIG. 22B shows the nonspecific adsorption of only 1002, 1201, 1202, 205, 206, and BSA.

FIG. 25 provides a schematic of the Hofmeister series salts (Zhang Y, Cremer PS, "Interactions between macromolecules and ions: The Hofmeister series" *Curr Opin Chem Biol.* 2006 December; 10(6):658-63).

DETAILED DESCRIPTION OF THE INVENTION

Figure 1:
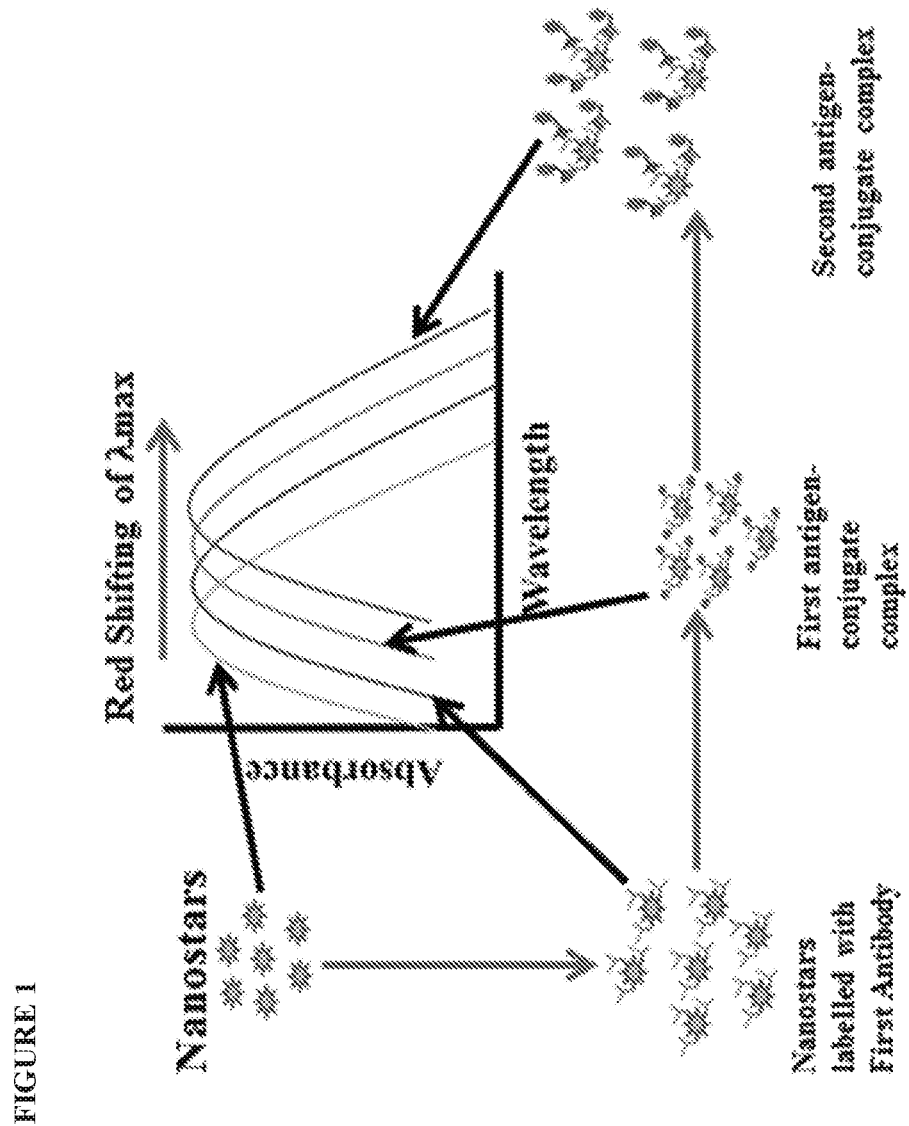
FIG. 1. Illustrates the principle of the LSPR immunoassay described herein. The metallic nanoparticle comprising a plurality of spikes by itself exhibits an optical spectrum. Slight changes at the surface of the nanoparticle due to first primary binding and subsequent secondary binding cause progressive changes in the characteristics of the light interacting with the nanoparticle-binding partner conjugates. Such changes can be recorded by a suitable spectrometer and provide qualitative as well as quantitative information.

The present invention is based, in part, on the discovery that significant amplification in LSPR-based assays can be achieved with anisotropic metallic nanostructure-labeled binding partners. Thus, the present invention provides analyte detection methods utilizing a plurality of detection conjugates comprising anisotropic metallic nanostructures coupled to biomolecules. The metallic nanostructures provided herein, in some embodiments, are multibranched, anisotropic nanoparticles that comprise a plurality of protrusions on the surface. The nanostructures comprising a plurality of protrusions on the surface as provided herein are also at least about 50 nm in diameter. In some embodiments, the metallic nanostructures provided herein are spherical or non-spherical metallic nanostructures.

The present invention overcomes problems of current immunoassays, ligand-receptor binding assays, nucleic acid-protein binding assays or other specific binding partner assays that generally require multiple steps and sophisticated equipment to perform such steps. The lack of sensitivity and the complexity involved in performing such heterogeneous assays arises from the specific need to separate labeled from unlabeled specific binding partners. The present invention overcomes such limitations by performing all steps involved in the assay in a homogenous format wherein the separation of reacted and unreacted assay components is unnecessary as the binding events change LSPR characteristics that are measured in real time by any of the spectroscopic techniques used by those of ordinary skill in spectroscopy. Separation free, one pot assays of the present invention use refractive index sensing, plasmon coupling and related effects to provide amplification of the final LSPR modulated signals. Moreover, the provided methods and metallic nanostructures are capable of improved detection. Surprisingly, the provided methods and metallic nanostructures are capable of improved detection and minimized non-specific binding (referred to herein as "NSB"). The present disclosure provides anisotropic nanostructure-antibody conjugates, and methods of making the same, that provide unexpectedly high sensitivity of detection of analytes. The present disclosure provides anisotropic nanostructure-antibody conjugates, and methods of making the same, that provide the unexpectedly high sensitivity of detection of analytes while providing unexpectedly low levels of NSB. In one aspect, the nanostructures comprise a plurality of protrusions. In some embodiments, the sensitive detection achieved with such star-shaped nanostructures is unexpected because it was well known in the art that metallic nanoparticles in the shape of a rod are better sensors of refractive index compared to round, spherical, or other nanostructures. Furthermore, the superior effects of anisotropic nanostructure with spherical cores and multiple spikes, provided herein, are surprising considering that the literature reports suggest better sensitivity with nanorods rather than the star-shaped structures described here. In other embodiments, the nanostructures are star-shaped or spherical, and the sensitivity and low levels of NSB provided herein is achieved by the conjugation methods provided herein.

As will be apparent to one of ordinary skill in the art, the present invention may be applied to the detection of a variety of antigenic analytes, such as those associated with infectious diseases in both humans and animals, e.g., antigens associated with infectious diseases and antibodies generated in response thereto. Beyond the detection of antigens and antibodies, the techniques described herein may also be used for performing assays involving specific binding partners such as ligands and receptors, and transcription factors and their associated DNA binding elements. Moreover, RNA-RNA, RNA-DNA, DNA-DNA or protein-nucleic acid interactions may be detected using appropriate conjugates of anisotropic metallic nanoparticles with specific binding partners.

As provided herein, the present invention describes the use of metallic nanoparticles in solution (as opposed to being attached to a surface via chemical or physical deposition) to determine the binding of specific binding partners in a qualitative or quantitative manner. The changes in the characteristics of light interacting with the regions containing unbound and bound partners attached to metallic nanoparticles can be measured, allowing for both qualitative and quantitative interactions between the specific binding partners to be determined by suitable detectors.

In a first aspect, the present application provides methods of detecting a target analyte in a sample. In some embodiments, the methods comprise mixing the sample with a plurality of detection conjugates that comprise anisotropic metallic nanostructures coupled to binding partners. In some embodiments, the nanostructures include a plurality of protrusions, or spikes. In some embodiments, the nanostructures are at least 50 nm in diameter, inclusive of the protrusions. In other embodiments, the nanostructures are spherical. In some embodiments, the nanostructures are gold nanostructures. In one embodiment, the methods comprise a first detection conjugate and a second detection conjugate, wherein the first and second detection conjugates comprise metallic nanostructures coupled to binding partners that are capable of specifically binding to the target analyte if present in the sample to form a complex between the first detection conjugate, the analyte, and the second detection conjugate. For example, the conjugates comprise a first binding partner and a second binding partner that each bind to a different epitope on the same target analyte. In further embodiments, the methods comprise exposing the complex to a light source at a wavelength range within the ultraviolet-visible-infrared spectrum; and measuring an optical signal from the complex, wherein a change in the optical signal indicates the presence of the target analyte in the sample. In an exemplary embodiment, the metallic nanostructure in the first detection conjugate and/or the second detection conjugate is a gold metallic nanostructure. In another exemplary embodiment, the step of mixing occurs in the presence of a polymeric material selected from polyethylene glycol (PEG), polyvinylpyrrolidone, polyallylamine, polyethyleneimine, polylysine, polyacrylic acid, polyvinylalcohol, polyglutamic acid and polyaspartic acid. In a preferred embodiment, the polymeric material is PEG. In yet another exemplary embodiment, the step of mixing occurs in the presence of a polysaccharide or other viscosity enhancer. In some embodiments, the viscosity enhancer selected from trehalose, maltodextrin, sucrose, sorbitol, mannitol, polyvinylpyrrolidone (PVP), or polyvinyl alcohol (PVA). In some embodiments, the polysaccharide is selected from maltodextrin, trehalose, sucrose, corn syrup, and polyglucose. In a preferred embodiment, the polysaccharide is maltodextrin or trehalose. In yet another exemplary embodiment, the step of mixing occurs in the presence of a blocking agent. In some embodiments, the blocking agent is selected from bovine serum albumin (BSA), casein, gelatin, ovalbumin, and gamma-globulins. In a preferred embodiment, the blocking agent is BSA.

In some embodiments, the present disclosure provides methods and compositions that include blocking agents that have previously been used in assays such as lateral flow assays, but have not previously been used or contemplated for use in LSPR assays. For example, in some embodiments, the present disclosure provides methods and compositions for the LSPR assay described herein, wherein one or more Biolipidure® reagent is used as a blocking agent. Surprisingly, despite the fact that the effects on wavelength shift in an LSPR assay could not be predicted based on the use of such agents in non-LSPR assays (such as lateral flow assays and the like), the present inventors found that Biolipidure® reagents provide superior effects in the LSPR assays provided herein. Biolipidure® reagents are polymer agents that exhibit one or more of the following features: enhancement of sensitivity and accuracy of detection; suppression of non-specific adsorption; stabilization of antibodies and enzymes; and elimination of lot-to-lot variations. Biolipidure® reagents do not require biohazardous handling and, in some embodiments, are used by preparing a buffer solution with Biolipidure® (e.g., about 0.1 wt %, about 0.25 wt %, about 0.5 wt %, about 0.75 wt %, about 1 wt %, about 1.25 wt %, about 1.5 wt %, about 2 wt %, about 5 wt %, or more), and dissolving the sample to be tested in the buffer. In particular embodiments, the Biolipidure® reagent is used at a concentration of 1 wt %.

In various embodiments described herein, the methods of the present invention can be configured in a sandwich assay format, a direct assay format, an indirect assay format, as well competitive and secondary labelling formats.

In some embodiments, the detection methods are sandwich assays. In such embodiments, the detection conjugates comprise the anisotropic metallic nanostructures provided herein, coupled to binding partners that are capable of specifically binding to the target analyte if present in the sample. For instance, in one embodiment, the method in a sandwich assay format comprises a first detection conjugate and a second detection conjugate wherein the first and second detection conjugates comprise spherical metallic nanostructures and/or metallic nanostructures having a plurality of protrusions, wherein the nanostructures are coupled to binding partners that are capable of specifically binding to the target analyte if present in the sample to form a complex between the first detection conjugate, the analyte, and the second detection conjugate. In an exemplary embodiment, the metallic nanostructure in the first detection conjugate and/or the second detection conjugate is anisotropic gold metallic nanostructure. The complex is exposed to a light source and an optical signal is measured, wherein a change in the optical signal indicates the presence of analyte in the sample. By way of illustration, when a sample containing the target analyte is mixed with the first and second detection conjugates, the target analyte binds to the binding partners in the detection conjugates to form a complex between the first detection conjugate, the analyte, and the second detection conjugate. This complex formation brings the metallic nanostructures in the detection conjugates in close proximity to each other, i.e., plasmon-plasmon coupling. The amount of light that is absorbed, scattered, or transmitted by the metallic nanostructures is affected by the proximity of the metallic nanostructures in the complex and thus produces an enhanced shift in the peak absorption wavelength, which indicates the presence of the target analyte in the sample.

In other embodiments, the detection methods are competitive assays. In such embodiments, the first detection conjugate comprises metallic nanostructures coupled to the target analyte of interest. As in the sandwich assay method, the second detection conjugate is capable of specifically binding to the target analyte. In this type of assay, the first detection conjugate will bind to the second detection conjugate initially. If a sample containing a target analyte is mixed with these initial complexes, the unlabeled or free target analyte in the sample will compete with the first detection conjugate for binding to the second detection conjugate. The change in optical signal in this type of assay will result from the displacement of the metallic nanostructures in the first detection conjugate from the second detection conjugate, which will proportionately reduce the wavelength shift in the peak absorption wavelength.

As noted above, the methods of the invention may utilize a plurality of detection conjugates. Detection conjugates comprise spherical metallic nanostructures or metallic nanostructures having a plurality of protrusions and coupled to binding partners capable of specifically binding to a target analyte or another detection conjugate depending on the assay configuration. For example, in embodiments in which the method is configured in a sandwich assay format, the detection conjugates comprise metallic nanostructures coupled or conjugated to binding partners that are capable of specifically binding a target analyte. In other embodiments in which the method is configured in a direct competitive assay format, at least one of the detection conjugates comprises the metallic nanostructures coupled or conjugated to target analytes.

In some embodiments, the detection conjugates comprise binding partners that are capable of specifically binding to a target analyte. As used herein, "specific binding" refers to binding to a target molecule with high affinity, e.g., an affinity of at least $10^{-6}$ M. In some embodiments, the binding partners are haptens and other small molecules, drugs, hormones, biological macromolecules including, but not limited to, antibodies or fragments thereof (e.g., Fv, Fab, $(Fab)_2$, single chain, CDR etc.), antigens, receptors, ligands, polynucleotides, aptamers, polypeptides, polysaccharides, lipopolysaccharides, glycopeptides, lipoproteins, or nucleoproteins. In certain embodiments, the binding partners are antibodies. In other embodiments, the binding partners are antigens.

In some embodiments, the detection conjugates, e.g., a first detection conjugate and a second detection conjugate, comprise binding partners that are the same type of molecule, but preferably bind to the target analyte at locations distinct from the other. By way of example, a first detection conjugate and a second detection conjugate can both be antibodies that recognize a target analyte, but the epitope to which the first detection conjugate binds the target analyte is separate from and ideally non-overlapping with the epitope to which the second detection conjugate binds the target analyte. Thus, in certain embodiments, the first detection conjugate comprises an antibody that recognizes a first epitope of a target analyte and the second detection conjugate comprises a different antibody that recognizes a second epitope of a target analyte. In various embodiments described herein, the first detection conjugate may comprise a monoclonal antibody that recognizes a first epitope of a target analyte. In further embodiments, the second detection conjugate may comprise a monoclonal antibody that recognizes a second epitope of a target analyte that is separate from and ideally non-overlapping with the epitope that is recognized by the first detection conjugate. Alternatively, the first detection conjugate and/or the second detection conjugate may comprise a polyclonal antibody. For instance, the first detection conjugate may comprise a polyclonal antibody while the second detection conjugate comprises a monoclonal antibody. In some embodiments, the first detection conjugate comprises a polyclonal antibody and the second detection conjugate comprises a polyclonal antibody.

The metallic nanostructures in the detection conjugates can be composed of a noble metal or composite thereof. In some embodiments, the metallic nanostructures in the detection conjugates may be composed of a transition metal or composite thereof. In some embodiments, the metallic nanostructures in the detection conjugates may comprise an alkali metal or lanthanide in combination with a noble or transition metal. In certain embodiments, metallic nanostructures in the detection conjugates comprise a metal selected from gold, silver, copper, platinum, palladium, ruthenium, rhodium, osmium, iridium, titanium, chromium, cadmium, zinc, iron, cobalt, nickel, and composites thereof. In one embodiment, the metallic nanostructures are gold nanostructures. In another embodiment, the metallic nanostructures are silver nanostructures. In still another embodiment, the metallic nanostructures in the detection conjugates are composite metallic nanostructures. "Composite metallic nanostructures" refers to nanostructures that comprise at least two noble metals, transition metals, alkali metals, or lanthanides. The two or more metals may be mixed together, as in an alloy, or the two or more metals may be present in separate portions of the nanostructure. For example, one metal may form the core of the nanostructure, whereas the second metal forms an outer shell or coating of the nanostructure. In some embodiments, the composite metallic nanostructures comprise at least two metals selected from gold, silver, copper, platinum, palladium, ruthenium, rhodium, osmium, iridium, titanium, chromium, cadmium, zinc, iron, cobalt, and nickel. In other embodiments, the composite metallic nanostructures comprise at least two metals selected from gold, silver, copper, platinum, palladium, cadmium, iron, nickel, and zinc. In one particular embodiment, the composite metallic nanostructures comprise gold and silver. In another embodiment, the composite metallic nanostructures comprise gold and copper. In yet another embodiment, the composite metallic nanostructures comprise silver and copper. In some embodiments, the composite metallic nanostructures used in the methods of the invention comprise a core of a first metal and a coating of a second metal. For example, the composite metallic nanostructures may comprise a silver core and a gold coating. In other embodiments, the composite metallic nanostructures comprise a copper core and a gold coating. In another embodiment, the core is silver and the coating is copper. In some embodiments, each of the composite metallic nanostructures comprises a dielectric core (e.g. silicon dioxide, gold sulfide, titanium dioxide, silica, and polystyrene), a first coating of a first metal, and a second coating of a second metal. In some embodiments, the core comprising a first metal is dissolved following the coating process with a second metal to create a hollow structure comprised of the second metal. For instance, coating of a silver core with gold nanoparticles generates a gold shell around the silver core and the silver core is subsequently dissolved or degraded resulting in the formation of a hollow nanogold shell structure.

The nanostructures disclosed herein, in some embodiments, include a plurality of protrusions, such as spikes or cone-shaped protrusions. Thus, the nanostructures provided herein are multibranched nanoparticles. In some embodiments, the surface of the inner core of the nanostructures is essentially covered by the protrusions. The diameters of the nanostructures as recited herein includes the protrusions, i.e., the recited diameters are tip-to-tip of the protrusions covering the nanostructures.

In one aspect, the average diameter of the nanostructures provided herein having a plurality of protrusions or spikes is from about 50 nm to about 120 nm. The average diameter of the nanostructures is inclusive of the protrusions thereon. Thus, the average diameter is described herein as the tip-to-tip diameter in some embodiments. In some embodiments, the average diameter is about 50 nm, about 60 nm, about 70 nm, about 80 nm, about 90 nm, about 100 nm, about 110 nm, about 120 nm, or more. In some embodiments, the average diameter is about 70 nm. In other embodiments, the average diameter is about 90 nm. In some embodiments, the nanostructures include a mix of average diameters from about 50 nm to about 90 nm. In one aspect, the average diameter of the spherical nanostructures provided is from about 50 nm to about 120 nm. In some embodiments, the average diameter of the spherical nanostructures is about 50 nm, about 60 nm, about 70 nm, about 80 nm, about 90 nm, about 100 nm, about 110 nm, about 120 nm, or more.

In another aspect, the present disclosure provides reaction mixtures comprising the binding partner—nanostructure conjugates disclosed herein. In further embodiments, the reaction mixtures comprise one or more capping reagent and/or one or more zwitterionic detergent. In some embodiments, the capping agent is a zwitterionic detergent. For example, in some embodiments, the reaction mixture comprises CHAPS. The present inventors surprisingly found that the presence of CHAPS, a capping agent and a zwitterionic detergent, allowed the nanostructures provided herein, comprising a plurality of surface protrusions, to be effectively conjugated to binding partners such as antibodies. In addition, the presence of CHAPS allowed for faster centrifugation and shorter time periods for centrifugation. For example, the present inventors found that in the presence of CHAPS, centrifugation speeds that would normally cause the anisotropic nanoparticle antibody conjugates to fall apart (e.g., above 15,000 g or about 40,000 g) could be used to centrifuge the nanostructures provided herein. Thus, the presence of CHAPS allows for a more efficient generation of conjugates. Further, the presence of CHAPS allowed the facile resuspension of the antibody conjugates following centrifugation. In particular, conjugates comprising hydrophobic antibodies that otherwise cannot be resuspended following centrifugation are readily resuspended in the presence of CHAPS. Moreover, the presence of CHAPS detergent helps prevent nonspecific size/shape changes leading to aggregation. Particles, such as the nanostructures provided herein having a plurality of spikes, can fall out of solution. The present inventors found that surprisingly, even where the particles fall completely out of solution, the particles can be rescued by adding CHAPS. In some embodiments, the reaction mixtures comprise binding partner-nanostructure conjugates wherein the mixture comprises one or more capping agents or zwitterionic detergents selected from sulfobetaine series, a Triton series (x-100) detergent; a Tween series (Tween 20) detergent, a cationic detergent series such as CTAB, and an anionic detergent such as SDS.

Methods of conjugating molecules to the metallic nanostructures disclosed herein are also provided. Such methods include conjugation chemistries, such as those involving 1-Ethyl-3-[3-dimethylaminopropyl]carbodiimide hydrochloride (EDC), sulfo-NHS coupling, hydrophobic binding or thioether chemistry. In some embodiments, the binding partners or target analytes can be coupled to the metallic nanostructures through various chemical functionalities including thiol, amine, dithiol, acrylic phosphoramidite, azide, or alkynes. In some embodiments, the molecule can be coupled to the metallic nanostructure indirectly through a larger carrier molecule or protein. Such indirect coupling is particularly useful when the molecule is small, such as a hormone, a drug, and other small molecules less than 10 kD. Preferably, the carrier protein is not capable of specific interaction with the target analyte. In some embodiments, protein A or protein G or protein A/G may be conjugated or coupled to the nanoparticles.

In some embodiments, the methods for conjugating molecules to the metallic nanostructures provided herein comprising mixing a solution comprising the metallic nanostructures with a solution comprising the binding partner to form a binding partner-nanostructure conjugate; blocking the conjugate with BSA; (c) centrifuging the conjugate; and (d) resuspending the conjugates in a diluent comprising buffer such as PBS, a blocking agent such as BSA and CHAPS. In some embodiments, the binding partner is an antibody. In further embodiments, the antibody is an antibody containing hydrophobic regions. In some embodiments, the metallic nanostructure is adjusted to basic pH prior to titration of the antibody into the nanostructure. For example, in some embodiments, the nanostructure pH is adjusted to pH of about 8, about 8.5, about 8.8, or about 9.2. However, in some embodiments, the present inventors surprisingly found that, the pH of the solution comprising the nanostructure can be adjusted to a neutral or acidic pH (e.g., about 5.5, about 6, about 6.5, or about 7) and successfully form conjugates capable of sensitive antigen detection. In some embodiments, the neutral or acidic pH resulted in conjugates which were difficult to resuspend in standard conjugate diluents comprising BSA and phosphate buffer. Surprisingly such insoluble conjugates were rapidly dissolved in buffers containing CHAPS.

In some embodiments, the metal or metals employed in a first detection conjugate can be the same as the metal or metals from which the metallic nanostructures in the second detection conjugate are fabricated. For example, in one embodiment, the first detection conjugate comprises gold nanostructures and the second detection conjugate comprise gold nanostructures. In other embodiments, the metal employed in the first detection conjugate is different from the metal or metals used to create the metallic nanostructures in the second detection conjugate.

In some embodiments, the reaction environment may be adjusted with appropriate buffers, ionic strength, and other accelerants. In a preferred embodiment, the reaction environment comprises polyethylene glycol (PEG), which, as described herein, can enhance the strength of the LSPR signal and the rate at which the signal develops. Other similar polymeric materials may also be used, including, but not limited to, polyvinylpyrrolidone, poly allylamine, polyethyleneimine, polylysine, polyacrylic acid, polyvinylalcohol, and polyaspartic acid.

The present invention also provides analyte detection devices for utilizing the methods described herein to detect a target analyte in a sample. Suitable analyte detection devices may include, but are not limited to, a spectrophotometric cuvette, an analytical rotor, a microwell plate, or a flow chamber. As will be understood by the skilled artisan, the tip of an optical fiber or a transparent gel may also be employed to carry out the detection methods disclosed herein.

In certain embodiments, all components of the analyte detection devices described herein are contained within a centrifugal rotor or disc. For instance, a rotor or disc may contain one or more reaction chambers in which the plurality of detection conjugates is located. In some embodiments, the detection conjugates are present in the form of lyophilized compositions, such as lyophilized beads or pellets. In some embodiments, the analyte detection device comprises a rotor or disc having one or more reaction chambers, wherein each reaction chamber comprises a plurality of detection conjugates (e.g., a first detection conjugate and a second detection conjugate), wherein the detection conjugates are first and the second specific binding partners coupled to metallic nanoparticles. Such a device provides a one-step analyte detection assay whereby a test sample is contacted with the rotor or disc, and application of a centrifugal force to the rotor or disc delivers the test sample to the reaction chambers where the sample mixes with the first detection conjugate and the second detection conjugate. In embodiments in which the rotor or disc contains more than one reaction chamber, the detection conjugates can be selected such that a different analyte can be detected in each reaction chamber. These rotor-format detection devices can be configured in the sandwich assay format, the direct competitive format, or both if the rotors comprise multiple reaction chambers.

In some embodiments, direct competitive assays or sandwich assays may be performed in a centrifugal rotor, such as a rotor described in U.S. Pat. Nos. 5,061,381, 5,122,284, 5,186,844, 5,304,348, 5,457,053, and 5,693,233. In some embodiments, the present disclosure provides multiplex assays in which discs or rotors capable of multiplex analysis allow for separate detection via, for example, multiple cuvettes.

In some embodiments, the nanoparticle conjugates of the two pairing monoclonal antibodies or a polyclonal antibody mixture that binds to more than one epitope are added as lyophilized beads. The solution phase LSPR assay works both with monoclonal and polyclonal antibodies. In some embodiments, the present disclosure provides antibody pairs that allow highly sensitive detection in an LSPR assay. For example, in some embodiments, the antibody pair is anti-TSH antibody clones C1 and C6, which each bind to a different epitope of TSH. In other embodiments, the antibody pair is anti-TSH antibody close C1 and 5409. In some embodiments, the best signal to noise ratio is obtained with the gold conjugates prepared from anti-TSH close 5405 and 5409.

The present invention also includes kits comprising the analyte detection devices of the invention as disclosed herein. In one embodiment, the kit comprises a plurality of detection conjugates (e.g., a first detection conjugate and a second detection conjugate), wherein the detection conjugates are specific binding partners linked to the metallic nanostructures provided herein. In some embodiments, one or more of the detection conjugates may be lyophilized, for example, in the form of a pellet or bead. In one embodiment, all of the detection conjugates are lyophilized. In further embodiments, the kit may include one or more additional reagents. In some embodiments, one or more of the additional reagents is provided in lyophilized form. In some embodiments, the kit may comprise a blocking agent, a sugar, a polymeric accelerant material, sodium chloride, and/or combinations thereof. A "blocking agent" is an agent that prevents the association of proteins present in the sample with the detectable agent and/or analyte. Blocking agents are typically proteins themselves and may include, but are not limited to, bovine serum albumin (BSA), casein, gelatin, ovalbumin, gamma-globulins, and IgG from non-immunized animals. In some embodiments, the sugar is a polysaccharide. In one embodiment, the polysaccharide is selected from maltodextrin, corn syrup, and polyglucose. In a preferred embodiment, the polysaccharide is maltodextrin. In another embodiment, the sugar is trehalose. In some embodiments, the reagent kit may comprise maltodextrin and trehalose. In some embodiments, the polymeric accelerant material is PEG.

The kits of the invention may also include instructions for using the device to detect an analyte in a test sample, devices or tools for collecting biological samples, and/or extraction buffers for obtaining samples from solid materials, such as soil, food, and biological tissues.

As described herein, a test sample can be any type of liquid sample, including biological samples or extracts prepared from environmental or food samples. In one particular embodiment, the test sample is a biological sample. Biological samples include, but are not limited to, whole blood, plasma, serum, saliva, urine, pleural effusion, sweat, bile, cerebrospinal fluid, fecal material, vaginal fluids, sperm, ocular lens fluid, mucous, synovial fluid, peritoneal fluid, amniotic fluid, biopsy tissues, saliva, and cellular lysates. The biological sample can be obtained from a human subject or animal subject suspected of having a disease condition, such as cancer, infectious diseases (e.g., viral-, bacterial-, parasitic- or fungal-infections), cardiovascular disease, metabolic disease, autoimmune disease etc. The biological sample can also be obtained from a healthy subject (e.g. human or animal) undergoing a routine medical check-up.

In some embodiments of the methods, the test sample is mixed with a first detection conjugate and the mixture is subsequently brought into contact with the second detection conjugate. In certain embodiments, the sample, the first detection conjugate, and the second detection conjugate are brought into contact at the same time. For instance, contact of the sample with both reagents simultaneously may occur in the rotor-format detection devices described herein.

As noted above, the present application relates, in some embodiments, to the use of metallic nanostructures conjugated to binding partners, wherein the nanostructures have a plurality of protrusions, such as spikes or cone-shaped protrusions, and wherein the nanostructures have an average diameter of about 50 nm or more. The present inventors have surprisingly found that the sensitivity of the solution-based assay is significantly enhanced with protrusion-laden nanostructures compared to the use of nanorods (which have a smooth rod-shaped surface), even though nanorods would have been expected to provide superior results because they are known to be the better sensors of refractive index changes. In fact, the present inventors surprisingly found that in the solution-based assays disclosed herein, the metallic nanostructure conjugates comprising nanostructures having a plurality of protrusions exhibited robust antigen detection whereas nanorod-conjugates were not capable of robust antigen detection. The present inventors have further found that the larger nanostructures comprising protrusions exhibit better sensitivity of detection relative to smaller nanostructures having the same protrusion features. For example, in some embodiments, the sensitivity of detection increases when the average diameter of the nanostructures used in the assay is increased from about 50 nm to about 70 nm. In further embodiments, the sensitivity of detection increases even more when the average diameter of the nanostructures used in the assay is increased from about 70 nm to about 90 nm.

In one embodiment, the solution comprises a polysaccharide at a final concentration of about 2% to about 20% wt/vol. In another embodiment, the solution comprises a polysaccharide at a final concentration of about 4% to about 15% wt/vol. In yet another embodiment, the solution comprises a polysaccharide at a final concentration of about 5% to about 10% wt/vol. In an exemplary embodiment, the solution comprises a polysaccharide at a final concentration of about 5%, 6%, 7%, 8%, 9%, 10%, 15%, 20%, 25%, 30%, 35%, 40%, 45%, 50%, 55%, 60% or more, inclusive of all values therebetween. In certain embodiments, trehalose may be used to prevent sedimentation of detection conjugates in analytical rotors. In certain embodiments, the trehalose concentration is about 10%, 15%, 20%, 25%, 30%, 35%, 40%, 45%, 50%, 55%, 60% or more, inclusive of all values therebetween In various embodiments described herein, the sensitivity of the assay may be improved when a polysaccharide is added to the solution as compared to an assay performed in a solution comprising an alternative sugar, e.g., sucrose, trehalose, maltodextrin, sorbitol, mannitol, or ficoll. In an exemplary embodiment, the polysaccharide is maltodextrin. In another exemplary embodiment, the polysaccharide is trehalose. In yet another exemplary embodiment, the polysaccharide is dextran.

In one embodiment, the solution comprises a blocking agent at a final concentration of about 0.1% to about 20% wt/vol. In another embodiment, the solution comprises a blocking agent at a final concentration of about 0.5% to about 10% wt/vol. In yet another embodiment, the solution comprises a blocking agent at a final concentration of about 1% to about 5% wt/vol. In an exemplary embodiment, the solution comprises a blocking agent at a final concentration of about 1%, 2%, 3%, 4%, or 5%, inclusive of all values therebetween. In various embodiments described herein, the sensitivity of the assay may be improved when a blocking agent is added to the solution as compared to an assay performed in the absence of a blocking agent. In some embodiments, the blocking agent is selected from bovine serum albumin, casein, gelatin, ovalbumin, and gamma-globulins. In an exemplary embodiment, the blocking agent is bovine serum albumin (BSA).

In some embodiments, the solution comprises one or more of maltodextrin, trehalose, PEG, a blocking agent (e.g. BSA), and/or sodium chloride. In exemplary embodiments, one or more of the solution components, e.g., maltodextrin, may be provided as a lyophilized bead or pellet that is suspended upon the addition of a liquid, e.g., water, saline solution, or a liquid biological sample. For instance, one or more of the solution components may be provided in a spectrophotometric cuvette or a reaction chamber of an analytical rotor as a bead that is suspended into the solution following the addition of a liquid.

In additional embodiments, the LSPR signal may be substantially increased by mixing the first and second detection conjugates with the analyte in the presence of a polymeric accelerant material selected from polyethylene glycol, polyvinylpyrrolidone, polyallylamine, polyethyleneimine, polylysine, polyacrylic acid, polyvinylalcohol, and polyaspartic acid. In an exemplary embodiment, the polymeric material is polyethylene glycol (PEG). In one embodiment, the reaction mixture comprises a polymeric material, e.g., PEG, at a final concentration of about 0.1 mg/mL to about 200 mg/mL. In another embodiment, the reaction mixture comprises a polymeric material, e.g., PEG, at a final concentration of about 0.2 mg/mL to about 100 mg/mL. In yet another embodiment, the reaction mixture comprises a polymeric material, e.g., PEG, at a final concentration of about 0.5 mg/mL to about 10 mg/mL. In yet another embodiment, the reaction mixture comprises a polymeric material, e.g., PEG, at a final concentration of about 2 mg/mL to about 8 mg/mL. In an exemplary embodiment, the reaction mixture comprises a polymeric material, e.g., PEG, at a final concentration of about 2, 3, 4, 5, 6, 7, or 8 mg/mL, inclusive of all values therebetween. In some embodiments, PEG of different molecular weight may be used, e.g., a smaller quantity of higher molecular weight PEG can be used for a substantial effect. In some embodiments, PEG concentrations required for assay enhancement vary with the molecular weight of the polymer.

The detection methods of the invention may be used to determine qualitative or quantitative amounts of a target analyte. Such methods are particularly useful for determining the approximate amount of a target analyte in a sample, which can be used inter alia to diagnose certain medical conditions or evaluate the efficacy of a drug therapy. In one embodiment, the quantity of a target analyte can be determined by establishing a standard curve for the particular analyte by measuring changes in optical signals from the metallic nanoparticles as described herein for samples with a known quantity of target analyte; determining the optical signal change for a test sample; and comparing the optical signal change for the test sample to the values obtained for the standard curve. In some embodiments, determining the quantity of a complex between a first reagent and a second reagent comprises comparing the absorbance ratio and/or reaction rate from a test sample to the absorbance ratio and/or reaction rate from one sample with a known quantity of complex, thereby determining the quantity of the complex in the test sample. The quantitative values obtained from test samples may be compared to pre-determined threshold values, wherein said pre-determined threshold values are indicative of either an abnormal or normal level of the target analyte.

The detection methods of the present invention provide a highly sensitive technique for detecting minute quantities of a target analyte in a sample. In some embodiments, amplification of surface plasmon resonance-based signals can be achieved with gold nanostructure conjugates such that nanogram quantities of target analyte can be detected in a sample. Thus, in one embodiment of the methods, the presence of nanogram quantities of a target analyte is detected. In some embodiments, plasmon resonance-based signals from detection conjugates comprising gold nanoparticles can be amplified using composite metallic nanostructure detection conjugates. Use of gold-coated silver nanostructures conjugated to an analyte-specific antibody may enable the detection of picogram quantities of the target analyte. Accordingly, in some embodiments of the methods, the presence of picogram quantities of the target analyte is detected. In other embodiments of the methods, the presence of femtogram quantities of the target analyte is detected. Greater sensitivities may be obtained by altering the composition and/or shape of the composite metallic nanostructures.

When incident light is applied to metallic nanostructures, conduction band electrons in the metal oscillate collectively at the same frequency of the incident electromagnetic wave. As a result of these resonance oscillations, the nanostructures strongly absorb and scatter light at a specific wavelength range. For metallic nanostructures comprising noble or transition metals, this wavelength range is in the ultraviolet-visible-infrared spectrum depending on the particular composition of the nanostructures. Thus, light sources for applying electromagnetic energy suitable for use in the methods of the invention can include any source that may apply a wavelength range within the ultraviolet-visible spectrum or ultraviolet-visible-infrared spectrum, including arc lamps and lasers. In some embodiments, the light source may be equipped with a monochromator so that specific wavelengths of light may be applied.

The optical properties of the metallic nanostructures depend on their size, shape, and composition. For instance, solid gold nanoparticles have an absorption peak wavelength ($\lambda_{max}$) from about 515 nm to about 560 nm depending on particle size. Gold spherical nanoparticles having a 30 nm diameter maximally absorb at about 520 nm with $\lambda_{max}$ shifting to longer wavelengths as particle diameter increases. Silver and copper particles have a $\lambda_{max}$ in the ultra-violet/blue or red region (e.g., from about 350 nm to about 500 nm) with increasing particle diameter causing a shift in $\lambda_{max}$ to longer wavelengths. Metallic nanorods have a transverse $\lambda_{max1}$ and a longitudinal $\lambda_{max2}$. Alloys of different metals typically exhibit absorption peaks in an intermediate range between the absorption peaks of the comprising metals. For example, nanostructures comprising a 50/50 alloy of gold and silver exhibit a $\lambda_{max}$ of about 480 nm with increasing amounts of gold causing a shift in the absorption peak to longer wavelengths. The sensitivity of the LSPR signals to changes in the local medium refractive index can be modified by changing the shape or geometry of the nanostructures. For instance, nonspherical particles (e.g. nanoprisms, nanorods, nanoshells, etc.) have increased LSPR sensitivities to changes in refractive index as compared to spheres. In some embodiments, the optical properties (e.g. absorption/scattering at particular wavelengths) are tailored to a particular application by varying the size, shape, or composition of the metallic nanostructures employed in the detection conjugates.

The interaction between the incident light and the metallic nanostructures can be monitored as reflected light or transmitted light. The amount of the incident light that is absorbed or scattered can be measured as an absorption spectrum in a reflection mode or the absorption spectrum in a transmission mode. In some embodiments, the optical signal measured from the metallic nanostructures can be an optical reflection, an absorbance spectrum, a scattering spectrum, and/or an emission spectrum.

The plasmon coupling between the metallic nanostructures in the detection conjugates resulting from complex formation between the binding partners and target analyte produces a change in the localized surface plasmon resonance spectrum of the metallic nanostructures. For instance, such changes can include an increased optical extinction, an increased optical reflection, and/or increased scattering and/or emission signal. In some embodiments, the change in optical signal indicative of the presence of the target analyte in the sample includes a shift, increase or decrease in optical scattering or a combination of these features. In certain embodiments, the change in optical signal indicative of the presence of the target analyte in the sample is a spectral peak wavelength shift. In certain other embodiments, the change in optical signal indicative of the presence of the target analyte in the sample is the wavelength shift at a position other than the peak. For instance, the change in optical signal indicative of the presence of the target analyte in the sample may be the midpoint spectral wavelength shift, the spectral wavelength shift at the wavelength's base, or the total spectral wavelength shift such as difference spectrum. In one embodiment, the wavelength shift in the optical spectral peak may be a red shift (e.g., a shift to a longer wavelength) within a 200 nm to 1200 nm spectral window. In another embodiment, the wavelength shift in the optical spectral peak may be a blue shift (e.g., a shift to a shorter wavelength) within a 200 nm to 1200 nm spectral window. The changes in optical signals can be measured at a particular time point following a set reaction period. Additionally or alternatively, changes in the optical signal over the reaction period (e.g. rate determinations) may be measured. Both types of measurements can be used for either qualitative or quantitative analysis of a target analyte.

Various means for measuring optical signals at different wavelengths and acquiring extinction, scattering, or emission spectra are known in the art. Any spectrophotometric or photometric instruments are suitable for use in the disclosed methods. Some non-limiting examples include plate readers, Cobas Fara analyzers, and Piccolo Xpress® and Vetscan analyzers (Abaxis, Inc., Union City, CA), optic fiber readers (e.g., LightPath™ S4 (LamdaGen, Menlo Park, CA)), SPR instruments (e.g., Biacore instruments available from GE Healthcare), centrifugal analyzers from Olympus, Hitachi etc.

The present invention also includes an assay complex comprising (i) a first detection conjugate that comprises the metallic nanostructures provided herein having a plurality of protrusions, coupled to a binding partner, (ii) a target analyte, and (iii) a second detection conjugate that comprises a metallic nanostructure according to the present disclosure, coupled to a binding partner, wherein the binding partner in the first detection conjugate is bound to a first epitope on the target analyte and the binding partner in the second detection conjugate is bound to a second epitope on the target analyte, thereby forming a complex comprising the first detection conjugate, target analyte, and the second detection conjugate. In some embodiments, the assay complex is contained within a cuvette adapted for use with a centrifugal rotor. In other embodiments, the assay complex is contained within a reaction chamber in a centrifugal rotor or disc.

Any type of target analyte can be detected using the methods, devices, and assay complexes of the present invention, particularly those that are significant in the diagnoses of diseases. A target analyte can include, but is not limited to, a protein, enzyme, antigen, antibody, peptide, nucleic acid (RNA, DNA, mRNA, miRNA), hormone, glycoprotein, polysaccharide, toxin, virus, virus particle, drug molecule, hapten, or chemical. In some embodiments, the target analyte is a marker or antigen associated with an infectious disease in humans and/or animals. In other embodiments, the target analyte is a marker or antigen associated with a particular physiological state or pathological condition.

In certain embodiments, the target analyte is a pathogenic antigen or antibody to a pathogenic antigen. For instance, the pathogenic antigen can be a viral antigen (e.g., feline leukemia virus, canine parvovirus, foot and mouth virus, influenza virus, hepatitis a, b, c virus, HIV virus, human papilloma virus, Epstein Barr virus, rabies virus, etc.), a bacterial antigen (e.g., *Ehrlichia, Borrelia, Anaplasma, Salmonella, Bacillus, Rickettsia*, etc.), a fungal antigen, or parasitic antigen (e.g., canine heartworm, *Giardia lamblia, Plasmodium falciparum, African trypanosomiasis, Trypanosoma brucei*, etc.). In specific embodiments, the bacterial antigen may be from *Ehrlichia canis, Ehrlichia chaffeensis, Ehrlichia ewingii, Borrelia burgdorferi, Anaplasma platys, Anaplasma phagocytophilum, Salmonella enterica, Bacillus anthracis,* and *Rickettsia rickettsii*. In other embodiments, the target analyte is a disease-related antigen or antibody to a disease-related antigen. Disease-related antigens include, but are not limited to, cancer-related antigens or markers (e.g., PSA, AFP, CA125, CA15-3, CA19-9, CEA, NY-ESO-1, MUC1, GM3, GD2, ERBB2, etc.), cardiovascular disease-related antigens or markers (e.g., troponin, C-reactive protein, brain natriuretic peptide, CKMB, fatty acid binding protein, etc.), metabolic-related antigens or markers (e.g., thyroid stimulating hormone, thyroxine, leptin, insulin), or autoimmune disease-related antigens or markers (e.g., autoantibodies). In certain embodiments, the target analyte is an inflammatory antigen or marker (e.g., C-reactive protein, MRP14, MRP8, 25F9, etc.). In other embodiments, the target analyte is a pregnancy-related antigen or marker (e.g., a fetal antigen, human chorionic gonadotropin).

In some embodiments, the present disclosure provides methods for synthesizing the nanostructure provided herein. In certain embodiments, silver/gold nanoparticles are synthesized in a single vessel by adding predetermined quantities of the following reagents in succession and with thorough mixing: (1) a surfactant (e.g., ionic [anionic, cationic or zwitterionic], or non-ionic) or capping agent such as 3-((3-Cholamidopropyl) dimethylammino)-1-propanesulfonate (CHAPS), SDS, Tween, Triton, or any of the sulfobetaine detergents, (2) gold chloride, (3) water, (4) silver nitrate, (5) trisodium citrate and finally (6) ascorbic acid is added to initiate the formation of nanoparticles. In other embodiments, the nanoparticles are synthesized in a single vessel by adding predetermined quantities of the following, in the following order: (1) a surfactant or capping agent such CHAPS, SDS, Tween, Triton, CTAB, or any of the sulfobetaine detergents, (2) gold chloride, (3) silver nitrate, (4) trisodium citrate, (5) water, and (6) a reductant. In some embodiments, the reductant is made up of CHAPS, ascorbic acid, trisodium citrate, and water. In further embodiments, the reductant is made up of about 200 mg CHAPS, about 4 g ascorbic acid, about 117.6 mg trisodum citrate, and about 15.68 g water. In some embodiments, about 1 mL of aqueous 1% (wt/wt) CHAPS is mixed sequentially with about 0.25 mL of 0.1M gold chloride, about 0.5 mL of 0.02M silver nitrate, about 0.05 mL of 1M trisodium citrate, about 6.2 mL of water, and about 2 mL of the reductant. Changing the concentrations of various active ingredients such as metallic salts, capping agents, reductants and pH of the solution results in different particle types (e.g., nanospheres, nanostars or nanorods) and different composition of the nanoparticles.

In some embodiments, nanostars are formed by mixing, in order, water, cetyltrimethylammonium bromide (CTAB), gold chloride, ascorbic acid, and pre-formed gold nanosphere seeds. In further embodiments, about 0.825 mL of water, about 0.1 mL of 20% CTAB, about 0.025 mL of 0.1 M gold chloride, about 0.05 mL of 1M ascorbic acid, and about 0.05 mL of gold nanosphere seeds are mixed in that order. The age of the seeds and the ratio of seeds to the metallic ions influence the geometry and thus the optical spectra of nanoparticles. Gold only nanostars are fabricated by reducing gold chloride using the reductant that is made up of about 200 mg CHAPS, about 4 g ascorbic acid, about 117.6 mg trisodum citrate, and about 15.68 g water. The size of nanostars formed is dictated by the gold chloride concentration. The gold nanostars prepared by this method can be purified by centrifugation and stored in water at 2-8° C.

The formation of nanomaterials using the methods provided herein is essentially complete within minutes but may be allowed to reach equilibrium overnight. The synthesis of nanoparticles can be monitored by spectroscopy and confirmed by scanning or transmission electron microscopy.

In some embodiments, the size and thus the optical properties can be changed by altering the concentration of the surfactant or capping agent, ascorbic acid, trisodium citrate, gold chloride and/or silver nitrate. The size of nanostars synthesized increases with increasing silver content up to a certain point and then it decreases. These changes are reflected in the LSPR peak of the synthesized nanostars as the peak red-shifts at increasing silver/gold ratio but then starts to blue shift at molar ratios of Gold:Silver:5:2. The final concentrations of the chosen detergent in the reaction mixture can be varied from 0.05-5% with the smaller particles predominating at higher concentrations of the detergent. Increasing the concentrations of ascorbic acid produces smaller nanostars with the final concentration of ascorbic acid varying from 0.05 to 0.2M. Similarly, increasing concentration of trisodium citrate from 10 mM to 100 mM decreases the nanostar sizes.

In some embodiments, gold-silver nanoalloys may be synthesized under alkaline reduction conditions by mixing CTAB (e.g., CTAB dissolved in alcohol) with gold chloride and silver nitrate. In some embodiments, nanoalloy formation may be induced by mixing, in order, water, CTAB, gold chloride (0.5 mM to 5 mM), silver nitrate (20% to 80% of gold), ascorbic acid (10 mM to 200 mM) or a reductant containing ascorbic acid, trisodium citrate and CHAPS, and NaOH (50% to 200% of ascorbic acid). In further embodiments, nanoalloys are formed by mixing about 0.825 ml of water, about 0.1 ml of 20% CTAB prepared in isopropanol, about 0.025 ml of 0.1M gold chloride, about 0.005-0.025 ml of 0.1M silver nitrate, about 0.05 ml of 1M ascorbic acid, and about 0.05 ml of 1M NaOH. The concentrations of CTAB can be varied from 0.05M to 0.2M with lower concentrations favoring higher content of nanostars synthesized. Acidic pH favors formation of nanorods and higher aspect ratios are obtained at decreasing pH.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

All patent and non-patent documents referenced throughout this disclosure are incorporated by reference herein in their entirety for all purposes.

EXAMPLES

Example 1. Titration of Antibody Clones for Conjugation to Nanostructures

Studies were conducted to identify a protocol for conjugating nanostructures having a plurality of spikes to exemplary antibodies. First, titration experiments were conducted to titrate anti-TSH clone C1 into the nanostructures in order to determine the antibody quantity required for optimal conjugation.

Figure 2:
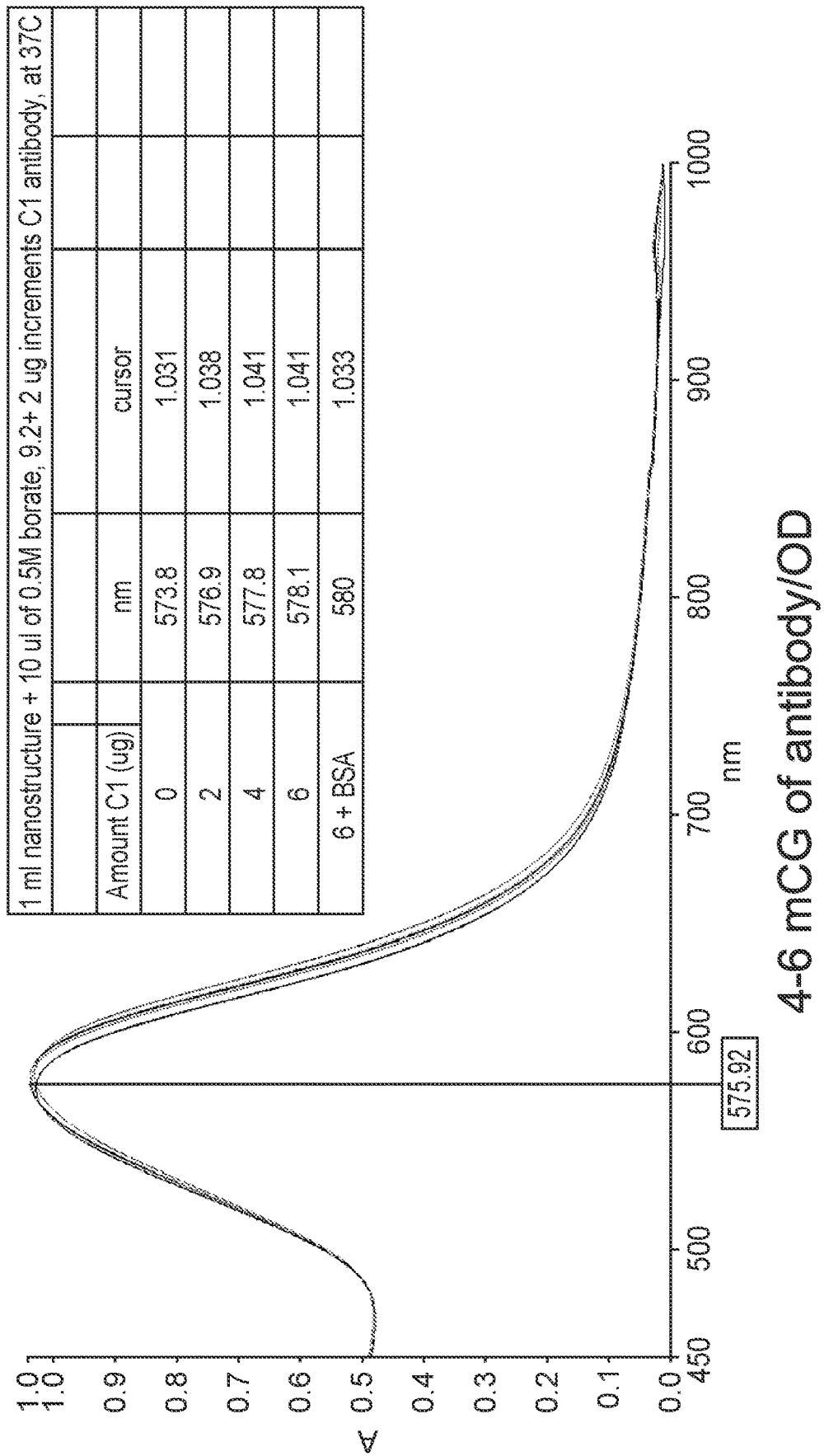
FIG. 2. Shows the titration of an anti-TSH antibody C1 into nanostructures comprising a plurality of protrusions to form antibody-nanostructure conjugates.

The reaction was setup in a 1 ml cuvette placed in Lambda950 spectrophotometer. One ml of the nanostructures was placed into the cuvette after pH adjustment to 9.2 with 10 microliters of 0.5M borate, pH 9.2. The spectrum was recorded which showed λmax at 573.8 nm. The binding of antibody C1 was determined by observing peak shift upon successive additions of 2 µg of the antibody. The equivalence point was reached at about 6-8 microgram antibody per OD unit. Finally 10 microliters of 20% BSA was added to block nonspecific binding events. This resulted in an additional 2 nm shift in λmax. The results are provided in FIG. 2.

Figure 3:
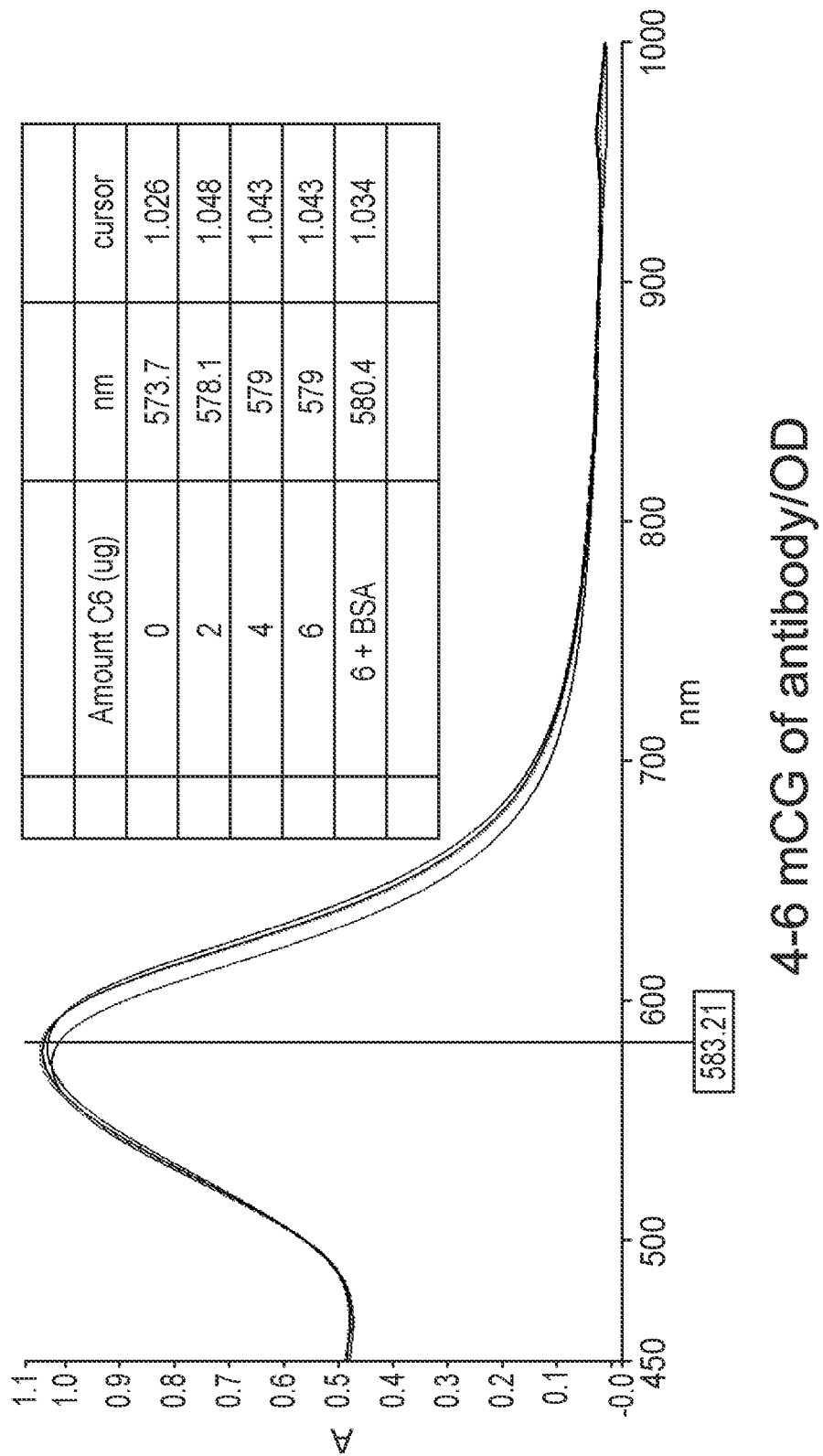
FIG. 3. Shows the titration of anti-TSH antibody C6 into nanostructures comprising a plurality of protrusions to form antibody-nanostructure conjugates.

Similarly, titration experiments were conducted to determine the antibody quantity required for conjugation of C6 (specific for a different epitope of TSH) antibodies. As for the C1 antibodies, the reaction was setup in a 1 ml cuvette placed in Lambda950 spectrophotometer. One ml of the nanostructures having a plurality of spikes was placed into the cuvette after pH adjustment to 9.2 with 10 microliters of 0.5M borate, pH 9.2. The spectrum was recorded which showed Lmax ($\lambda_{max}$) at 573.7 nm. The binding of antibody C6 was determined by observing peak shift upon successive additions of 2 µg of the antibody. The equivalence point was reached at about 6 microgram antibody per OD unit. Finally, 10 microliters of 20% BSA was added. This resulted in an additional 1.4 nm shift in λmax. The results are provided in FIG. 3.

Figure 4:
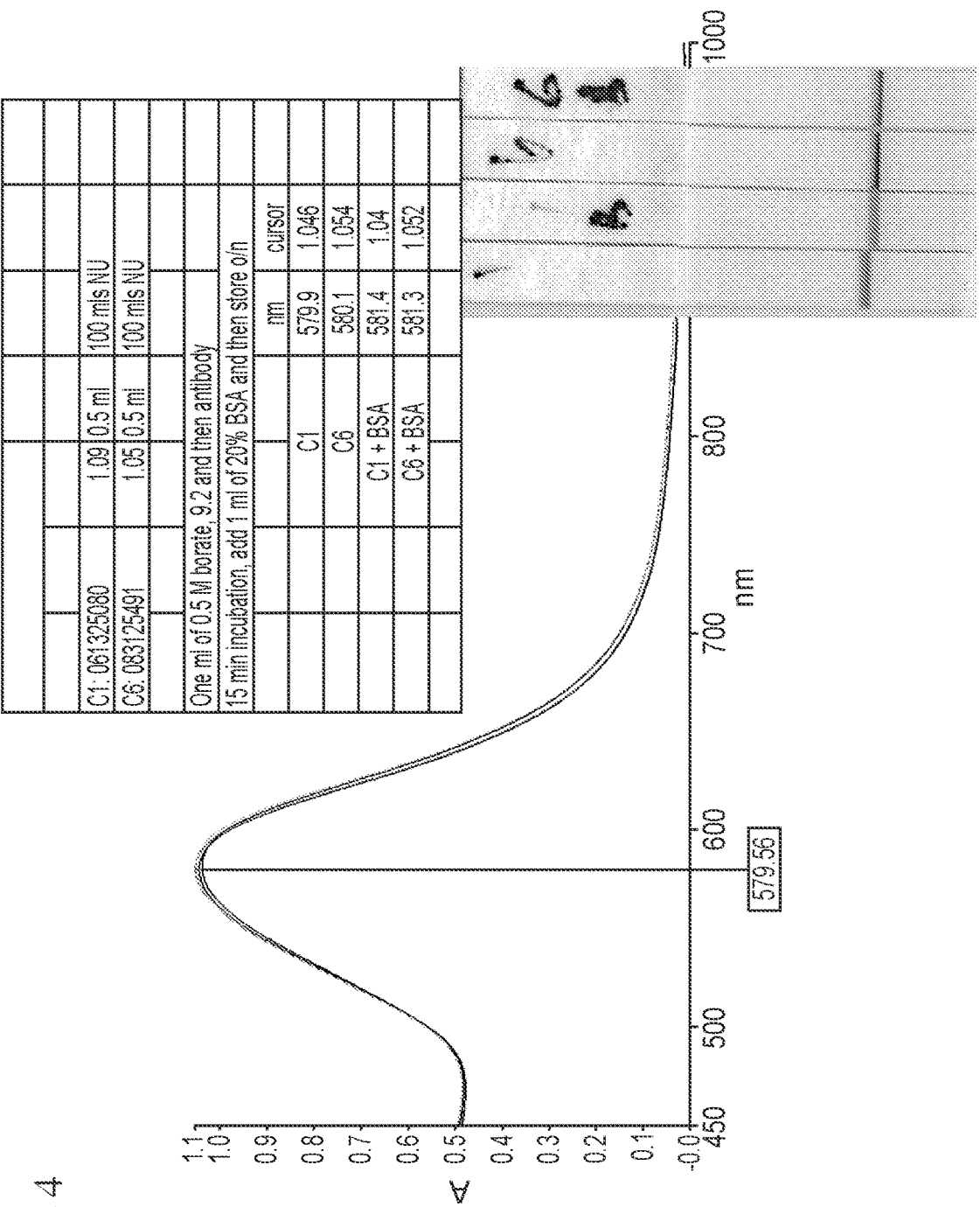
FIG. 4. Shows the large scale (100 ml nanostructures) titration of antibodies C1 and C6 into nanostructures comprising a plurality of protrusions to form C1 antibody- or C6 antibody-nanostructure conjugates. The inset shows strips striped with Protein A which have been dipped into the conjugate solutions with or without BSA blocking.

Next, to determine the scalability of conjugation, large scale (100 ml) conjugation of C1 and C6 antibodies to the nanostructures was conducted. The results are provided in FIG. 4. In this preparation, ~0.5 mg of C1 and of C6 were separately added to two vessels each containing 100 mls of nanostructure solutions pre-adjusted to pH 9.2 with rapid stirring. The conjugate solutions thus produced were tested for antibody binding before and after blocking with BSA. The strips striped with 0.5 mg/ml Protein A were dipped into the conjugate solutions diluted with a phosphate buffered BSA and Tween solution. The resulting lines (1 and 6) indicated that C1 or C6 were bound to nanostructures and the antibodies stayed bound after BSA blocking (1B and 6B).

Figure 5:
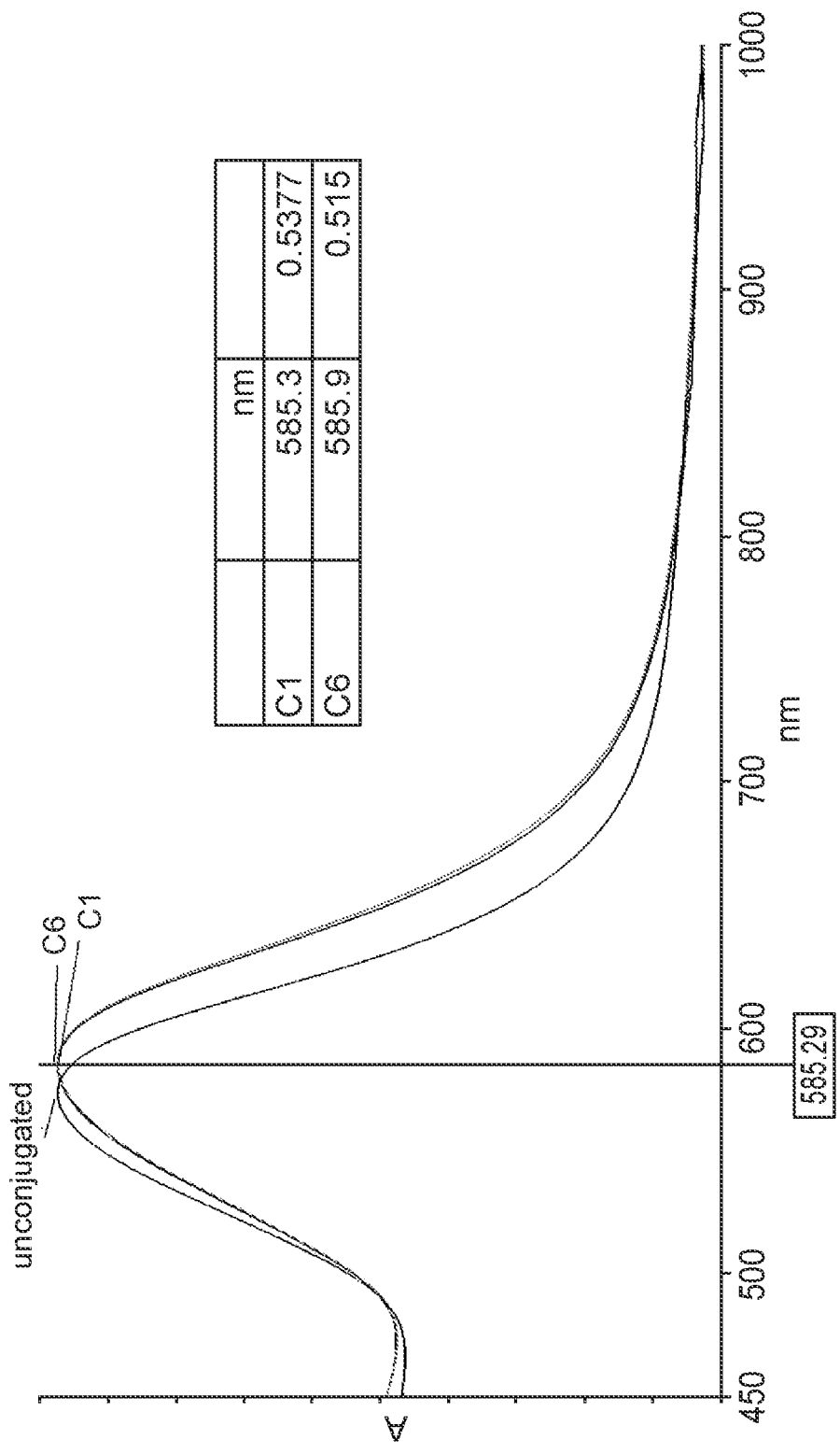
FIG. 5. Shows peak shift of unconjugated (573.8 nm) and C1 (shift to 585.3 nm) or C6 (shift to 585.9 nm) nanostructures.

C1 and C6 conjugates were recovered by centrifugation, washed once with the conjugate diluent and re-centrifuged. The sediments containing conjugates were easily dissolved in a conjugate storage solution containing PBS/BSA/CHAPS. Dilutions of the final conjugates were made in water and compared. The original unconjugated nanostructures had peak at 573.8 nm which red-shifted to 585-586 nm in the blocked conjugates. The shift is shown in FIG. 5. The final conjugate solutions may be stored at 2-8 C until use.

Example 2. Conjugation of Nanostructures to Antibodies Via Adsorptive Conjugation Protocol To generate nanostructure conjugates, nanostructures having a plurality of protrusions and an average diameter of 50 nm (lamdamax at 575 nm-1.0 OD/mL) were adjusted to pH 8.8 with 0.1M borate. C1 or C6 antibodies (about 33 picomoles per OD nanostructure) were titrated in and mixed well for 15 minutes. 2 mg BSA per ml was added and mixed for a further 15 minutes. Nanostructure/C1 or /C6 mixtures were centrifuged for 15,000 g for 10 minutes; supernatant was removed; and the conjugates were resuspended in conjugate diluent CG-1P, comprising PBS/BSA and CHAPS. CHAPS was particularly important to the resuspension of C6 antibodies, which are hydrophobic. Moreover, the CHAPS detergent helped prevent nonspecific size/shape changes leading to aggregation.

Figure 6:
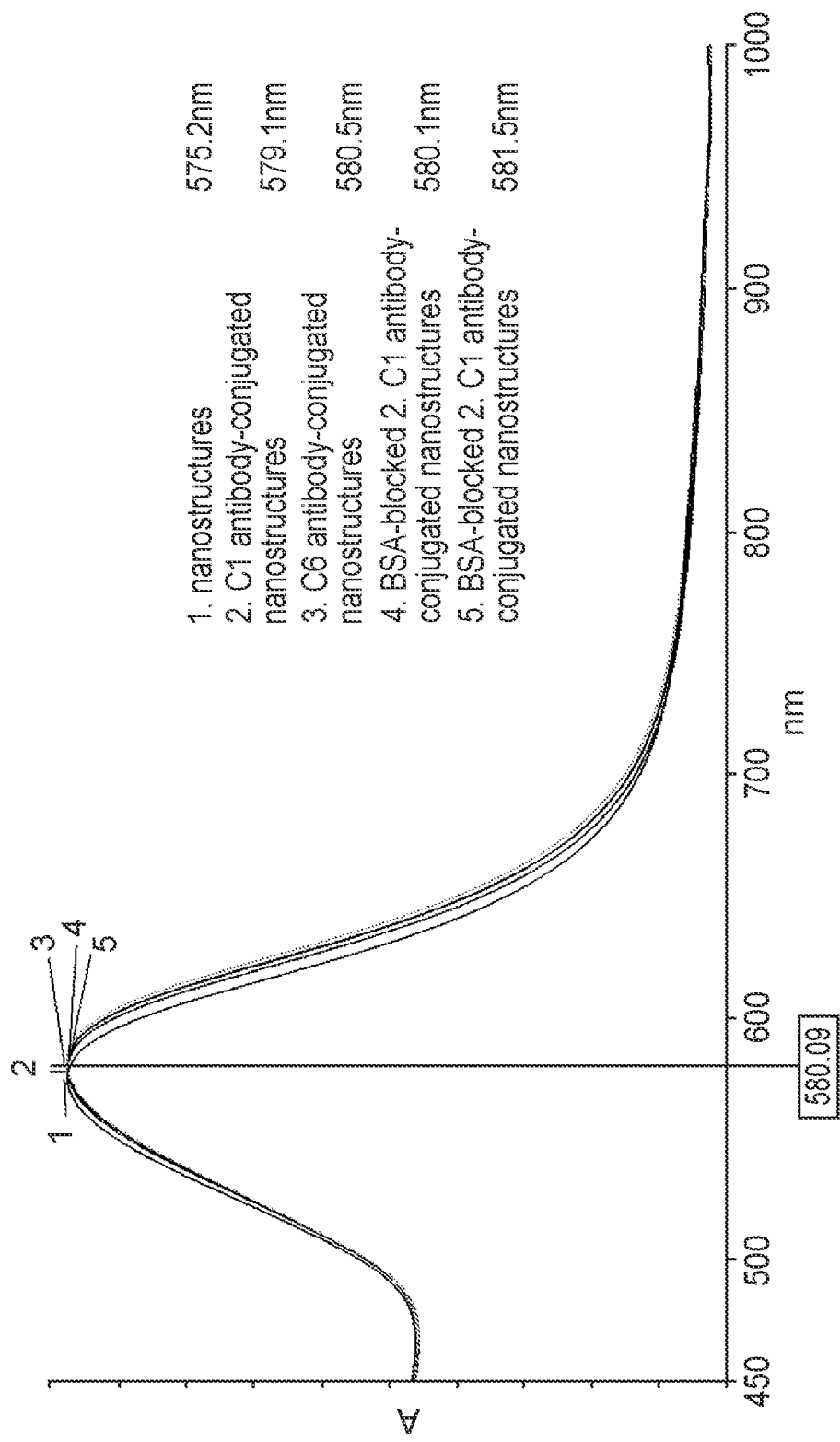
FIG. 6. Shows the peak shifts of unconjugated nanostructures, C1 antibody- and C6-antibody nanostructures, and C1 antibody and C6-antibody nanostructures after BSA blocking.

FIG. 6 shows the spectral shifts, for conjugates generated using the adsorptive protocol, of (i) 50 nm nanostructures prior to conjugation; (ii) 50 nm nanostructures conjugated to C1 antibody; (iii) 50 nm nanostructures conjugated to C6 antibodies; (iv) C1-conjugated nanostructures after blocking with BSA; and (v) C6-conjugated nanostructures after blocking with BSA. The study shows that the antibody binding caused 4-5 nm red-shift, and an additional shift of 1 nm was induced upon blocking of conjugates with BSA.

Figure 7:
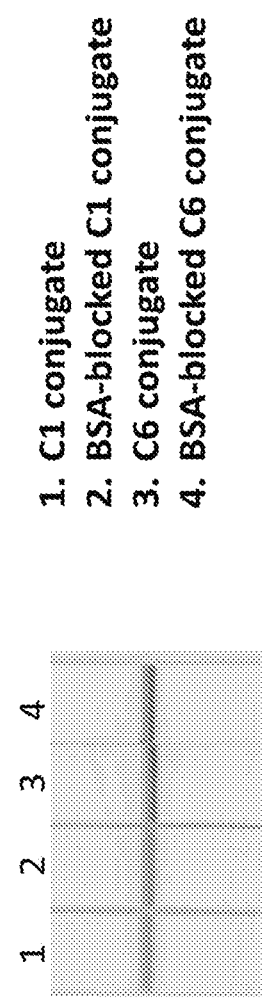
FIG. 7. Shows lateral flow strips striped with Protein A (0.5 mg/mL), dipped in a solution containing the conjugated nanostructures generated using the absorptive protocol, or the conjugated nanostructures generated using the absorptive protocol and blocked with BSA.

To confirm that the antibody molecules bound to the nanostructures, lateral flow strips striped with Protein A (0.5 mg/mL) were dipped in a solution containing the conjugated nanostructures, or the conjugated nanostructures blocked with BSA. FIG. 7 shows that the conjugates were formed and that BSA blocking did not disrupt the conjugates

Example 3. Conjugation of Nanostructures to Antibodies Via Thiol-Mediated Conjugation Protocol To generate nanostructure conjugates using the thiol-mediated conjugation protocol, nanostructures having a plurality of protrusions and an average diameter of 50 nm (λmax at 575 nm-1.0 OD/mL) were adjusted to pH 8.8 with 0.1M borate. TCEP-reduced C1 or C6 antibodies (about 33 picomoles per OD nanostructure) were titrated in and mixed well for 15 minutes. 2 mg BSA per ml was added and mixed for a further 15 minutes. Nanostructure/C1 or /C6 mixtures were centrifuged for 15,000 g for 10 minutes; supernatant was removed; and the conjugates were resuspended in conjugate diluent CG-1P, comprising PBS/BSA and CHAPS. CHAPS was particularly important to the resuspension of C6 antibodies, which are hydrophobic. Moreover, the CHAPS detergent helped prevent nonspecific size/shape changes leading to aggregation.

Figure 8:
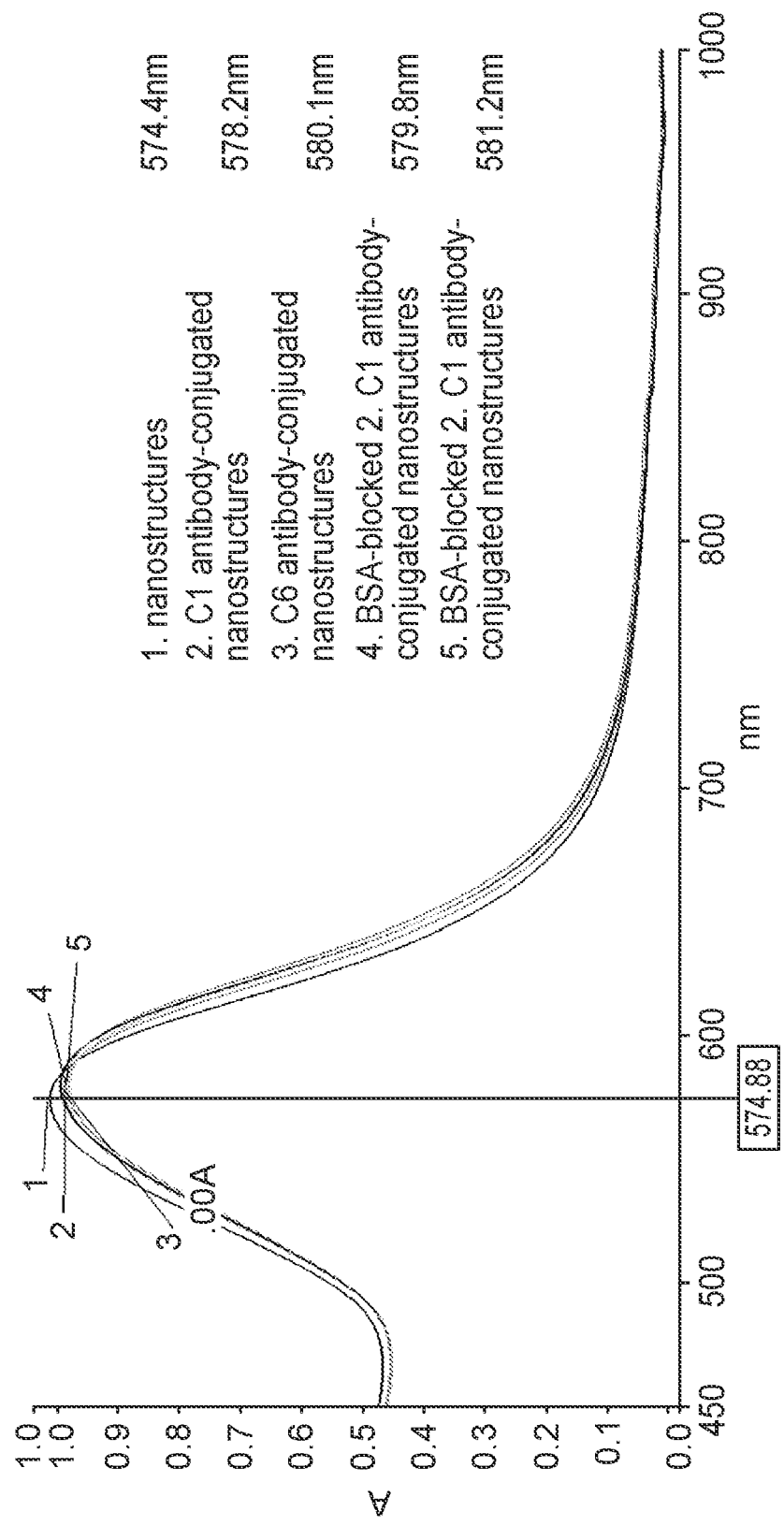
FIG. 8. Shows the spectral shifts for the nanostructure conjugates generated using a thiol-mediated conjugation protocol, of (i) 50 nm nanostructures prior to conjugation; (ii) 50 nm nanostructures conjugated to C1 antibody; (iii) 50 nm nanostructures conjugated to C6 antibodies; (iv) C1-conjugated nanostructures after blocking with BSA; and (v) C6-conjugated nanostructures after blocking with BSA.

FIG. 8 shows the spectral shifts, for conjugates generated using the thiol-mediated conjugation protocol, of (i) 50 nm nanostructures prior to conjugation; (ii) 50 nm nanostructures conjugated to C1 antibody; (iii) 50 nm nanostructures conjugated to C6 antibodies; (iv) C1-conjugated nanostructures after blocking with BSA; and (v) C6-conjugated nanostructures after blocking with BSA. The study shows that the antibody binding caused 4-5 nm red-shift, and an additional shift of 1 nm was induced upon blocking of conjugates with BSA.

Figure 9:
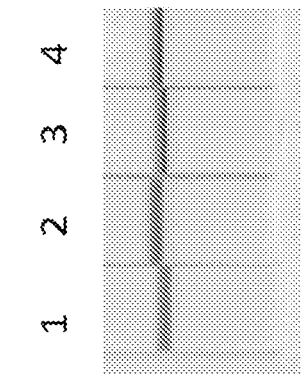
FIG. 9. Shows lateral flow strips striped with Protein A (0.5 mg/mL), dipped in a solution containing the conjugated nanostructures generated using the thiol-mediated protocol, or the conjugated nanostructures generated using the thiol-mediated protocol and blocked with BSA.

To confirm that the antibody molecules bound to the nanostructures, lateral flow strips striped with Protein A (0.5 mg/mL) were dipped in a solution containing the conjugated nanostructures, or the conjugated nanostructures blocked with BSA. FIG. 9 shows that the conjugates were formed and that BSA blocking did not disrupt the conjugates.

Figure 10A:
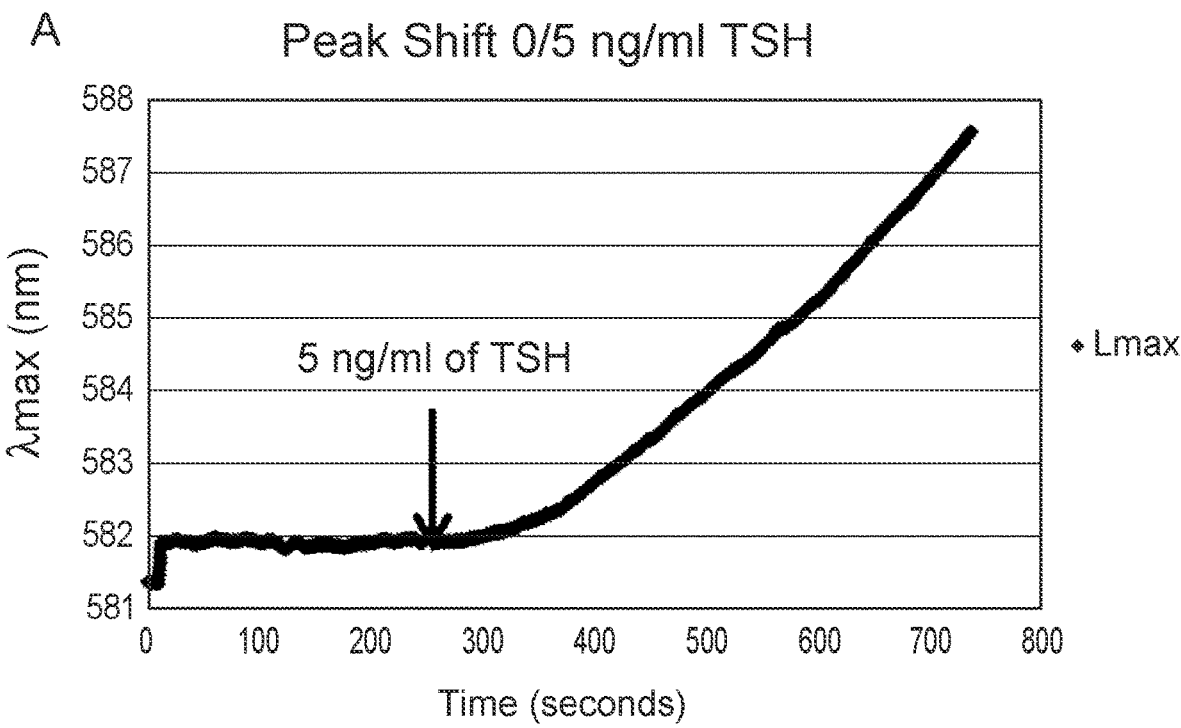
FIG. 10A. Shows the changes in the composite lambdamax for C1 and C6 conjugates generated using 50 nm nanostructures and the adsorptive protocol.
Figure 10B:
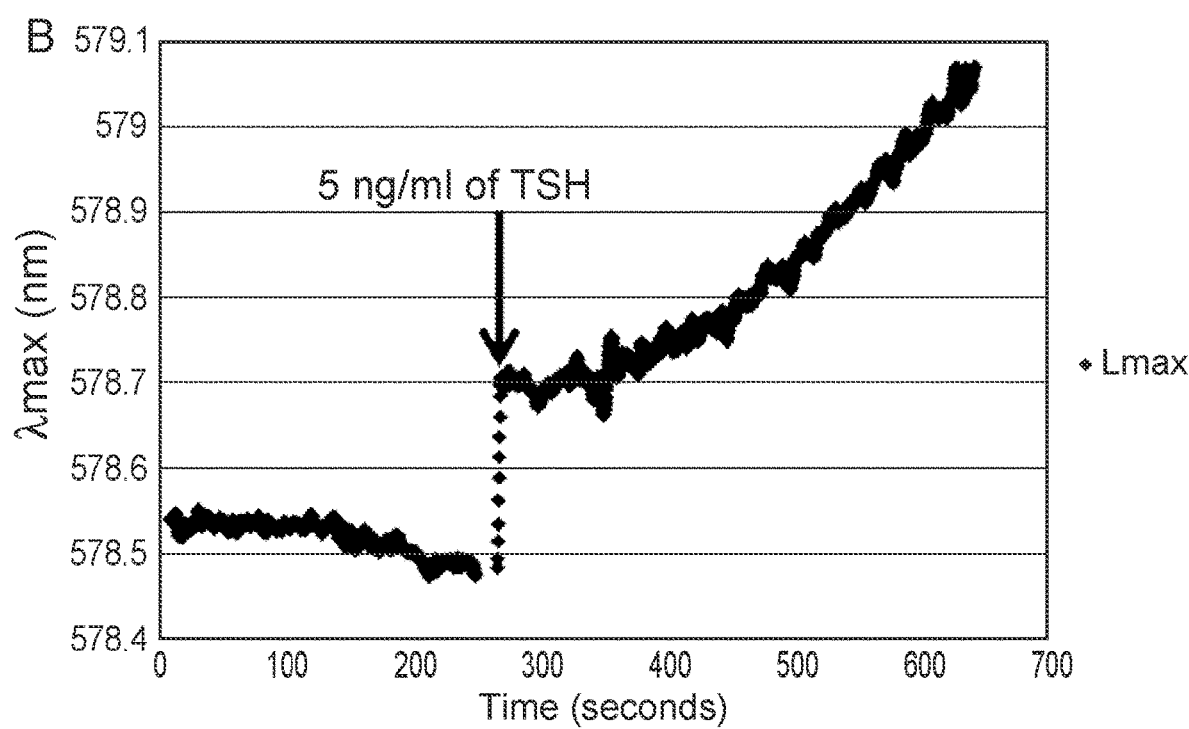
FIG. 10B. Shows the changes in the composite lambdamax for C1 and C6 conjugated generated using 50 nm nanostructures and the thiol-mediated conjugation protocol.

Example 4. Sensitive Antigen Detection Using the Antibody-Conjugated Nanostructures The ability of the conjugates to detect the presence of antibody was tested. Changes in the composite λmax of C1 and C6 adsorptive conjugates in the absence and presence of TSH. Anti-TSH clones C1 and C6 were purchased from Arista Biologicals. These antibodies target the beta fragment of TSH. Clones C1 and C6 conjugated to 50 nm nanostructures were mixed together in PBS/BSA buffer and scanned for changes in λmax for 250 seconds to obtain a baseline on a Nicoya™ lifesciences' OpenSPR spectrophotometer. TSH was then added to 5 ng/ml and λmax was monitored for additional 450 seconds. FIG. 10A shows the changes in the composite $\lambda_{max}$ for C1 and C6 conjugates generated using 50 nm nanostructures and the adsorptive protocol. FIG. 10B shows the changes in the composite $\lambda_{max}$ for C1 and C6 conjugated generated using 50 nm nanostructures and the thiol-mediated conjugation protocol.

Figure 11:
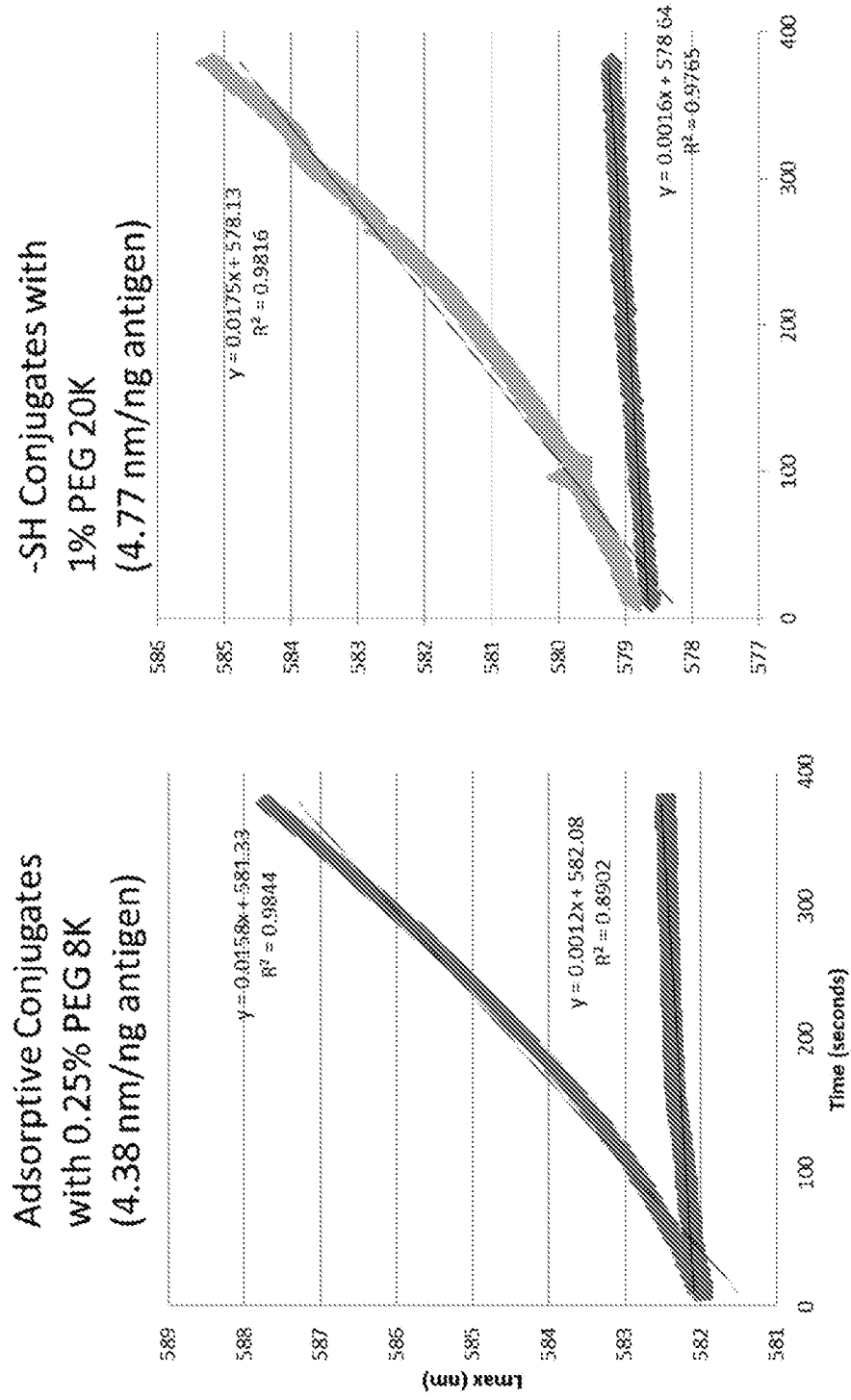
FIG. 11. Shows the effect of the presence of accelerant on the spectral shift for the conjugates prepared by the adsorptive (left panel; 0.25% PEG) and thiol-mediated (right panel; 1% PEG) protocols.

Next, the effect of the presence of accelerant on the spectral shift for the conjugates prepared by the adsorptive and thiol-mediated protocols was assessed. The results of the study showed that different concentrations of accelerant provide different responses in adsorptive protocol conjugates versus thiol-mediated, covalently linked conjugates. For example, a lower molecular weight and lower concentration of PEG produced similar response from adsorptive versus covalently linked conjugates (FIG. 11).

Figure 12:
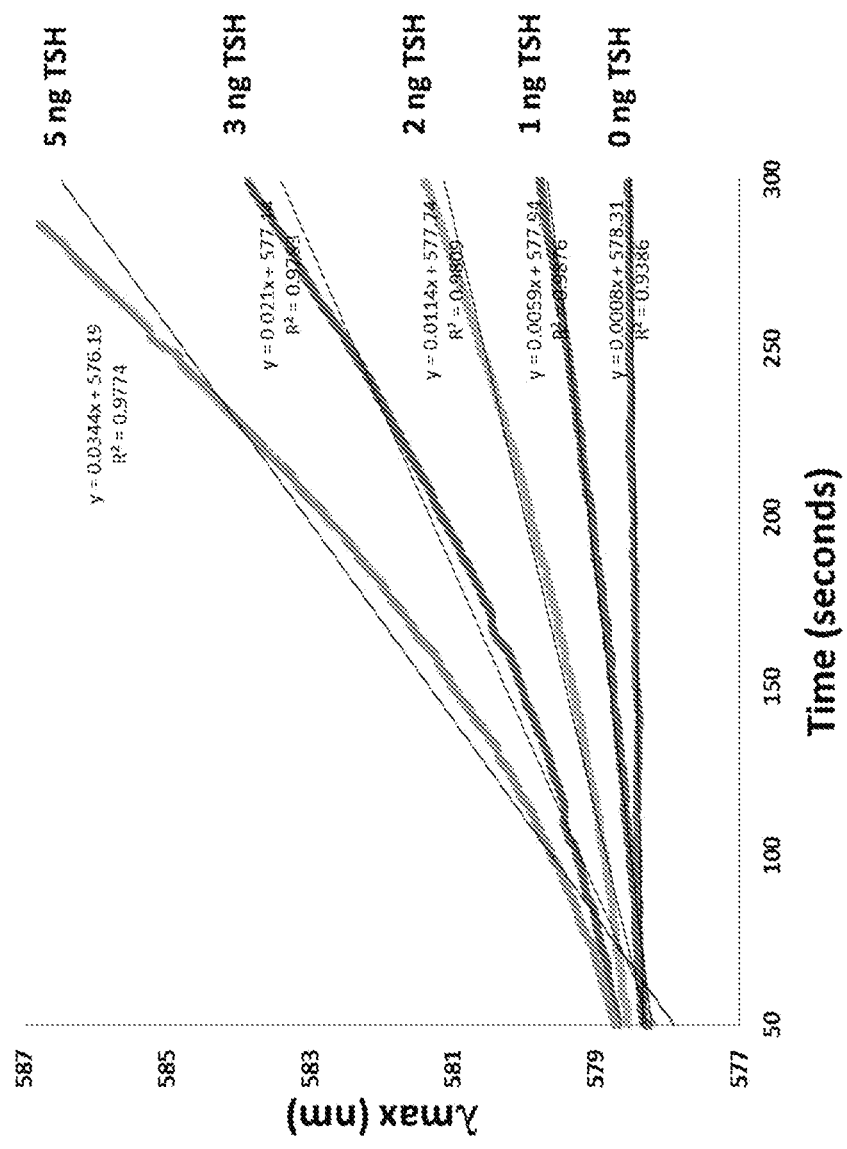
FIG. 12. shows the dose-response curve and kinetics over time in the presence of increasing amounts of antigen (TSH), using covalently linked conjugates in the presence of 0.1% PEG and 0.5% methylcellulose.

FIG. 12 shows the dose-response curve and kinetics over time in the presence of increasing amounts of antigen (TSH), using covalently linked conjugates in the presence of 0.1% PEG and 0.5% methylcellulose. FIG. 12 shows the peak shift dose response of covalently linked conjugates of anti-TSH C1 and C6 in the presence of 0.1% polyethylene glycol and 0.5% methylcellulose.

Figure 13:
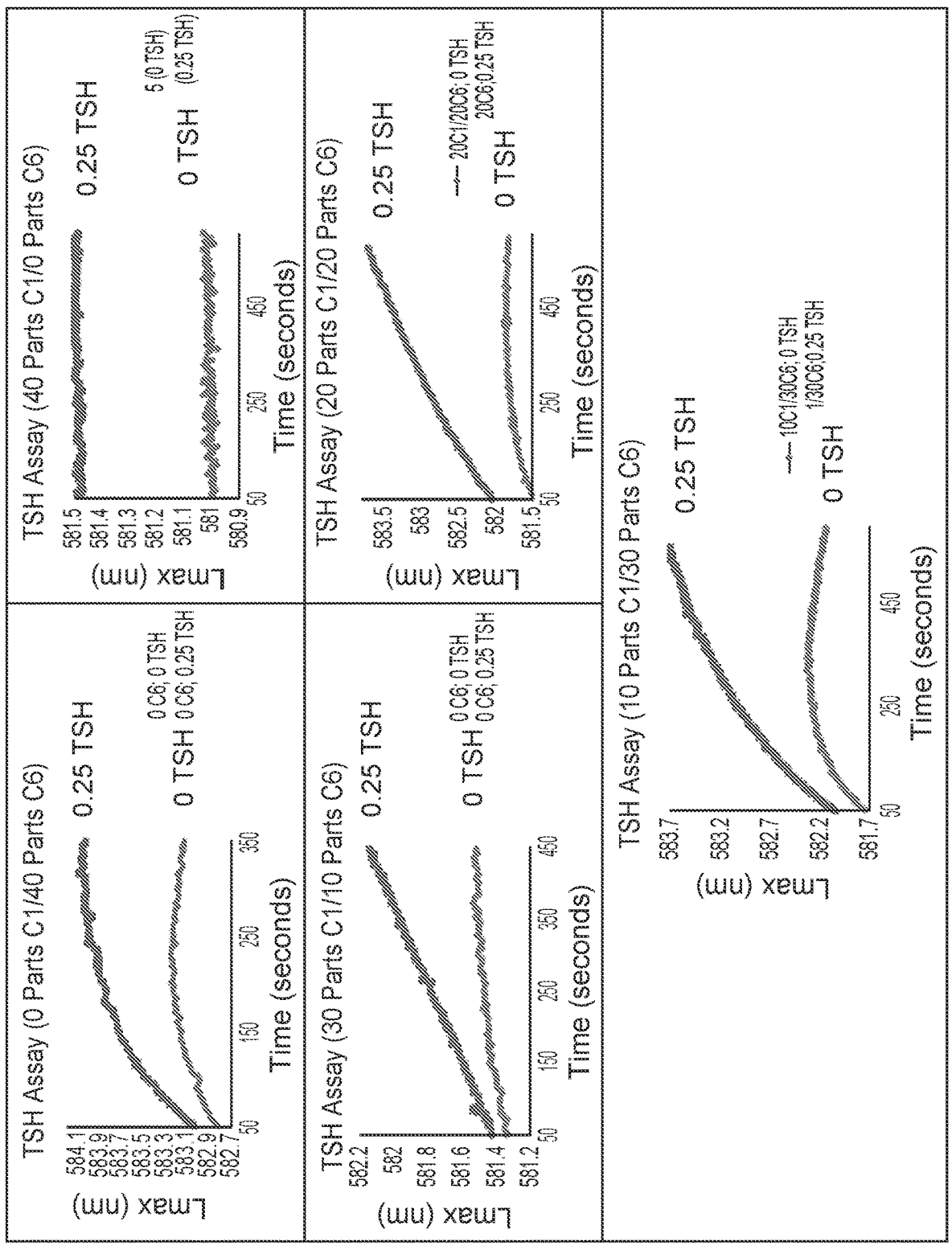
FIG. 13. Shows reaction curves obtained in the absence (0 ng) or the presence of 0.25 ng of hTSH for different ratios of C1 and C6 antibodies in the conjugates (0 parts C1/40 parts C6, top left panel; 40 parts C1/0 parts C6, top right panel; 30 parts C1/10 parts C6, middle left panel; 20 parts C1/20 parts C6, middle right panel; 10 parts C1/30 parts C6, bottom panel).

Next, a study was conducted to determine the effect on the ratios of conjugates (e.g., C1-nanostructure and C6 nano-structure) used. FIG. 13 shows the results obtained from C1 or C6 alone or the various ratios of the two antibodies. Reaction curves were obtained in the absence (0 ng) or the presence of 0.25 ng of hTSH. In this particular assay, the clone C1 was essentially nonreactive by itself but made significant contributions once C6 was introduced. Without wishing to be bound by theory, the assay in some embodiments depends on the formation of 3D nanoparticle ensembles; and appropriate changes in the ionic strength, pH and detergents may provide additional enhancements in sensitivity.

Figure 14A:
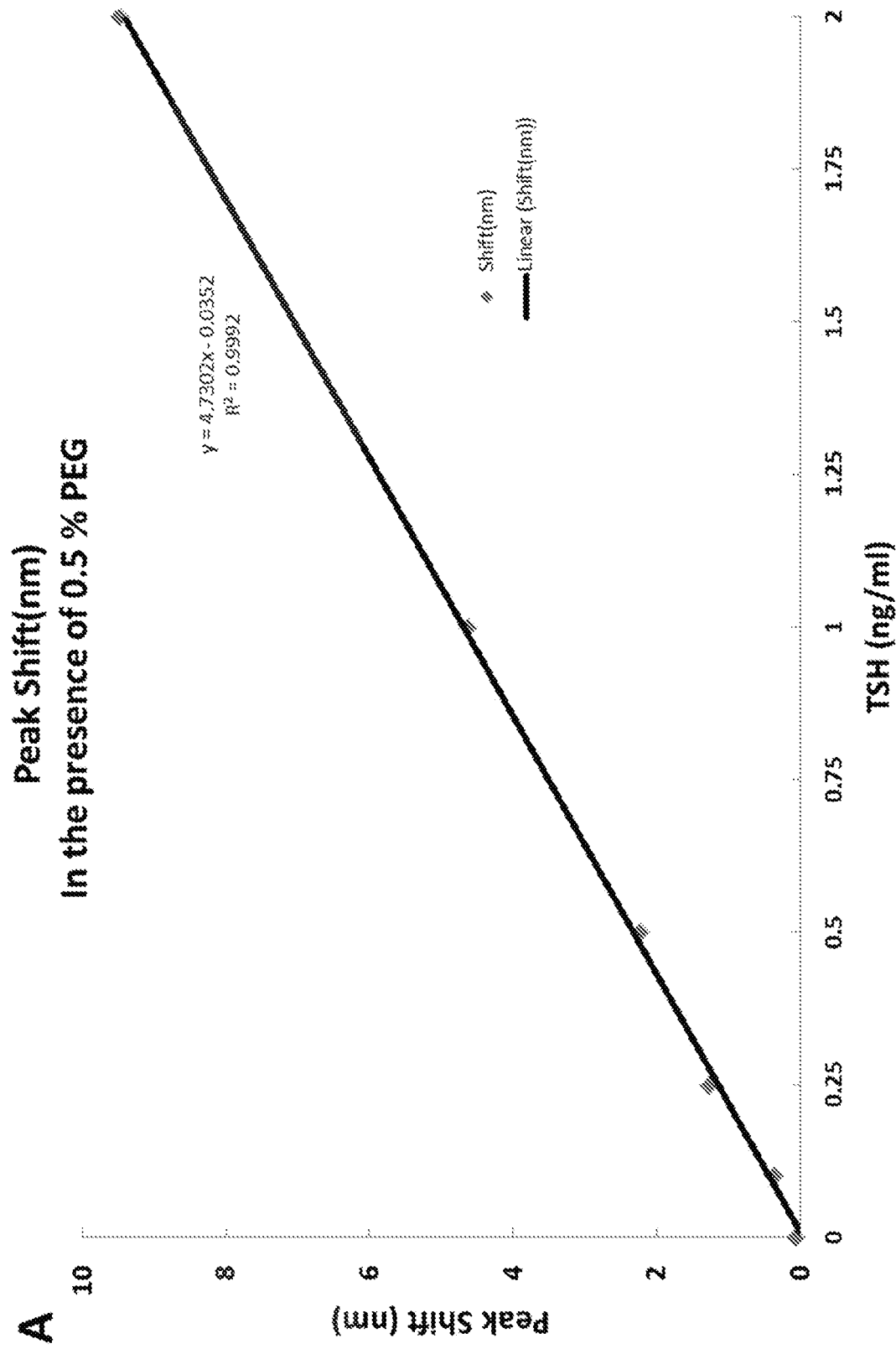
FIG. 14A. Shows peak shift for the conjugates in the presence of increasing amounts of TSH and 0.5% PEG.
Figure 14B:
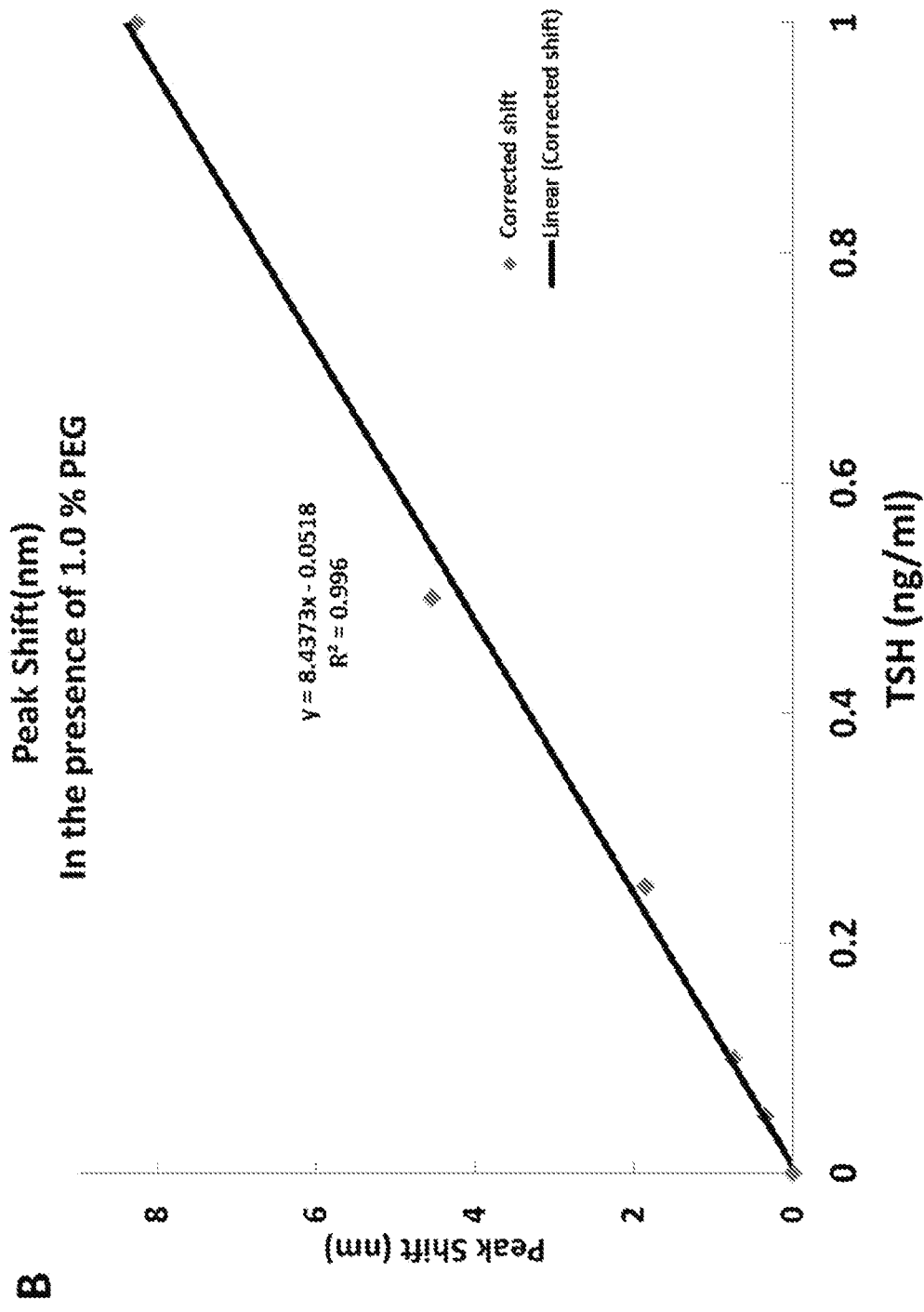
FIG. 14B. Shows peak shift for the conjugates in the presence of increasing amounts of TSH and 1.0% PEG.

In another study, the two conjugates (15 μl of C1 and 25 μl of C6) were mixed with PBS/BSA/PEG 8K solution containing 0-2 ng TSH. The final concentration of PEG in the reaction mixture was 0.5% (FIG. 14A) or 1.0% (FIG. 14B). The components of the reaction mixture (0.8 ml) were placed in a disposable cuvette for recording changes in the λmax which were measured using Nicoya's OpenSPR™ spectrometer. The curves obtained in these experiments were then fit using regression analysis. The $\lambda_{max}$ change was calculated for 10 minutes from the regression analysis and plotted to generate the curve, as shown in FIGS. 14A and 14B. An increase in PEG concentration from 0.5% (FIG. 14A) to 1% (FIG. 14B) increased the sensitivity by almost a factor of 2.

Figures 15A, 15B:
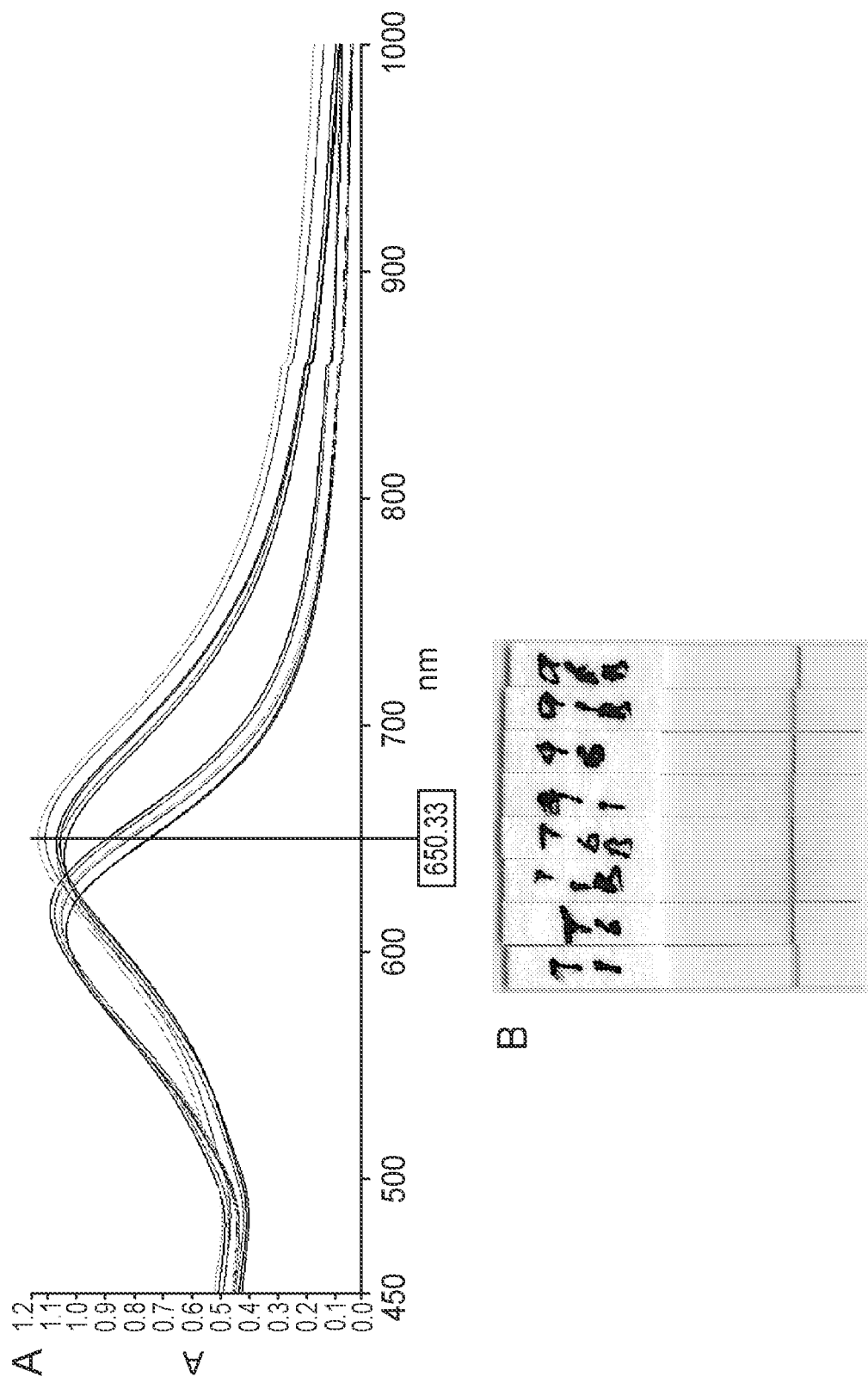
FIG. 15A. (top panel) shows the conjugation of anti-hTSH antibodies C1 and C6 to the 70 and 90 nm nanostructures and their reactivates with Protein A lateral flow strips.
FIG. 15B. (bottom panel) shows that Protein A lines on nitrocellulose reacted as expected before and after blocking with BSA.

Example 5. Larger Nanostructures Having a Plurality of Spikes and Average Diameters of 70 or 90 nm Conjugation and detection using nanostructures having a plurality of spikes and an average diameter of 70 or 90 nm (inclusive of spikes) were tested. FIG. 15A (top panel) shows the conjugation of anti-hTSH antibodies C1 and C6 to the 70 and 90 nm nanostructures and their reactivities with Protein A lateral flow strips. FIG. 15B (bottom panel) shows that Protein A lines on nitrocellulose reacted as expected before and after blocking with BSA. The unconjugated 70 and 90 nm nanostructures showed λmax of 609.5 and 641.9, respectively. The attachment of C1 and C6 followed by blocking with BSA caused up to 8 nm shift in λmax. The table below shows the quantified data from FIG. 15A.

TABLE 1

Lmax of 70 and 90 nm C1 and C6 conjugates in the presence or absence of BSA blocking

|  | nm | cursor |
|---|---|---|
| 70 nm unconjugated | 609.5 | 1.034 |
| 70-C1 conjugate | 614.3 | 1.05 |
| 70 nm unconjugated | 609.6 | 1.034 |
| 70-C6 conjugate | 615.1 | 1.057 |
| 90 nm unconjugated | 641.9 | 1.063 |
| 90-C1 conjugate | 647.3 | 1.055 |
| 90 nm unconjugated | 641.9 | 1.041 |
| 90-C6 conjugate | 647.6 | 1.068 |
| 70-C1-BSA | 617 | 1.074 |
| 70-C6-BSA | 617.7 | 1.089 |
| 90-C1-BSA | 650.2 | 1.131 |
| 90-C6-BSA | 650.1 | 1.107 |

Figure 16:
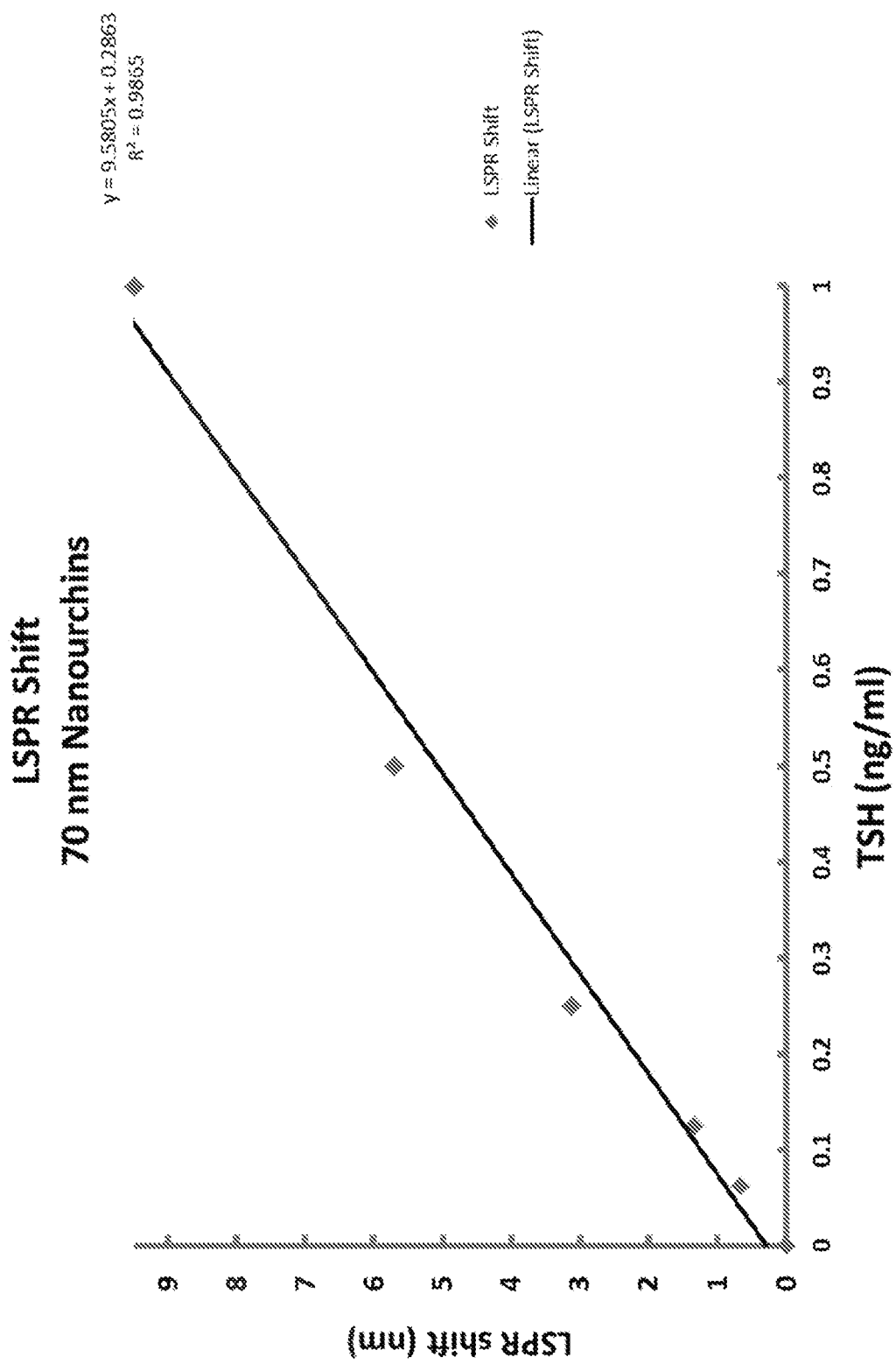
FIG. 16. Shows the spectral shift of conjugates comprising about 70 nm diameter nanostructures.
Figure 17:
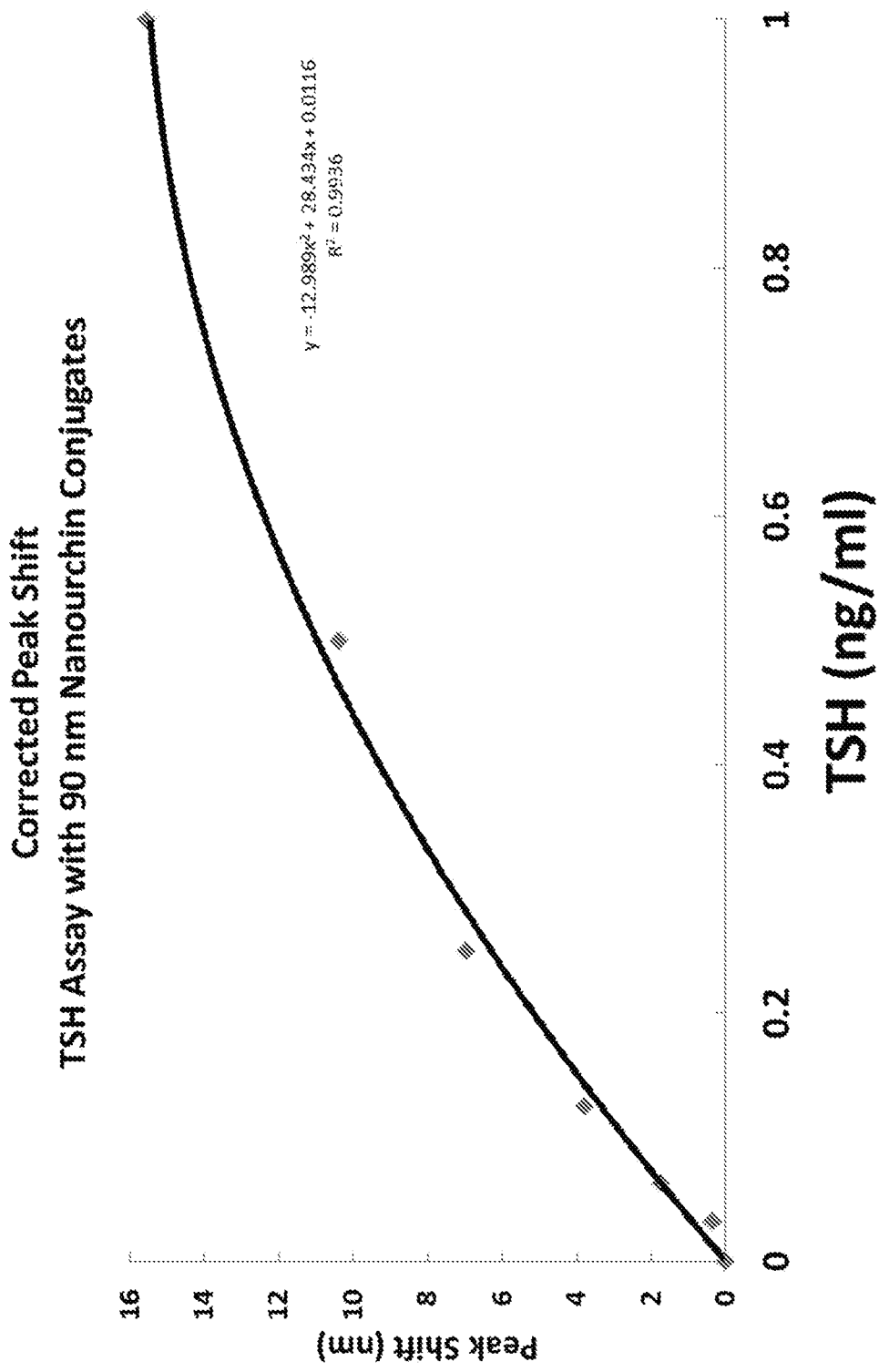
FIG. 17. Shows the spectral shift of conjugates comprising about 90 nm diameter nanostructures.

Sensitivity among the nanostructures of different diameters was compared. The spectral shift of conjugates comprising about 70 nm diameter nanostructures was improved compared to that of conjugates having a diameter of about 90 nm. Strikingly, further increasing the diameter of the nanostructures to about 90 nm resulted in a further increase in sensitivity, as the increase in diameter to 90 nm produced nanostructure-conjugates capable of producing net spectral shift of greater than 15 nm (FIG. 16 and FIG. 17). Together, the studies showed that the increase in diameter of the nanostructures having a plurality of spikes resulted in increased detection sensitivity. Also, it was observed that increasing PEG improves sensitivity up to a certain PEG concentration but very high concentrations are counterproductive.

Example 6. Activity of Nanostructures Having a Plurality of Protrusions Versus Nanorods in the Solution-Based Assay A study was conducted to compare the sensitivity of detection of the nanostructure conjugates provided herein comprising a plurality of protrusions to nanorod conjugates comprising the same antibodies.

Figure 18:
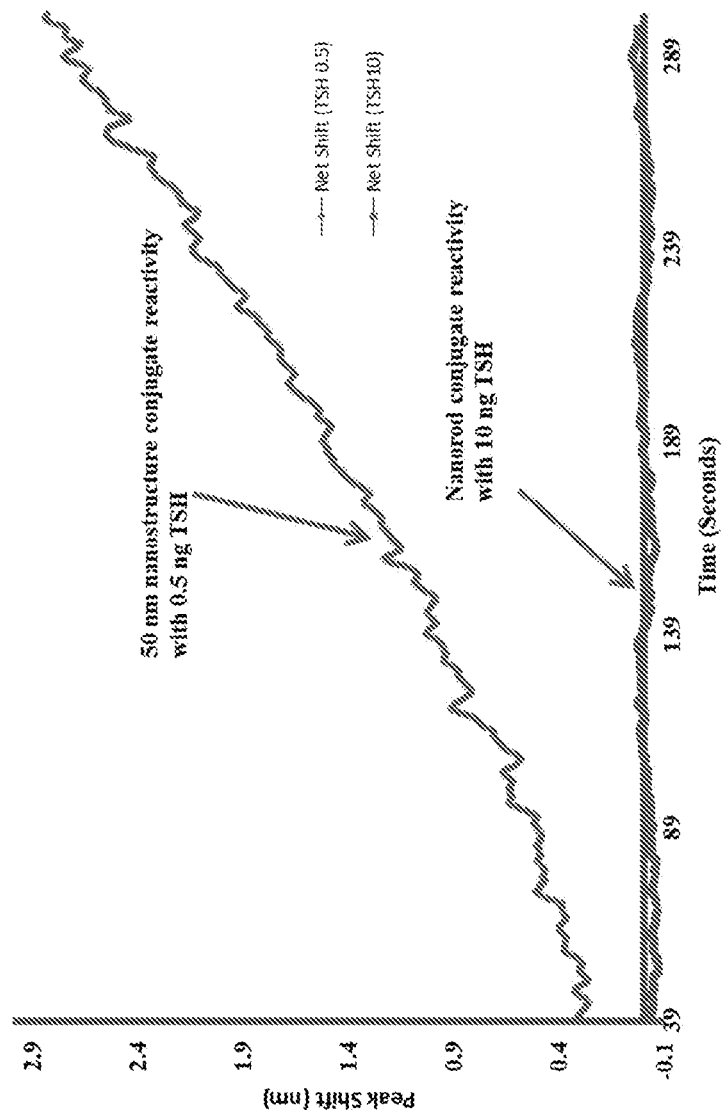
FIG. 18. Shows detection of TSH measured by the peak shift of 50 nm nanostructures comprising a plurality of protrusions versus nanorods.

Nanorods (45.5±6.3 nm in length and 17.4±1.2 nm in width) were obtained from Nanocomposix and conjugated to antibody clones 1 and 6 via an adsorptive conjugation protocol. 50 nm nanostructures comprising a plurality of protrusions were also conjugated to antibody clone 1 and 6 using passive adsorption at pH9.2 in borate buffer as described above. The results of the study are provided in FIG. 18. The ability of the nanorod conjugates to detect TSH was tested in a buffer comprising PBS, BSA and 1% PEG 20000 with or without the addition of 10 ng of TSH. FIG. 18 shows that there was no net change in λmax, which was calculated by subtracting values obtained with TSH from those without TSH; λmax changes were recorded using Nicoya Lifesciences' OpenSPR™. Nanostructures having a plurality of protrusions were tested similarly but the amount of TSH was 0.5 ng as the rates were too fast at TSH concentrations of 10 ng/ml. Strikingly, the nanostructures comprising a plurality of protrusions exhibited robust TSH detection as measured by peak shift analysis, whereas the nanorods failed to detect TSH. This result was unexpected at least because nanorods are believed to be excellent sensors of refractive index changes. However, in the present solution-based assay, nanostructures having a plurality of protrusions, and not nanorods, exhibit superior effects.

Example 7. Low-pH Conjugation Protocol Yields Conjugates Exhibiting Sensitive Detection A study was conducted to assess the ability of conjugates formed using nanostructures comprising a plurality of protrusions that were conjugated to antibody at a lower pH.

Anti-TSH antibody clones C1 and C6 were conjugated to gold nanostars prepared by a single vessel seed-free method. The nanostars were diluted to an OD=1 with distilled water. The pH was approximately 6.0. Clones 1 and 6 were separately added to the nanostar solutions to obtain 5 µg of the antibody per OD of the nanostar solution. After 15 min incubation, the conjugates were blocked with 2 mg BSA per ml of the conjugate. The conjugates were then separated from reactants by centrifugation at 25000 g for 15 min. The centrifugation may be repeated if the pellets are loose by adding 10 mM phosphate buffered BSA (1%). The final sediment is dissolved in the following CHAPS containing buffer: PBS (1×), BSA (1%) and CHAPS (2%). Dissolution is aided by sonication for up to 30 seconds.

Figure 19:
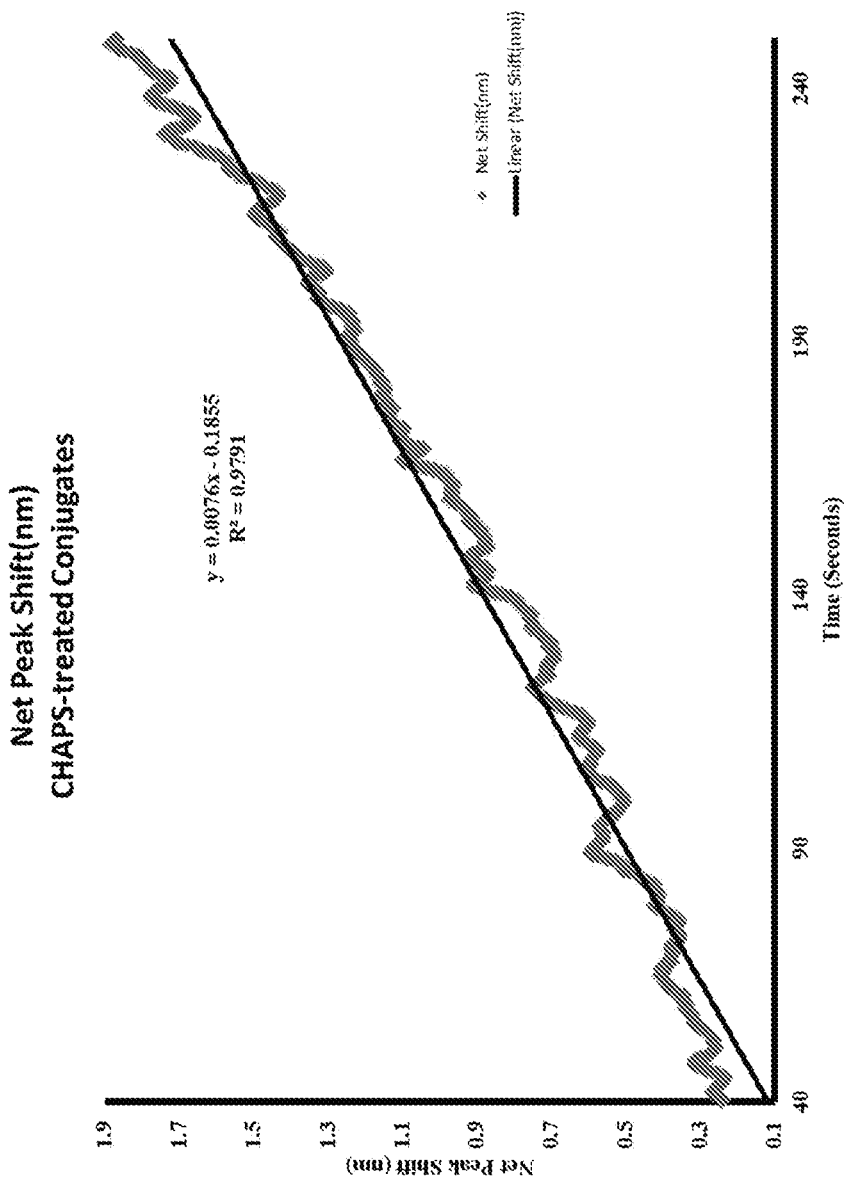
FIG. 19. Shows the net peak shift of CHAPS-treated conjugates comprising nanostructures having a plurality of protrusions, conjugated to antibodies at pH 6.0.

The ability of these conjugates to detect TSH was tested by diluting the final C1(3 parts) and C6 (1 part) conjugates with PBS/BSA (1% BSA in PBS) to an OD of ~0.5 and recording peak shift with time in the presence or absence of 1 ng/ml TSH on OpenSPR™ spectrometer. The results are shown in FIG. 19, which shows the net shift (the net shift is calculated by subtracting shift seen in absence of any TSH from that caused by 1 ng/ml of TSH) plotted against time of the reaction. The study showed that the conjugates exhibited robust detection activity.

Figure 20:
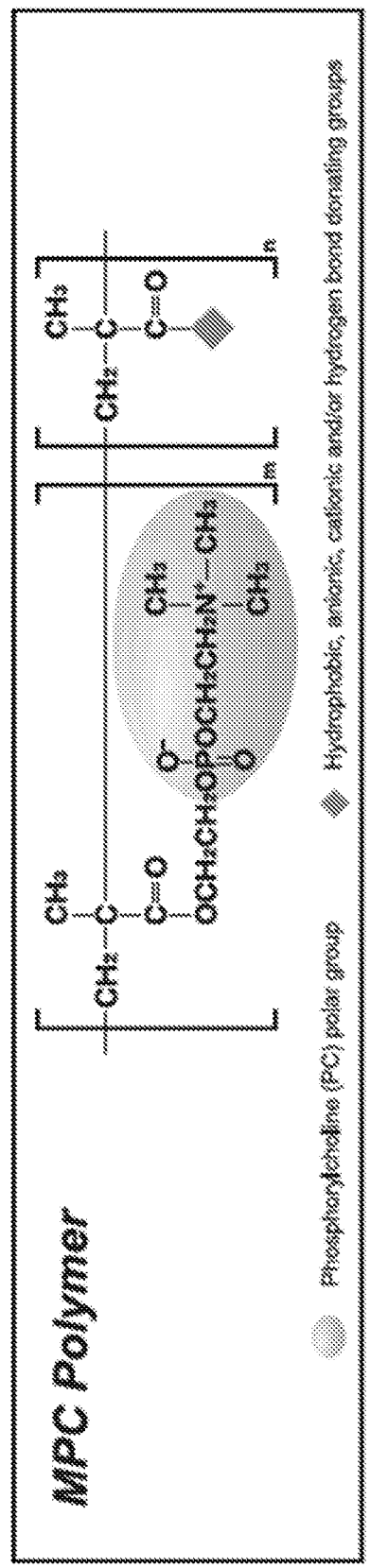
FIG. 20 shows an image of a Biolipidure® polymer substrate with a polar charged head group, and a tail that has varying properties from hydrophobic, anionic, cationic, and/ or hydrogen bond donating groups. The image is from the website of NOF corporation, from which Biolipidure® reagents are commercially available.

Example 8. Simultaneous Reduction in Nonspecific Adsorbance of Serum Proteins and Increase of Immunoassay Sensitivity Biolipidure® reagents are synthetic polymeric reagents that contain a phosphorylcholine (PC) polar group, and a polymeric tail that contains hydrophobic, anionic, cationic, and/or hydrogen bond donating groups, FIG. 20. These reagents are also known as 2-methacryloyloxyethyl phosphorylcholine polymers (MPC) that have been incorporated into polymeric biomaterials due to their properties of resisting nonspecific protein adsorption, cell adhesion, and blood coagulation. Some features of these reagents include enhancement of sensitivity and accuracy, suppression of non-specific adsorption, stabilization of antibodies and enzymes, reduction of lot-to-lot variation without the hassle of biohazardous handling.

For many applications, the Biolipidure® reagents are added to a final working solution in order to achieve the desired results of the product. In order to prevent nonspecific adsorption in immunoassays, the Biolipidure® reagents can be applied by coating microplates, coating magnetic beads, and by adding to the antibodies that are present in solution. In some embodiments, Biolipidure® reagents can be used by preparing a buffer solution with 1 wt % of Biolipidure® reagent; dissolving the sample (for example, mucosa) in the buffer, and loading the diluted sample on the sample pad of the immunochromatograph.

Figure 21:
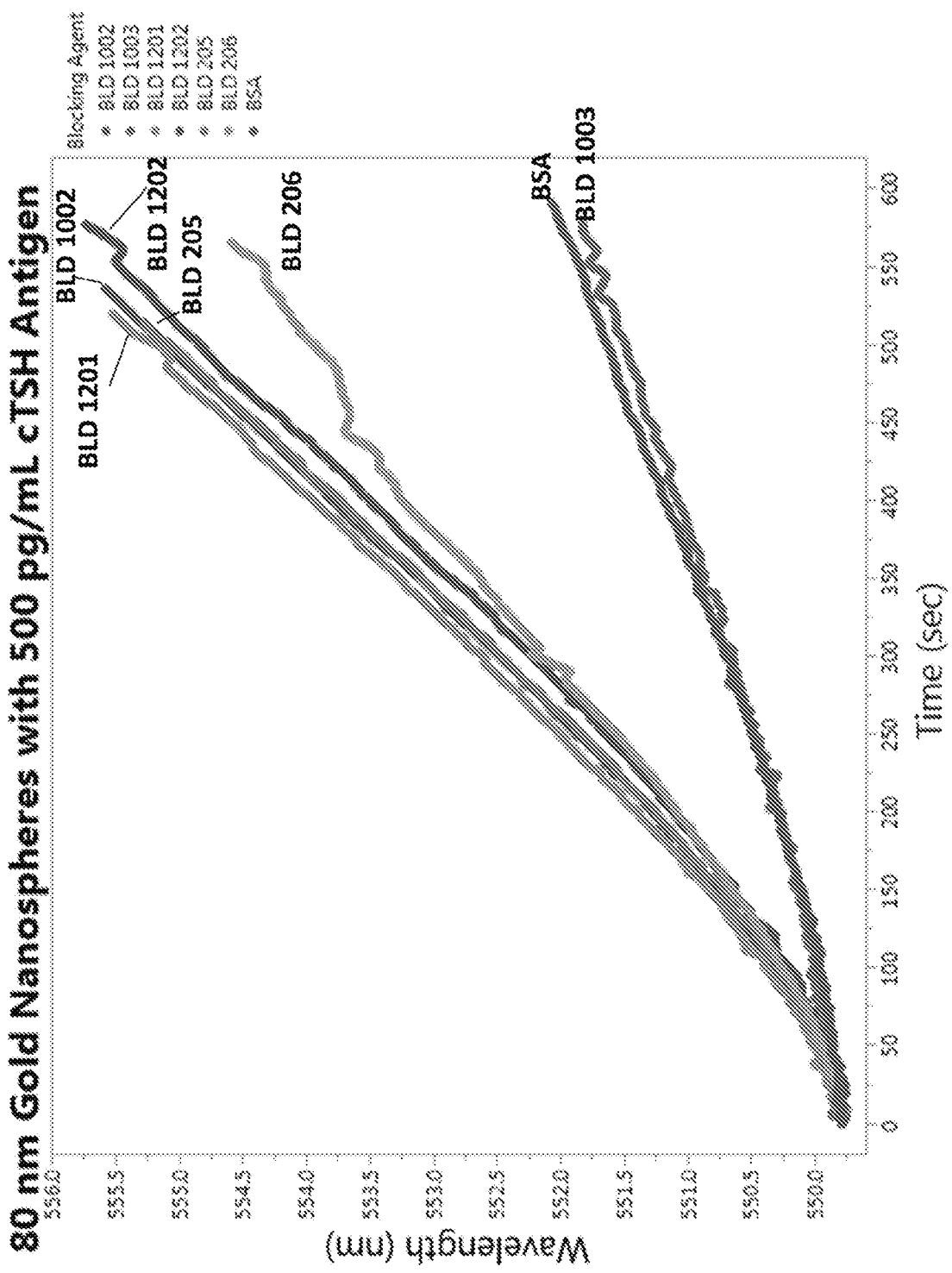
FIG. 21 shows the wavelength shift with respect to time of anti-TSH coated nanoparticles that are blocked with a range of Biolipidure® reagents and BSA. Compared to BSA conjugates, blocking with 1002, 1201, 1202, 205 and 206 all enhance the sensitivity of the conjugates in 10 minutes compared to the standard BSA conjugate.

Surprisingly, when added to the surface of gold nanoparticles during the blocking phase of passive IgG adsorption, the Biolipidure® reagents can both reduce nonspecific adsorption of serum proteins, and enhance the sensitivity of the assay. Briefly, gold nanospheres were coated with mouse IgG for 15 min, followed by one of the Biolipidure® blocking agents, 205, 206, 1002, 1003, 1201, 1202, or BSA for 15 min. The antibody-gold conjugates were washed 3× and suspended in conjugate diluent for storage prior to testing. To test the sensitivity of the Biolipidure® conjugates to antigen compared to BSA conjugates, the conjugates were tested with 500 pg/mL of antigen over the course of 10 minutes in buffer, tris buffered saline/bovine serum albumin (TBS BSA). Surprisingly, 5/6 Biolipidure® blocked conjugates show a 2-3 fold enhancement over the standard BSA blocked conjugates. The results are shown in FIG. 21.

Figure 22A:
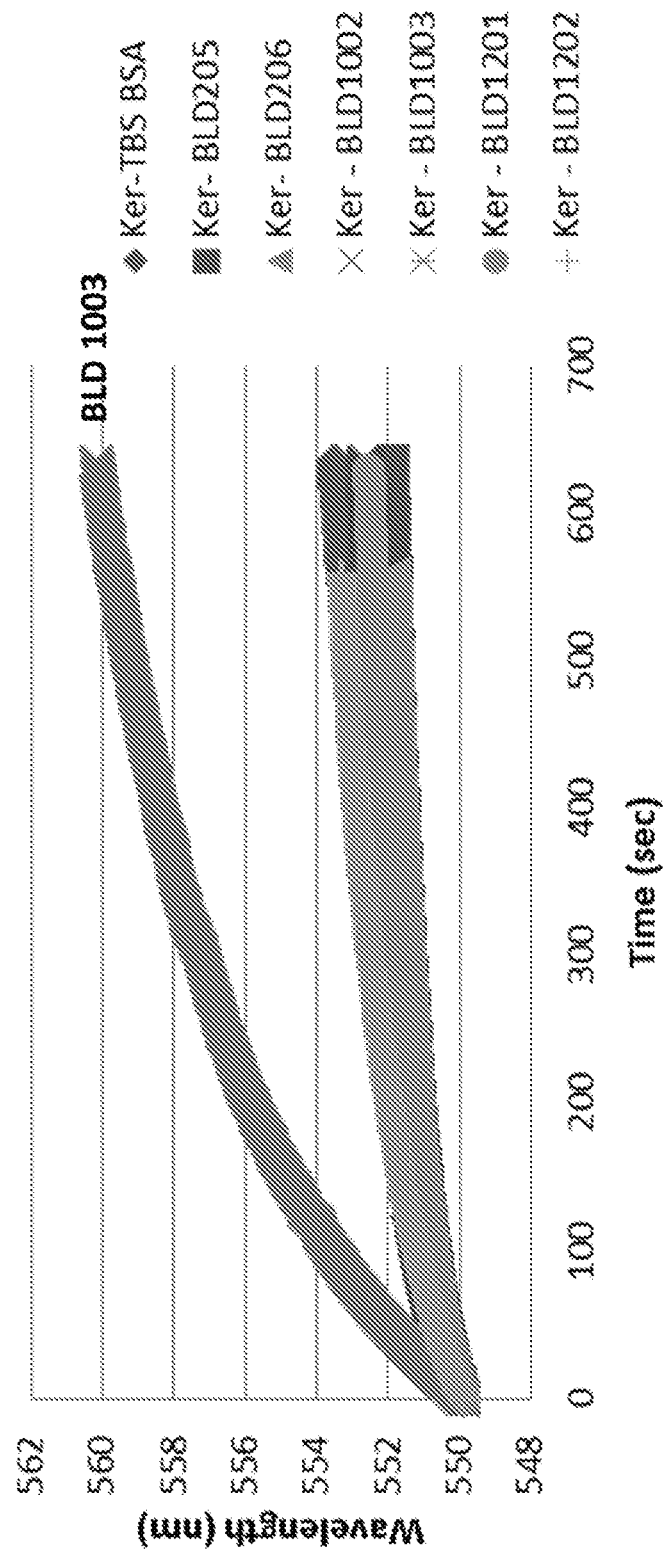
FIGS. 22A and 22B show the nonspecific adsorption of the conjugates blocked with Biolipidure® reagents 1002, 1003, 1201, 1202, 205, 206, and BSA (FIG. 22A). Due to the large wavelength shift from 1003.
Figure 22B:
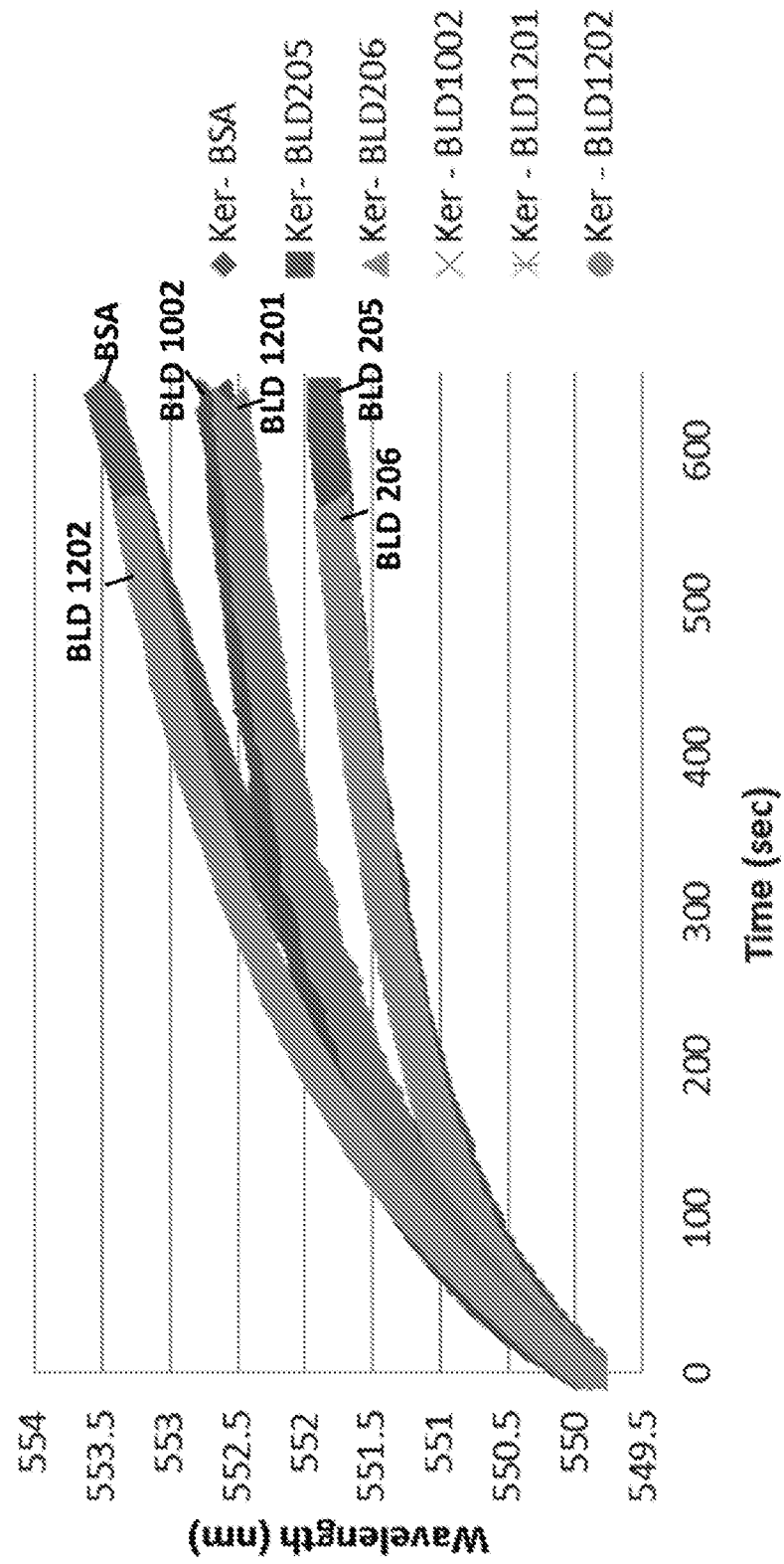

Even more surprisingly, when testing for nonspecific protein adsorption in serum samples, blocking with Biolipidure® has the power to reduce NSB compared to the standard BSA conjugates. All Biolipidure® conjugates were tested with the same canine serum sample that has been verified to have low/normal TSH levels. The serum samples were diluted 1/20 in TBS/BSA, and their wavelength change was monitored with respect to time. The Biolipidure® reagent 1003 showed a large, 10 nm, wavelength shift in response to the addition of serum to the nanoparticle conjugates, as shown in FIG. 22A. This shift is ~3-4× greater than all other conjugates, therefore it was removed to clearly observe the wavelength shifts of the other conjugates, FIG. 22B. The wavelength shift of BSA blocked IgG conjugates over the time course of 10 minutes in response to the addition of canine serum was around 3.5 nm. The Biolipidure® conjugate 1202 showed a similar wavelength shift as the BSA blocked conjugates. The conjugates blocked with 205, 206, 1002, and 1201 all showed a decrease in wavelength shift in the presence of canine serum.

Due to the varying properties of Biolipidure® reagents, they have different responses to canine serum, and enhancing the sensitivity of a sandwich immunoassay. Biolipidure® reagents 205, 206, 1002, and 1201 all show the capability to both reduce the wavelength shift with canine serum, and improve the LSPR shift in response to antigen in this homogeneous sandwich immunoassay. Biolipidure® reagent 1202 was able to improve the response to antigen, while the wavelength shift in response to the addition of canine serum to the sample was equivalent to that of the BSA conjugates.

Figure 23:
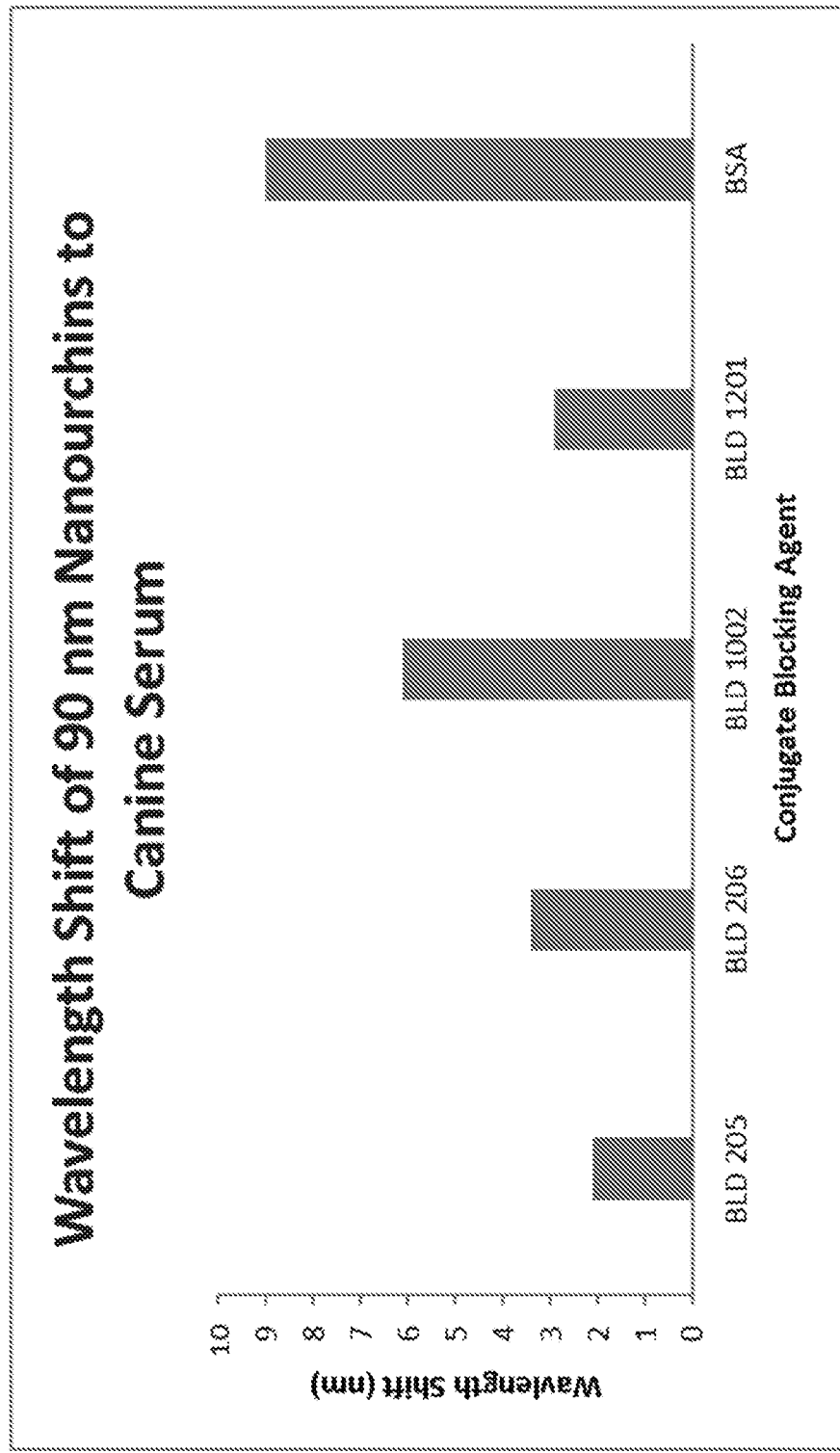
FIG. 23 shows the wavelength shift in canine serum of the nanoparticle conjugates with BSA blocking reagents vs 4 of the Biolipidure® blocking reagents that have shown the greatest effect on both improving the sensitivity and reducing the nonspecific wavelength shift in serum.
Figure 24:
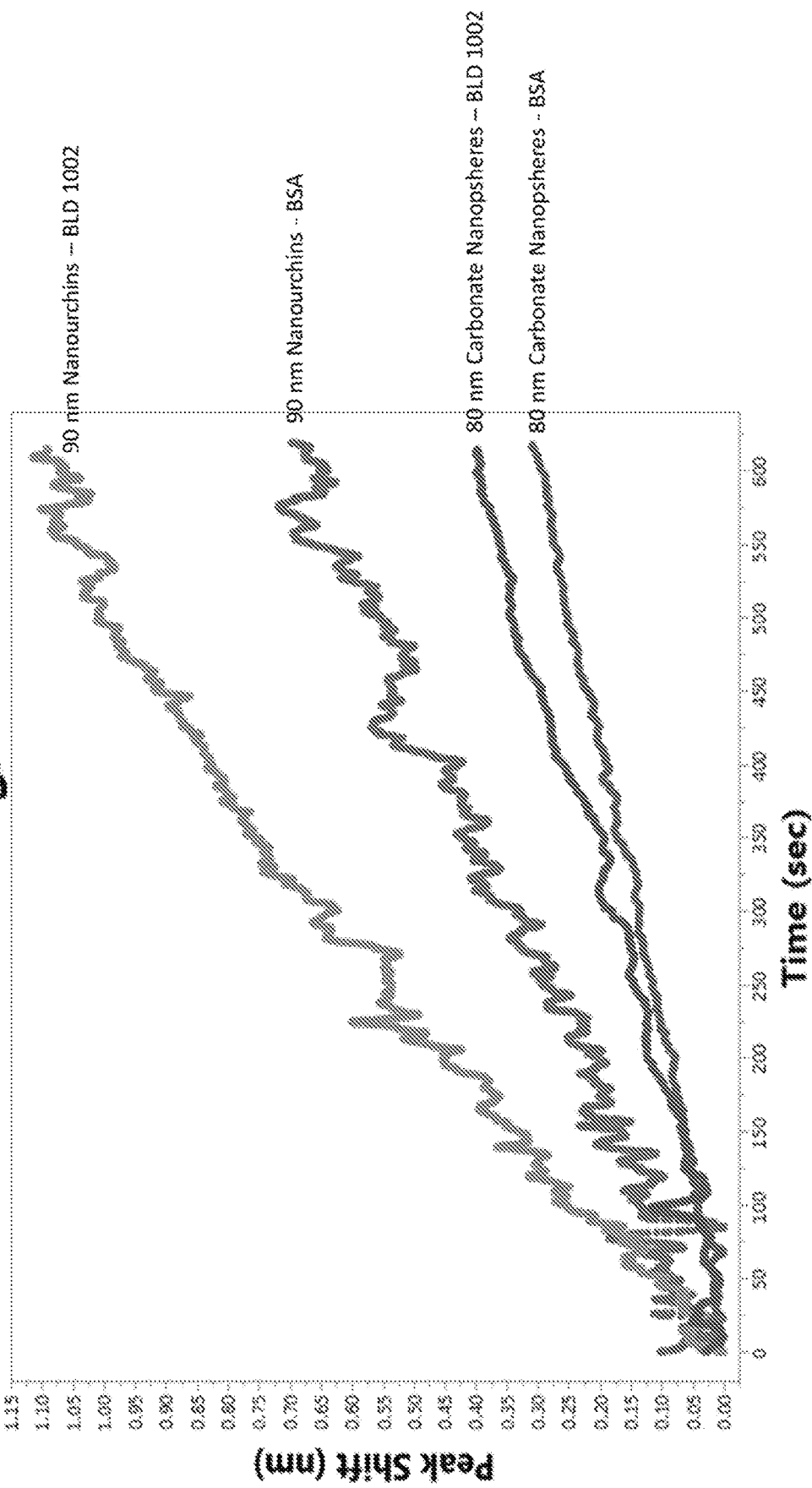
FIG. 24 shows the improvement of the wavelength shift in response to 1 ng/mL which is diluted 1/20 for a final concentration of 50 pg/mL cTSH antigen in TBS BSA buffer. This figure compares the positive response of 80 nm spheres blocked with BSA vs Biolipidure® 1002 and 90 nm nanourchins blocked with BSA vs Biolipidure® 1002. In both cases the Biolipidure® blocked reagent improves the wavelength shift with response to antigen. The assay conditions for the results provided in FIG. 24 included the following: 50 mM Tris, 150 mM NaCl, 1% BSA, at a pH of 7.7

The increase of sensitivity of antigen detection, and the decrease in the nonspecific wavelength shift with canine serum was not limited to spherical nanoparticles. When the Biolipidure® reagents were added to the surface of the IgG conjugates, the sensitivity of the antibody conjugates to antigen was increased, and the wavelength shift in response to the addition of serum was significantly decreased in comparison to BSA blocked conjugates, FIG. 23. There was a remarkable increase in response of 90 nm nanourchin (i.e., anisotropic nanoparticles that comprise a plurality of protrusions on the surface) conjugates blocked with Biolipidure® reagent 1002, 2×, for 1 ng/mL of antigen diluted 20 fold to 50 pg/mL of canine antigen, FIG. 24. These conjugates are also much more sensitive than the spherical gold conjugates blocked with Biolipidure® 1002.

The results of the study provided a surprising method for increasing sensitivity while decreasing non-specific binding in the assay. Changing the blocking agent during the gold nanoparticle-antibody passive conjugation procedure from BSA to some Biolipidure® reagents resulted in a significant increase in wavelength shift to antigen in buffer conditions, and there was a decrease in the wavelength shift in response to the addition of serum to the conjugates, indicating a likely decrease in nonspecific adsorption from serum components.

Example 9. Salt Combinations and EDTA Reduce Non-Specific Binding

Studies were conducted to determine the reason for non-specific binding and avenues for reducing non-specific binding in the LSPR assay. Non-specific binding could be due to electrostatic or hydrophobic interactions between gold conjugates and macro serum proteins. Initial studies focused on NaCL. Based on Hofmeister theory, experiments were conducted to determine if MgCl2 or NaSCN may be beneficial for preventing protein aggregation. In addition, chaotropic salts could have an impact on gold conjugates colloidal stability. A schematic of Hofmeister series salts is provided in FIG. 25.

Figure 26:
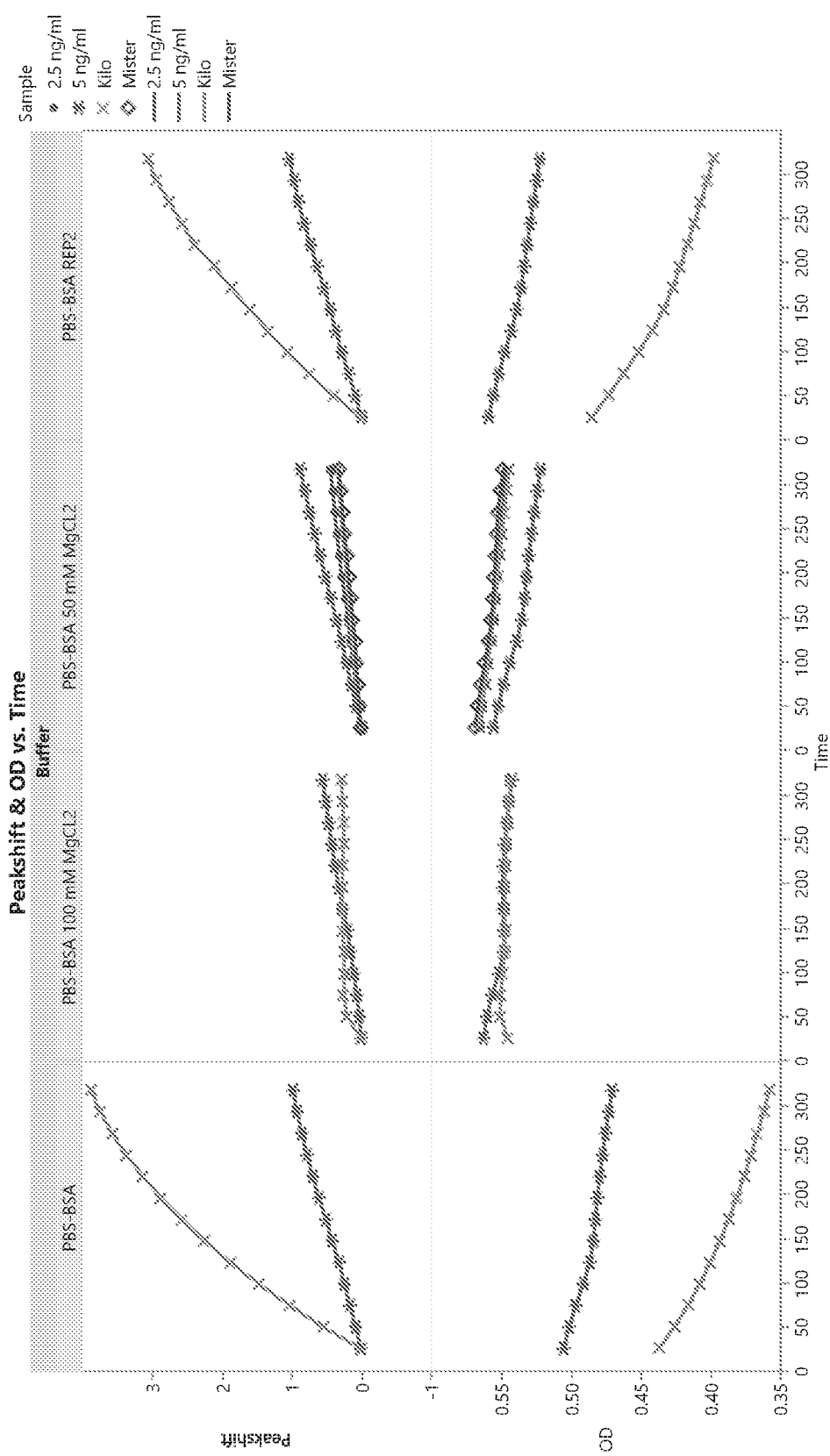
FIG. 26 shows the impact of the presence of MgCl2 on the levels of non-specific binding in the assay, using nanosphere cTSH conjugates. Kilo and Mister are two different normal canine serum samples.

An initial study using chaotropic salt MgCl2 showed promising results. Without the salt, a normal canine serum sample yielded significant non-specific binding. With 50-100 mM MgCl2, the non-specific binding signal was drastically reduced (FIG. 26). The LSPR peak shift results after 5 minutes are shown below in Table 2. Non-specific binding and 5 ng/ml LSPR signals were disproportionally reduced by the presence of MgCl2.

TABLE 2

| LSPR peak shift in the presence or absence of MgCl2 | | | | |
|---|---|---|---|---|
| Buffer | 2.5 ng/ml | 5 ng/ml | Kilo | Mister |
| PBS-BSA | . | 0.980 | 3.888 | . |
| PBS-BSA 100 mM MgCL2 | . | 0.552 | 0.285 | . |
| PBS-BSA 50 mM MgCL2 | 0.448 | 0.875 | 0.334 | 0.322 |
| PBS-BSA REP2 | . | 1.035 | 3.070 | . |

Figure 27:
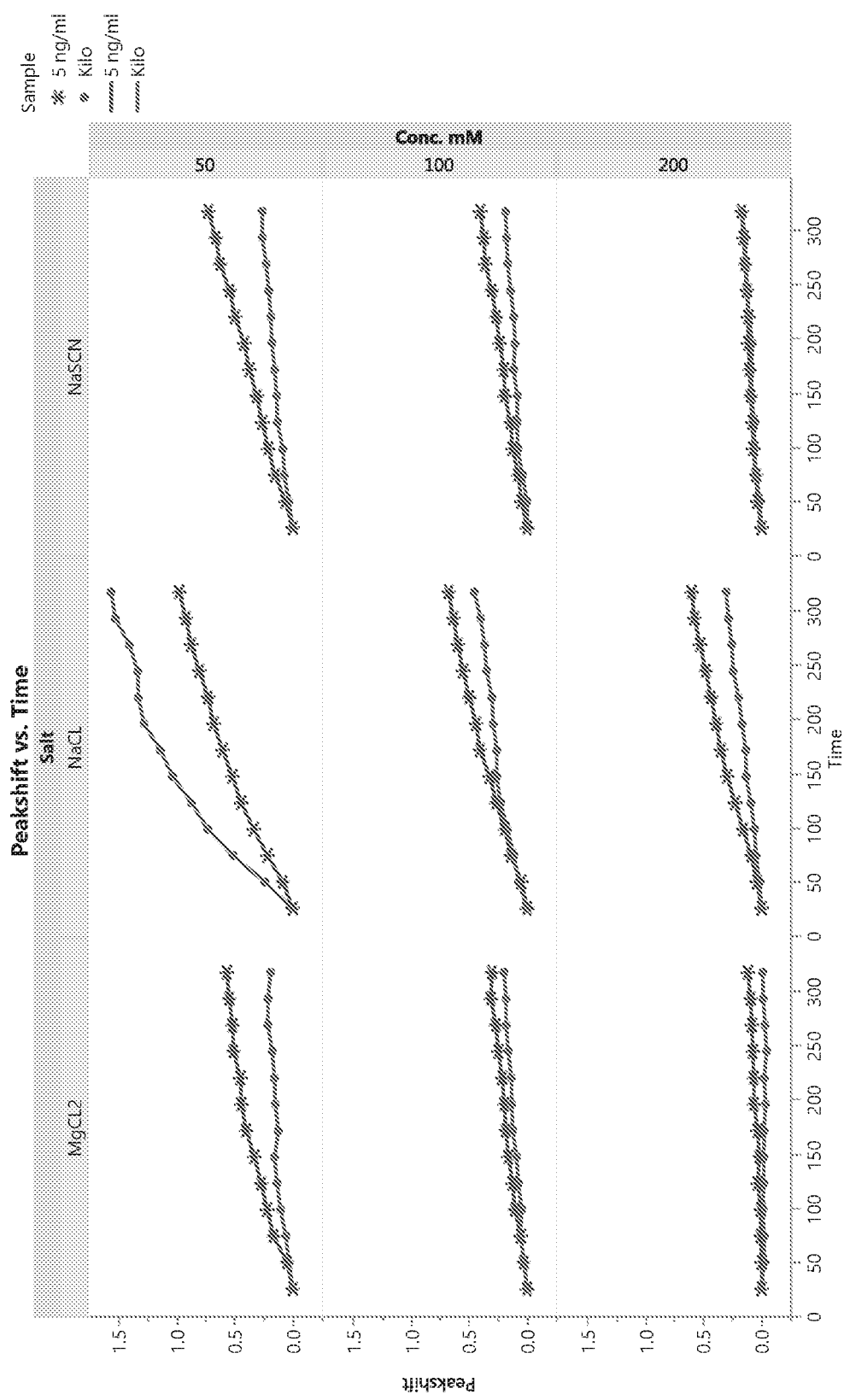
FIG. 27 shows the impact of the presence of MgCl2, NaCl, or NaSCN on non-specific binding.
Figure 28:
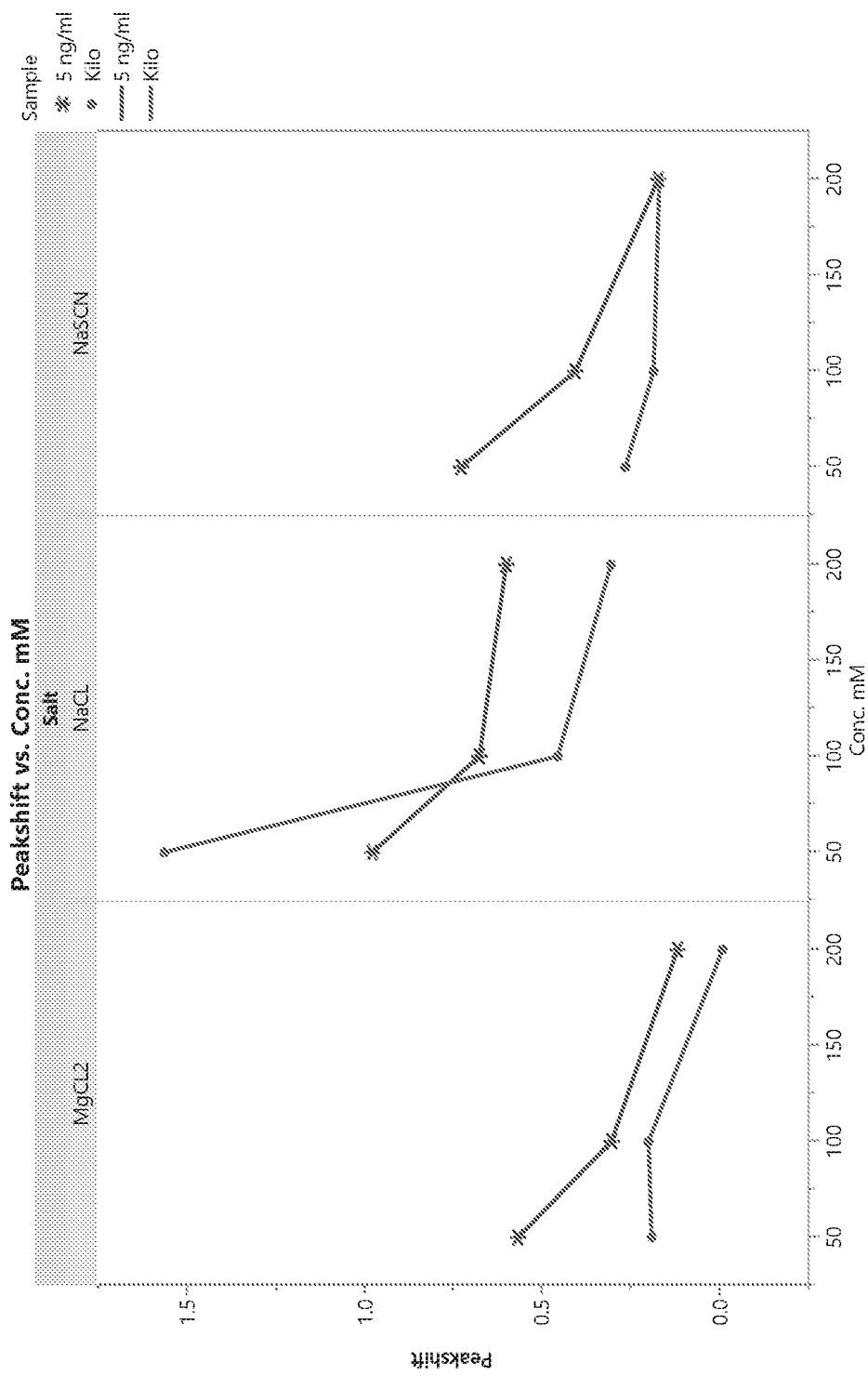
FIG. 28 shows the LSPR peak shift results after 5 minutes from the study testing the presence of MgCl2, NaCl, or NaSCN

In another study, the impact of other chaotropic salts on the 80 nm nanosphere cTSH conjugates was assessed. MgCl2, NaCl, and NaSCN were tested. Both MgCl2 and NaSCN exhibited a reduction in non-specific binding (FIG. 27). The LSPR peak shift results after 5 minutes are provided in FIG. 28 and in Table 3, below.

TABLE 3

| | LSPR peak shift in presence of NaCL, MgCl2, or NaSCN | | | | | | | | |
|---|---|---|---|---|---|---|---|---|---|
| | NaCL | | | MgCL2 | | | NaSCN | | |
| Conc. mM | 5 ng/ml | Kilo | S/B | 5 ng/ml | Kilo | S/B | 5 ng/ml | Kilo | S/B |
| 0 | 0.940 | 4.085 | | 0.940 | 4.085 | | 0.940 | 4.085 | |
| 50 | 0.975 | 1.561 | 0.625 | 0.566 | 0.190 | 2.981 | 0.726 | 0.263 | 2.755 |
| 100 | 0.674 | 0.454 | 1.486 | 0.303 | 0.199 | 1.525 | 0.404 | 0.184 | 2.196 |
| 200 | 0.599 | 0.304 | 1.970 | 0.117 | −0.010 | | 0.172 | 0.168 | 1.021 |

Figure 29:
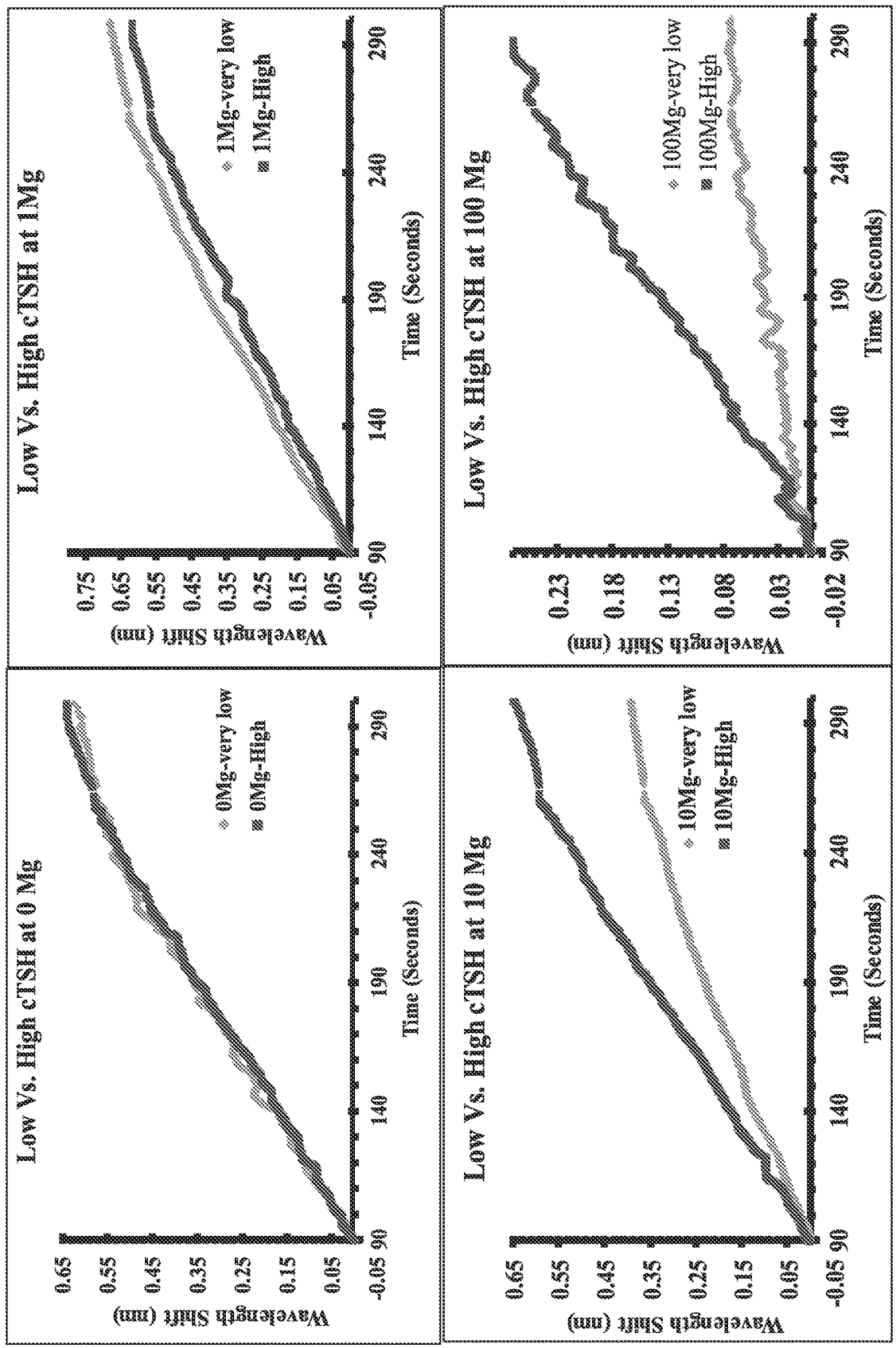
FIG. 29 shows the effects of the presence of Mg on non-specific binding in the LSPR assay.
Figure 30:
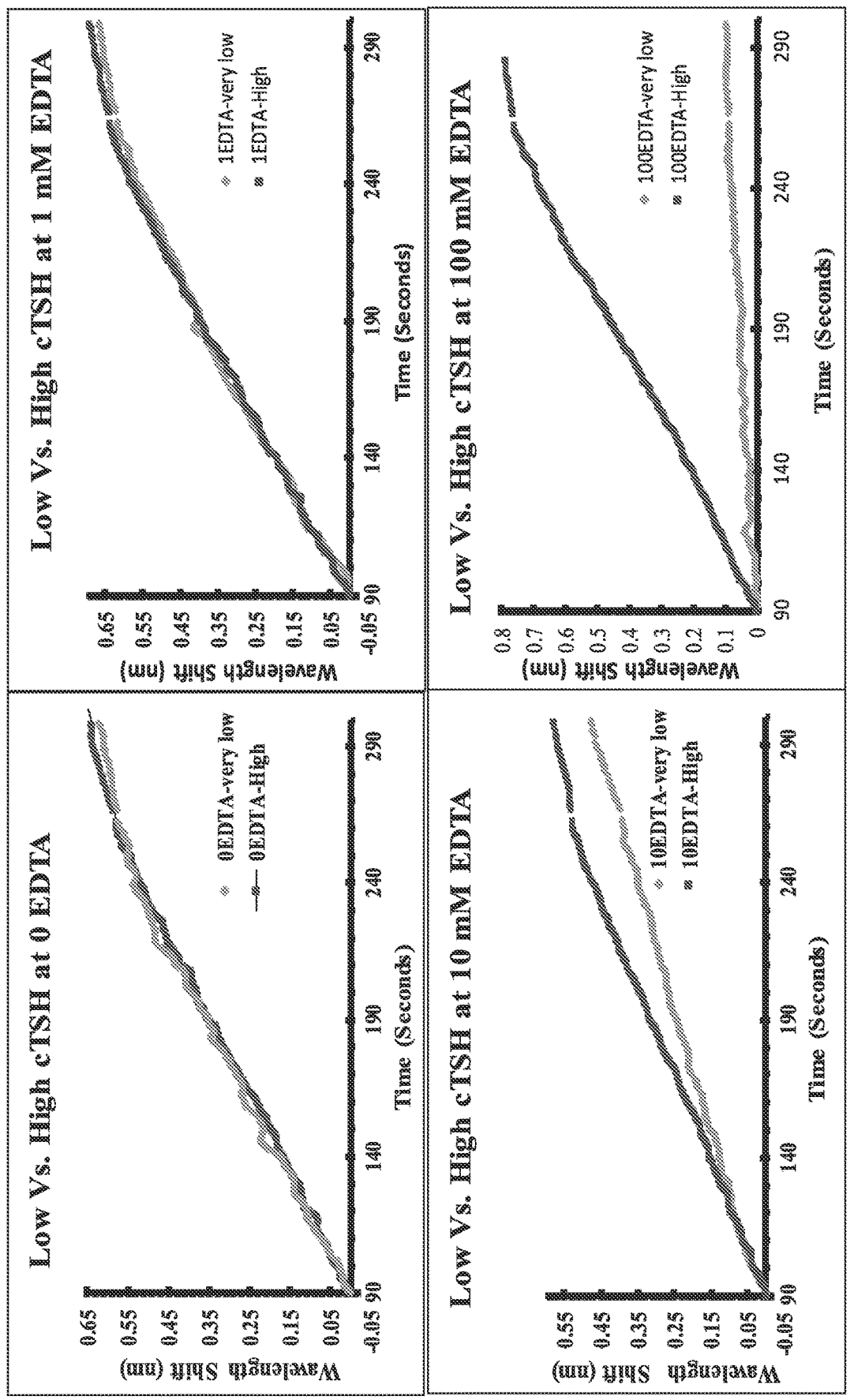
FIG. 30 shows the effects of the presence of EDTA on non-specific binding in the LSPR assay.

In another study, a very low pooled sample (<100 pg/ml of cTSH in TBS buffer) and a high sample (10 ng/ml in TBS buffer) were used to confirm the beneficial effects of the presence of Mg(II) on non-specific binding in a canine TSH assay based on LSPR. In the presence of 0 mM MgCl$_2$, the wavelength shift of the very low and the high cTSH samples was the same (FIG. 29, top left panel). At increasing concentrations of MgCl$_2$ (1 mM, 10 mM, or 100 mM, in the top right, bottom left, and bottom right panels of FIG. 29, respectively), the wavelength shift in the very low sample was reduced. Thus, the study confirmed that Mg(II) substantially reduced non-specific binding when present at 100 mM (FIG. 29). To understand the mechanism of Mg(II) effects on the LSPR signal, a second experiment was carried out in which EDTA (a chelator) was used. Surprisingly, EDTA showed effects similar to those of Mg(II) (FIG. 30). Even more surprisingly, EDTA and Mg(II) together did not appear to counteract each other. This was particularly surprising at least because EDTA would be expected to chelate Mg(II) and cause Mg(II) to lose its effect. Accordingly, the study showed that a combination of Mg(II), optionally with other Hofmeister series salts and along with EDTA or ethylene glycol-bis(β-aminoethyl ether)-N,N,N',N'-tetraacetic acid (EGTA), completely controls the non-specific binding in LSPR based assays. These surprising results were achieved in studies using either spherical nanostructures or nanoparticles that comprise a plurality of protrusions on the surface.

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

The invention claimed is:

1. A method of detecting a target analyte in a sample comprising:
(a) mixing the sample, a first detection conjugate, and a second detection conjugate with 3-((3-Cholamidopropyl) dimethylammino)-1-propanesulfonate (CHAPS), a blocking agent, one or more polymeric material, one or more viscosity enhancer, a salt, and optionally a chelator, in a solution, wherein the first and second detection conjugates comprise nanostructures coupled to binding partners that are capable of specifically binding to the target analyte if present in the sample to form a complex between the first detection conjugate, the analyte, and the second detection conjugate wherein the nanostructures comprise a plurality of protrusions and wherein the average tip to tip diameter of the nanostructures is from about 50 nm to about 120 nm;
(b) exposing the complex to a light source at a wavelength range within the ultraviolet-visible-infrared spectrum; and
(c) measuring an optical signal from the complex, wherein a change in the optical signal from a baseline optical signal obtained from the sample without the target analyte indicates the presence of the target analyte in the sample.

2. The method of claim 1, wherein the average tip to tip diameter of the nanostructures is from about 70 nm to about 90 nm, about 70 nm, or about 90 nm.

3. The method of claim 1, wherein step (a) of mixing occurs in the presence of:
(i) a polymeric material selected from polyethylene glycol (PEG), polyvinyl pyrrolidone, gelatin, a cellulose, methylcellulose, dextran, polyallylamine, polyethyleneimine, polylysine, polyacrylic acid, polyvinylalcohol, and polyaspartic acid; or
(ii) the viscosity enhancer is selected from the group consisting of trehalose, maltodextrin, sucrose, sorbitol, mannitol, polyvinylpyrrolidone (PVP), polyvinyl alcohol (PVA), cyclodextrin, methylcellulose, dextran, and ficoll; or
(iii) the blocking agent is selected from bovine serum albumin (BSA), casein, gelatin, ovalbumin, and gamma-globulins; or
(iv) the salt is selected from the group consisting of NaCl, $MgCl_2$, $CaCl_2$), and NaSCN;
(v) the chelator is selected from the group consisting of Ethylenediaminetetraacetic acid (EDTA) and ethylene glycol-bis(3-aminoethyl ether)-N,N,N',N'-tetraacetic acid (EGTA) or
(vi) wherein the CHAPS is present at a concentration of about 0.1% w/v to about 0.5% w/v, or about 0.2% w/v.

4. The method of claim 3, wherein the EDTA or the EGTA is present in the solution at a concentration of about 5 mM to about 100 mM.

5. The method of claim 1, wherein:
(i) the optical signal is reflectance, an absorbance spectrum, scattering spectrum, or an emission spectrum; or
(ii) the change in the optical signal comprises a spectral peak wavelength shift and/or a total spectral profile shift; wherein the total spectral profile shift is a difference spectrum; or
(iii) the presence of nanogram, picogram, or femtogram quantities of the target analyte is detected.

6. The method of claim 1, wherein step (a) is performed in a spectrophotometric cuvette, an analytical rotor, a microwell plate, a clinical analyzer, a flow chamber, on the tip of an optical fiber, or in a transparent gel.

7. The method of claim 1, wherein the nanostructures are gold metallic nanostructures.

8. The method of claim 1, wherein the binding partner is a biological macromolecule selected from an antibody or a fragment thereof, an antigen, a receptor, a ligand, a polynucleotide, an aptamer, a polypeptide, a polysaccharide, a lipopolysaccharide, a glycopeptide, a lipoprotein, and a nucleoprotein.

9. The method of claim 1, wherein the first detection conjugate and the second detection conjugate comprise binding partners that are antibodies; wherein the antibodies bind different epitopes on the target analyte.

10. The method of claim 1, wherein the target analyte is:
(i) selected from a protein, enzyme, antigen, antibody, peptide, nucleic acid, hormone, glycoprotein, polysaccharide, toxin, virus, virus particle, drug molecule, hapten, and a chemical; or
(ii) is a pathogenic antigen or antibody to a pathogenic antigen; wherein
(a) the pathogenic antigen is a viral antigen; wherein the viral antigen is from a virus selected from feline leukemia virus, canine parvovirus, foot and mouth virus, influenza virus, hepatitis a virus, hepatitis b, hepatitis c virus, HIV virus, human papilloma virus, Epstein Barr virus, and rabies virus; or
(b) the pathogenic antigen is a bacterial antigen; wherein the bacterial antigen is selected from *Ehrlichia, Borrelia, Anaplasma, Salmonella, Bacillus, Rickettsia, Ehrlichia canis, Ehrlichia chaffeensis, Ehrlichia ewingii, Borrelia burgdorferi, Anaplasma platys, Anaplasma phagocytophilum, Salmonella enterica, Bacillus anthracis,* and *Rickettsia rickettsii*; or
(c) the pathogenic antigen is a fungal antigen or a parasitic antigen; wherein the fungal antigen or parasitic antigen is selected from canine heartworm, *Giardia lamblia, Plasmodium falciparum,* African trypanosomiasis, and *Trypanosoma brucei.*

11. The method of claim 1, wherein the solution of step (a) further comprises a polymer substrate with a polar charged head group and a tail, the tail having one or more properties selected from the group consisting of hydrophobic, anionic, cationic, and hydrogen bond donating.

12. The method of claim 1, wherein the nanostructures are selected from the group consisting of spherical nanoparticles and nanoparticles comprising a plurality of protrusions.

13. The method of claim 3, wherein the polymeric material is PEG, and wherein the PEG is present at a concentration from about 0.1% to about 5% w/v.

14. The method of claim 3, wherein the blocking agent is BSA and wherein the BSA present at a concentration of about 1% to about 5% w/v.

* * * * *